(12) United States Patent
Small-Howard et al.

(10) Patent No.: US 11,260,044 B2
(45) Date of Patent: Mar. 1, 2022

(54) TRPV1 ACTIVATION-MODULATING COMPLEX MIXTURES OF CANNABINOIDS AND/OR TERPENES

(71) Applicant: GBS Global Biopharma, Inc., Ottowa (CA)

(72) Inventors: Andrea Small-Howard, Norwalk, CA (US); Helen Turner, Honolulu, HI (US)

(73) Assignee: GBS GLOBAL BIOPHARMA, INC., Ottowa (CA)

( * ) Notice: Subject to any disclaimer, the term of this patent is extended or adjusted under 35 U.S.C. 154(b) by 0 days.

(21) Appl. No.: 16/420,004

(22) Filed: May 22, 2019

(65) Prior Publication Data

US 2019/0374501 A1    Dec. 12, 2019

Related U.S. Application Data

(60) Provisional application No. 62/674,843, filed on May 22, 2018, provisional application No. 62/769,743, filed on Nov. 20, 2018, provisional application No. 62/849,719, filed on May 17, 2019.

(51) Int. Cl.
*A61K 31/352* (2006.01)
*A61K 31/01* (2006.01)
*A61K 31/05* (2006.01)

(52) U.S. Cl.
CPC ............ *A61K 31/352* (2013.01); *A61K 31/01* (2013.01); *A61K 31/05* (2013.01)

(58) Field of Classification Search
CPC .... A61K 31/01; A61K 31/015; A61K 31/045; A61K 31/05; A61K 31/352
See application file for complete search history.

(56) References Cited

U.S. PATENT DOCUMENTS

| | | | |
|---|---|---|---|
| 9,084,786 B2 | 7/2015 | Stokes | |
| 9,095,554 B2* | 8/2015 | Lewis | A01G 22/00 |
| 2007/0105086 A1 | 5/2007 | Qin et al. | |
| 2010/0249223 A1* | 9/2010 | Di Marzo | A61K 36/185 514/454 |
| 2014/0298511 A1 | 10/2014 | Lewis et al. | |
| 2016/0250270 A1* | 9/2016 | Wendschuh | A61K 31/05 514/454 |
| 2018/0169035 A1* | 6/2018 | Eyal | A61K 31/05 |
| 2018/0215705 A1 | 8/2018 | Xie et al. | |
| 2018/0338930 A1 | 11/2018 | Small-Howard et al. | |

FOREIGN PATENT DOCUMENTS

| | | |
|---|---|---|
| WO | WO 2007/047752 A1 | 4/2007 |
| WO | WO 2014/159688 A1 | 10/2014 |
| WO | WO 2016/138505 A1 | 9/2016 |

(Continued)

OTHER PUBLICATIONS

Costa et al. (British Journal of Pharmacology, vol. 143 (2) 2004, pp. 247-250). (Year: 2004).*

(Continued)

*Primary Examiner* — Savitha M Rao
(74) *Attorney, Agent, or Firm* — Fenwick & West LLP

(57) ABSTRACT

Described are methods of modulating the activation of the TRPV1 ion channel by administering at least one cannabinoid and/or terpene compound.

11 Claims, 46 Drawing Sheets

(56) References Cited

FOREIGN PATENT DOCUMENTS

| WO | WO 2017/158539 A1 | 9/2017 |
|---|---|---|
| WO | WO 2018/071452 A1 | 4/2018 |
| WO | WO 2018/170596 A1 | 9/2018 |
| WO | WO 2018/217803 A3 | 11/2018 |
| WO | WO 2019/226833 A1 | 11/2019 |

OTHER PUBLICATIONS

Cuñetti, L. et al., "Chronic Pain Treatment with Cannabidiol in Kidney Transplant Patients in Uruguay," Transplantation Proceedings, vol. 50, No. 2, Mar. 2018, pp. 461-464.

Gomes Paula-Freire, L. et al., "Ocimum gratissimum Essential Oil and Its Isolated Compounds (Eugenol and Myrcene) Reduce Neuropathic Pain in Mice," Planta Med 82(3), Feb. 2016, pp. 211-216.

Hunter, D. et al., "Synthetic transdermal cannabidiol for the treatment of knee pain due to osteoarthritis," Osteoarthritis and Cartilage, vol. 26, No. Supplement 1, Apr. 1, 2018, pp. S26.

Katsuyama, S. et al., "Intraplantar Injection of Linalool Reduces Paclitaxel-Induced Acute Pain in Mice," Biomedical Research, vol. 33, Iss. 3, Jul. 2012, pp. 175-181.

PCT International Search Report and Written Opinion, PCT Application No. PCT/US2019/033618, dated Sep. 13, 2019, 14 pages.

Planells-Cases, R. et al., "Small molecules targeting the vanilloid receptor complex as drugs for inflammatory pain," Drugs of the Future, vol. 28, Iss. 8, Aug. 2003, pp. 787-795.

Bhattacharya, A. et al., "Pharmacology and antitussive efficacy of 4-(3-trifluoromethyl-pyridin-2-yl)-piperazine-1-carboxylic acid (5-trifluoromethyl-pyridin-2-yl)-amide (JNJ17203212), a transient receptor potential vanilloid 1 antagonist in guinea pigs," J. Pharmacol. Exp. Ther., vol. 323, No. 2, Aug. 9, 2007, pp. 665-674.

Booth, J. K. et al., "Terpene synthases from Cannabis sativa," PLOS One, Mar. 29, 2017, pp. 1-20.

Brito, R. et al., "TRPV1: A Potential Drug Target for Treating Various Diseases," Cells, vol. 3, May 23, 2014, pp. 517-545.

Dang, K. et al., "Cyclophosphamide-induced cystitis reduces ASIC channel but enhances TRPV1 receptor function in rat bladder sensory neurons," Journal of Neurophysiology, vol. 110, No. 2, Jul. 15, 2013, pp. 408-417.

De Petrocellis, L. et al., "Effects of cannabinoids and cannabinoid-enriched Cannabis extracts on TRP channels and endocannabinoid metabolic enzymes," British Journal of Pharmacology, vol. 163, Dec. 22, 2010, pp. 1479-1495.

De Petrocellis, L. et al., "Non-$CB_1$, Non-$CB_2$ receptors for endocannabinoids, plant cannabinoids, and synthetic cannabimimetics: focus on G-protein-coupled receptors and transient receptor potential channels," J Neuroimmune Pharmacol, vol. 5, Oct. 22, 2009, pp. 103-121.

Doherty, Am. J. et al., "Capsaicin responsiveness and cough in asthma and chronic obstructive pulmonary disease," Thorax, vol. 55, Aug. 1, 2000, pp. 643-649.

Dornelles, F. N. et al., "Role of CXCR2 and TRPV1 in functional, inflammatory and behavioural changes in the rat model of cyclophosphamide-induced haemorrhagic cystitis," British Journal of Pharmacology, vol. 171, Jan. 2014, pp. 452-467.

Groneberg, D. A. et al., "Increased expression of transient receptor potential vanilloid-1 in airway nerves of chronic cough," Am. J. Respir. Crit. Care Med., vol. 170, Sep. 24, 2004, pp. 1276-1280.

Lalloo, U. G. et al., "Capsazepine inhibits cough induced by capsaicin and citric acid but not by hypertonic saline in guinea pigs," J. Appl. Physiol., vol. 79, Issue 4, Oct. 1, 1995, pp. 1082-1087.

Mcleod, R. L. et al., "TRPV1 antagonists attenuate antigen-provoked cough in ovalbumin sensitized guinea pigs," Cough, Dec. 15, 2006, pp. 1-7.

Mickle, A. D. et al., "Sensory TRP Channels: The Key Transducers of Nociception and Pain," Progress in Molecular Biology and Translational Science, Chapter Four, vol. 131, Mar. 1, 2015, pp. 73-118.

Nakajima, T. et al., "Cough Sensitivity in Pure Cough Variant Asthma Elicited Using Continuous Capsaicin Inhalation," Allergology International, vol. 55, 2006, pp. 149-155.

O'Connell, F. et al., "Capsaicin cough sensitivity increases during upper respiratory infection," Respiratory Medicine, vol. 90, 1996, pp. 279-286.

Pecova, R. et al., "Cough reflex sensitivity testing in in seasonal allergic rhinitis patients and healthy volunteers," Journal of Physiology and Pharmacology, vol. 59, Suppl. 6, 2008, pp. 557-564.

Plevkova, J. et al., "Testing of cough reflex sensitivity in children suffering from allergic rhinitis and common cold," J. Physiol. Pharmacol., vol. 57, Suppl. 4, Sep. 2006, pp. 289-296.

Russo, E. B., "Taming THC: potential cannabis synergy and phytocannabinoid-terpenoid entourage effects," British Journal of Pharmacology, vol. 163, Aug. 2011, pp. 1344-1364.

Rybak, L.P. et al., "Ototoxicity," Kidney Int., vol. 72, Jul. 25, 2007, pp. 931-935.

Trevisani, M. et al., "Antitussive activity of iodo-resiniferatoxin in guinea pigs," Thorax, vol. 59, Aug. 27, 2004, pp. 769-772.

Wang, Z. Y. et al., "Lack of TRPV1 inhibits cystitis-induced increased mechanical sensitivity in mice," Pain, vol. 139, No. 1, Sep. 30, 2008, pp. 158-167.

Bautista, D., et al., "Fire in the Hole: Pore Dilation of the Capsaicin Receptor TRPV1 ," Nature Neuroscience, 2008, vol. 11, pp. 528-529.

Chung, M-K., et al., "TRPV1 Shows Dynamic Ionic Selectivity During Agonist Stimulation," Nature Neuroscience, 2008, vol. 11, pp. 555-564 (2008).

De Petrocellis, L., et al., "Cannabinoid Actions at TRPV Channels: Effects on TRPV3 and TRPV4 and Their Potential Relevance to Gastrointestinal Inflammation," Acta Physiol (Oxf)., Feb. 2012, vol. 204, No. 2, pp. 255-266.

De Petrocellis, L., et al., "Effects of Cannabinoids and Cannabinoid-Enriched Cannabis Extracts on TRP Channels and Endocannabinoid Metabolic Enzymes," Br J Pharmacol., Aug. 2011, vol. 163, No. 7, pp. 1479-1494.

De Petrocellis, L., et al., "Plant-Derived Cannabinoids Modulate the Activity of Transient Receptor Potential Channels of Ankyrin Type-1 and Melastatin type-8," J Pharmacol Exp Ther., Jun. 2008, vol. 325, No. 3, pp. 1007-1015.

Di Marzo, V. et al., "Endocannabinoids as Regulators of Transient Receptor Potential (TRP) Channels: A Further Opportunity to Develop New Endocannabinoid-Based Therapeutic Drugs," Current Medicinal Chemistry, 2010, pp. 1430-1449, vol. 17.

Iannotti, F.A. et al., "Nonpsychotropic Plant Cannabinoids, Cannabidivarin (CBDV) and Cannabidiol (CBD), Activate and Desensitize Transient Receptor Potential Vanilloid 1 (TRPV1) Channels in Vitro Potential for the Treatment of Neuronal Hyperexcitabilitv," ACS Chemical Neuroscience, 2014, pp. 1131-1141, vol. 5.

Morales, P. et al., "Molecular Targets of the Phytocannabinoids: A Complex Picture," Phytocannabinoids, AD. Kinghorn et al. (eds ), Progress in the Chemistry of Organic Natural Products, 2017, pp. 103-131.

PCT International Search Report and Written Opinion, PCT Application No. PCT/US2018/033956, dated Nov. 21, 2018, 17 pages.

United States Office Action, U.S. Appl. No. 15/986,316, dated May 15, 2019, 17 pages.

United States Office Action, U.S. Appl. No. 15/986,316, dated Dec. 26, 2019, 11 pages.

Carnevale, V. et al., "TRPV1: A Target for Rational Drug Design," Pharmaceuticals, vol. 9, No. 3, Aug. 23, 2016, pp. 1-20.

Elokely, K. et al., "Understanding TRPV1 activation by ligands: Insights from the binding modes of capsaicin and resiniferatoxin," Proceedings of the National Academy of Sciences, vol. 113, No. 2, Dec. 30, 2015, pp. E137-E145.

European Patent Office, Office Action, EP Patent Application No. 18769850.1, dated Nov. 30, 2020, ten pages.

Hudson, D. et al., "Biopolymer nanoparticle production for controlled release of biopharmaceuticals," CRC Critical Reviews in Biotechnology, vol. 34, No. 2, Jan. 7, 2013, pp. 161-179.

Jansen, C. et al., "Myrcene and terpene regulation of TRPV1," Channels (Austin), vol. 13, No. 1, Aug. 26, 2019, pp. 344-366.

(56) References Cited

OTHER PUBLICATIONS

Lee, J.H. et al., "Structural insights into transient receptor potential vanilloid type 1 (TRPV1) from homology modeling, flexible docking, and mutational studies," Journal of Computer-Aided Molecular Design, vol. 25, No. 4, Mar. 30, 2011, pp. 317-327.
PCT International Search Report and Written Opinion, PCT Application No. PCT/US2020/039989, dated Oct. 12, 2020, 19 pages.
Rao, V.S.N et al., "Effect of myrcene on nociception in mice," J. Pharm. Pharmacol., vol. 42, Dec. 1990, pp. 877-878.
Starkus, J. et al., "Diverse TRPV1 Responses to Cannabinoids," Channels (Austin), vol. 13, No. 1, Jan. 1, 2019, pp. 172-191.

\* cited by examiner

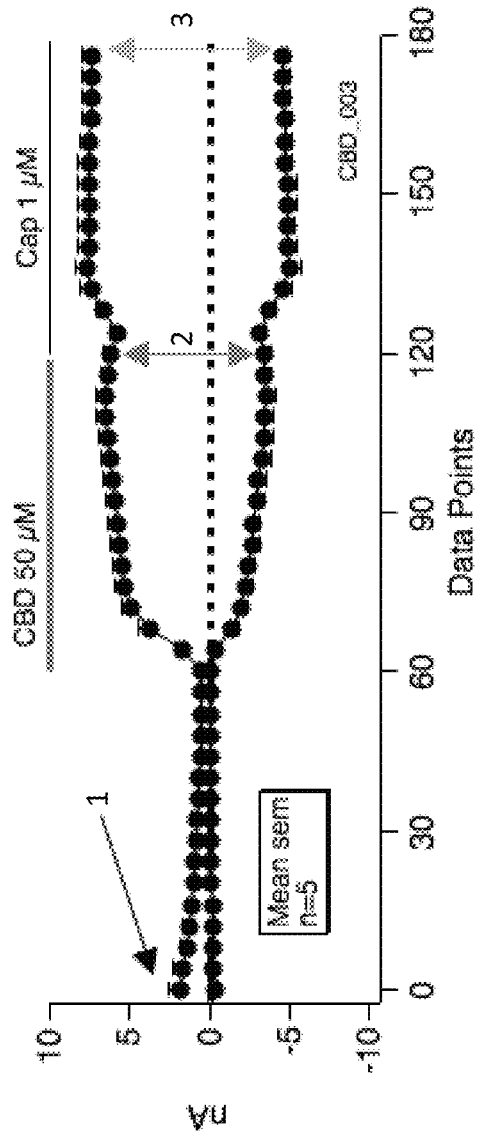
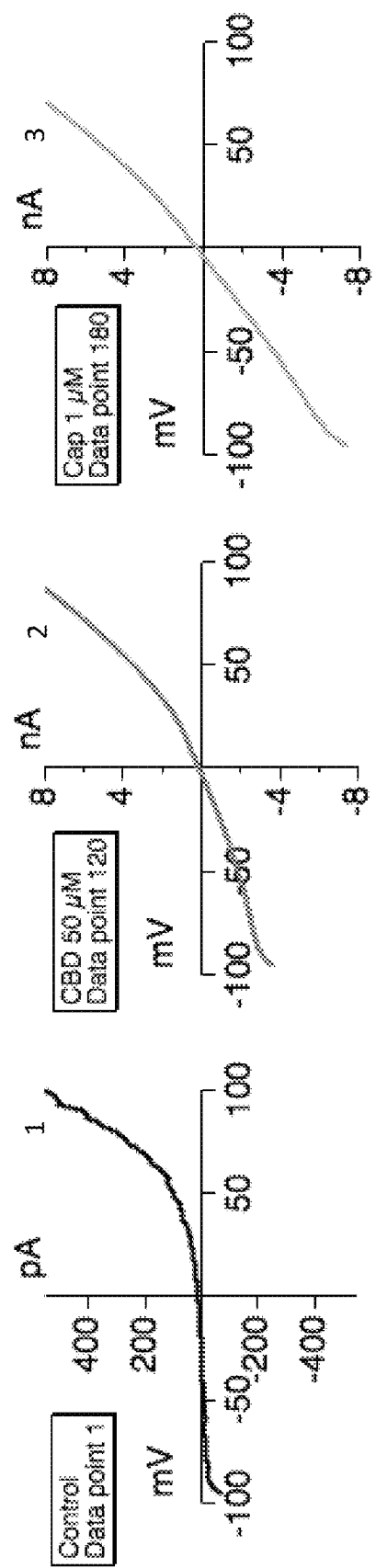
FIG. 3A
FIG. 3B
FIG. 3C
FIG. 3D

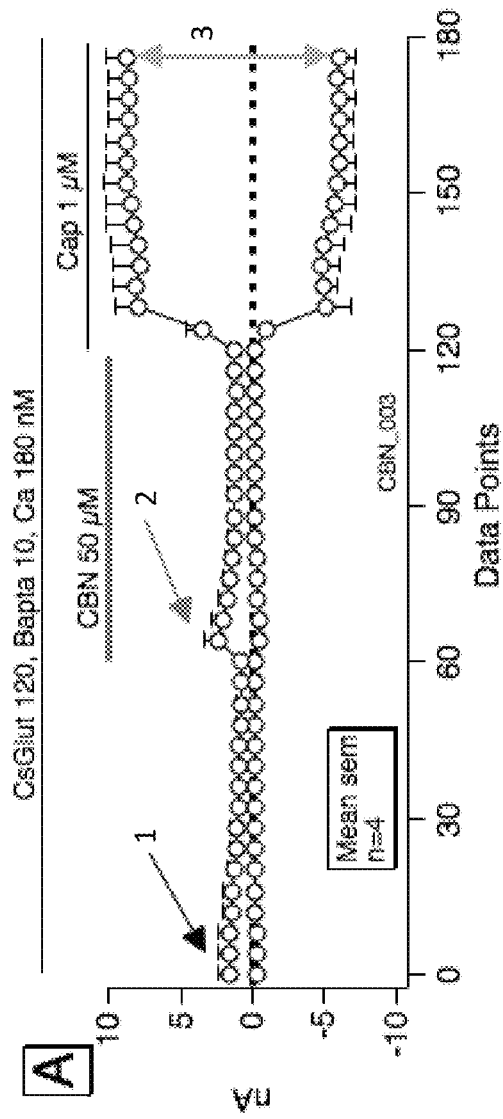
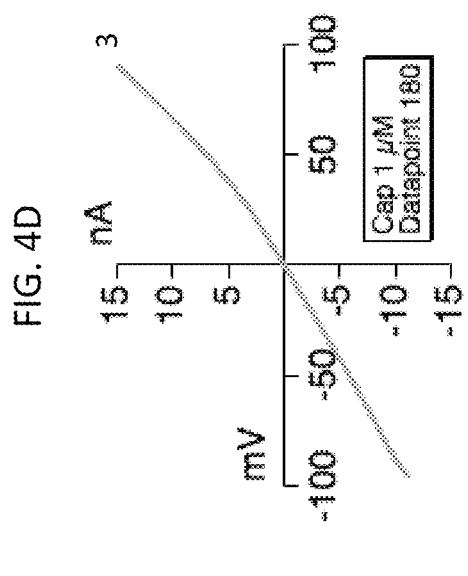
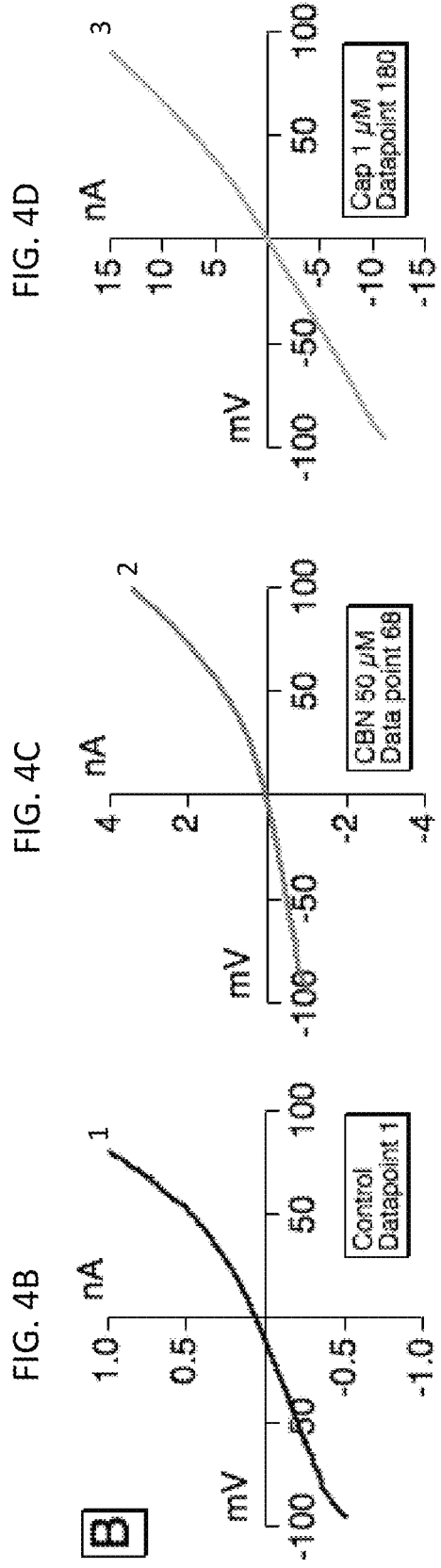
FIG. 4A
FIG. 4D
FIG. 4C
FIG. 4B

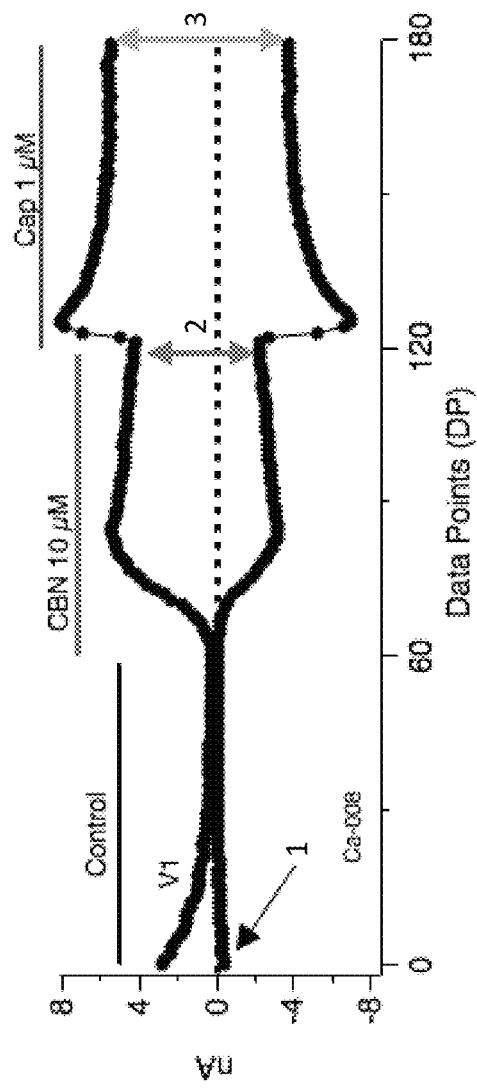
FIG. 5A
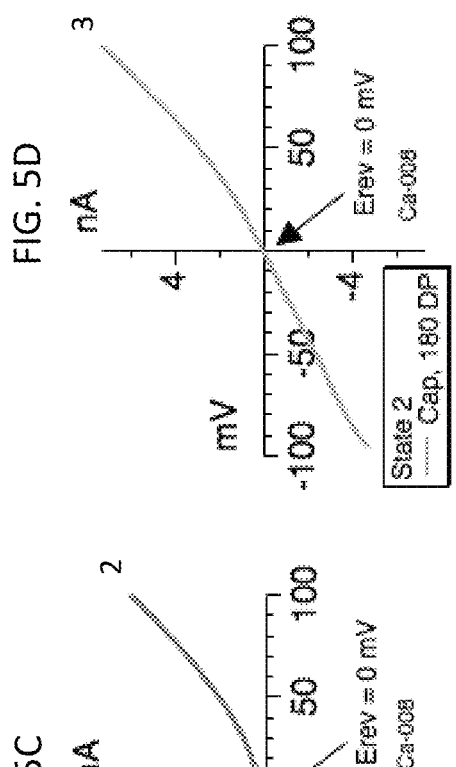
FIG. 5D
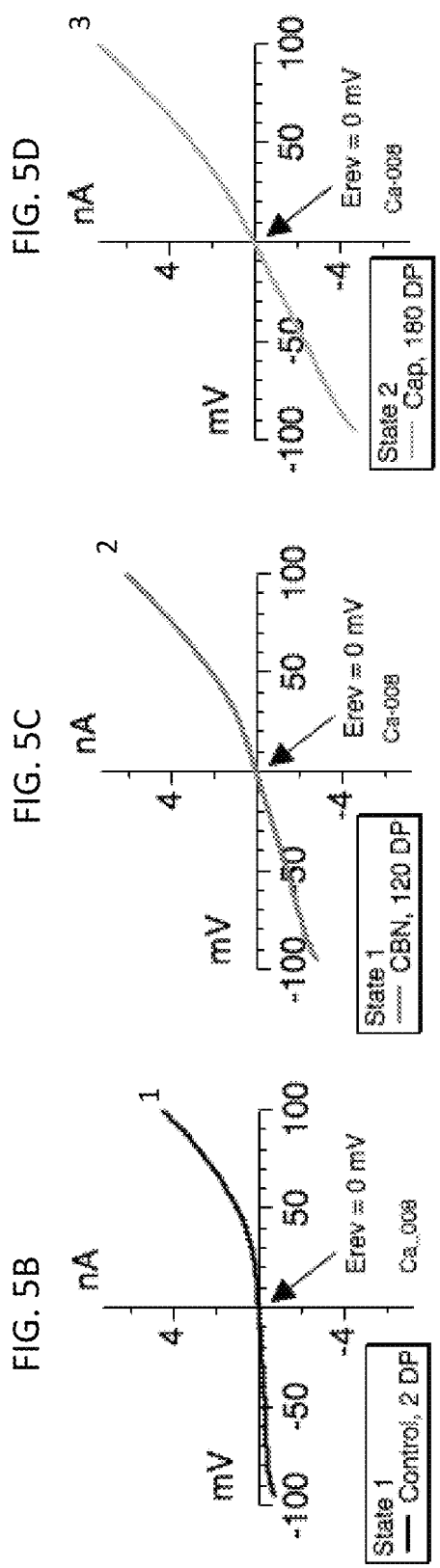
FIG. 5B
FIG. 5C

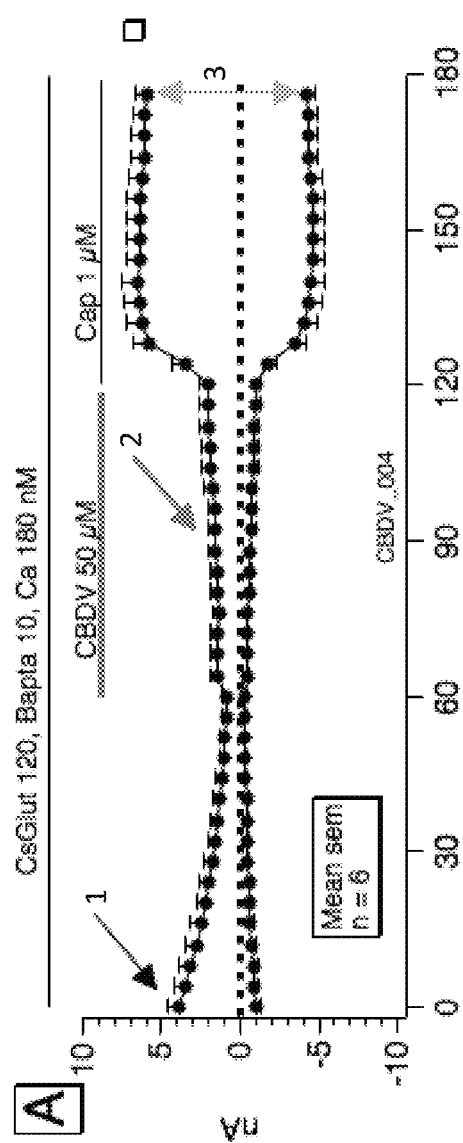
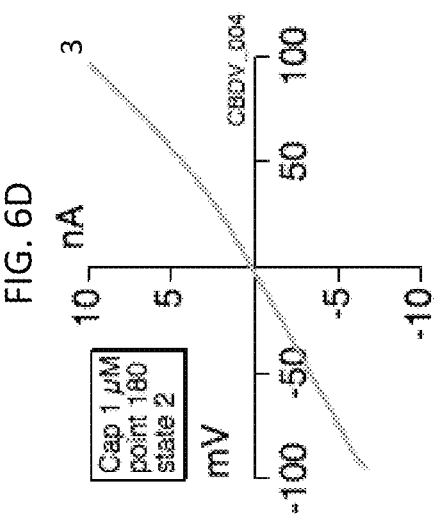
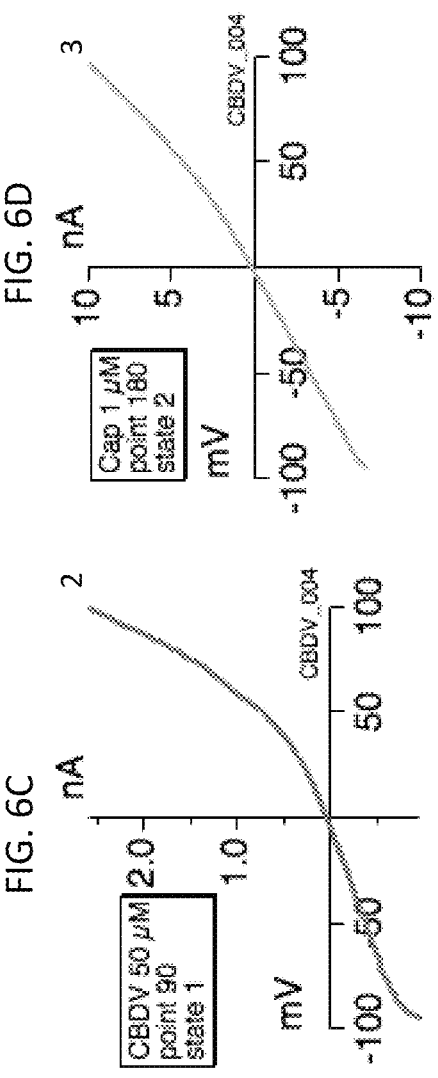
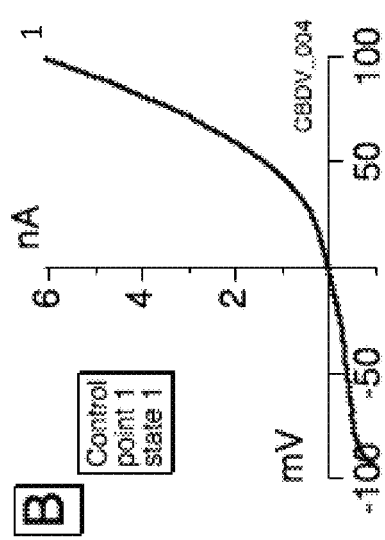
FIG. 6A
FIG. 6B
FIG. 6C
FIG. 6D

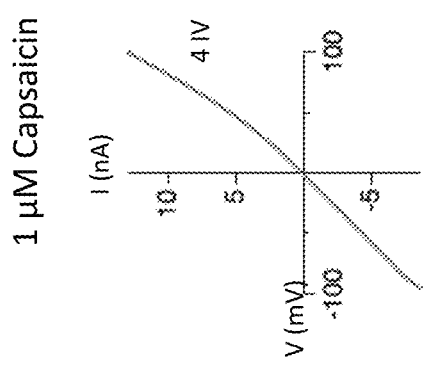
FIG. 9E
1 μM Capsaicin
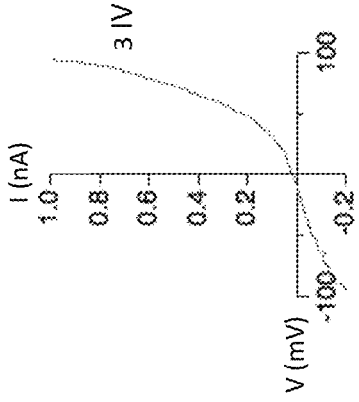
FIG. 9D
5 μM Myrcene
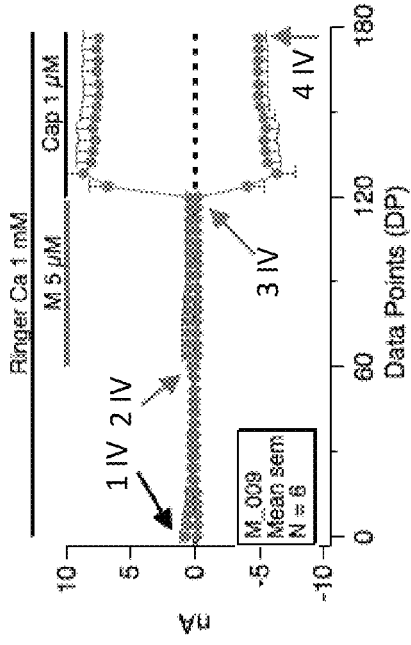
FIG. 9B
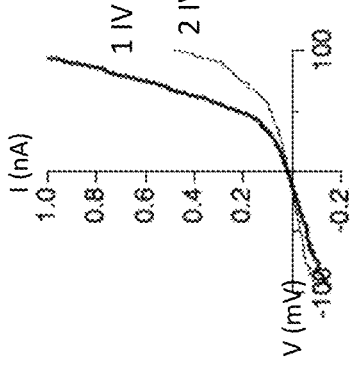
FIG. 9C
Ringer's Soln
FIG. 9A

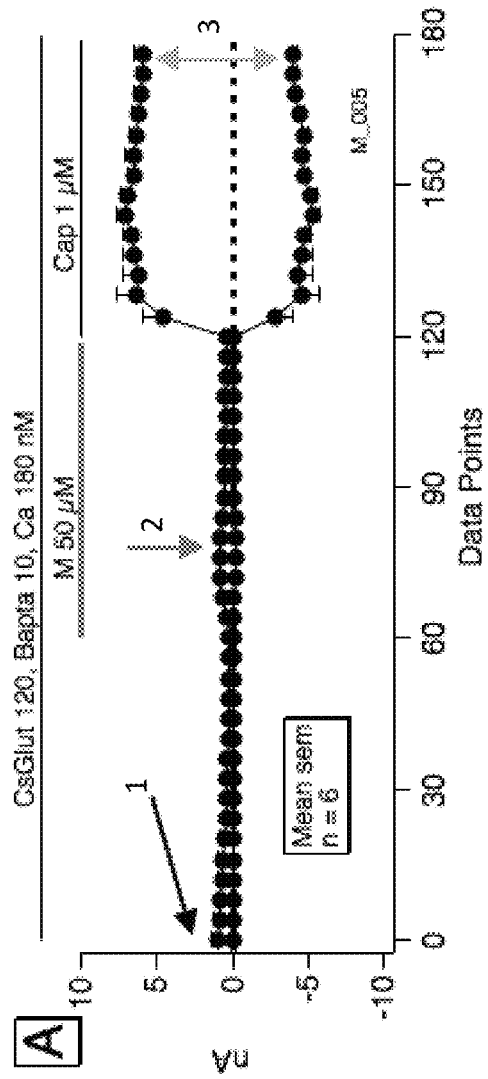
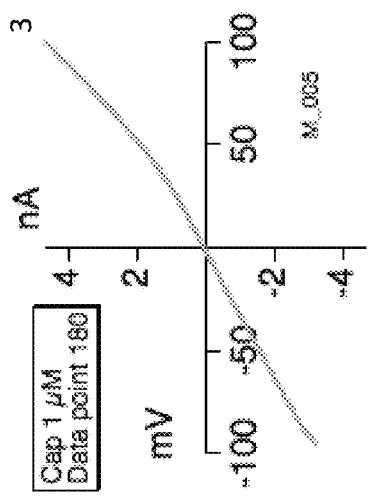
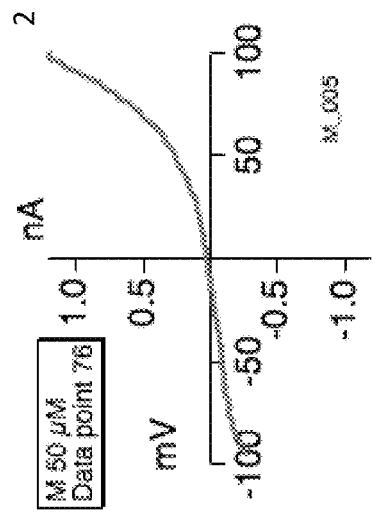
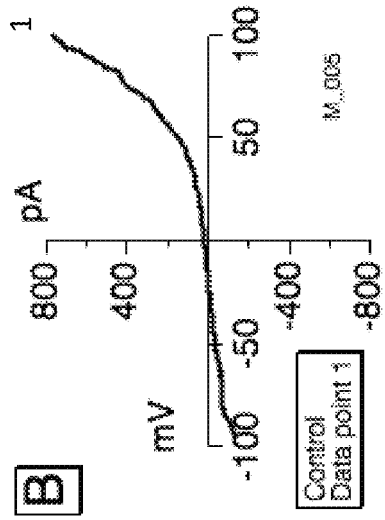
FIG. 10A
FIG. 10B
FIG. 10C
FIG. 10D

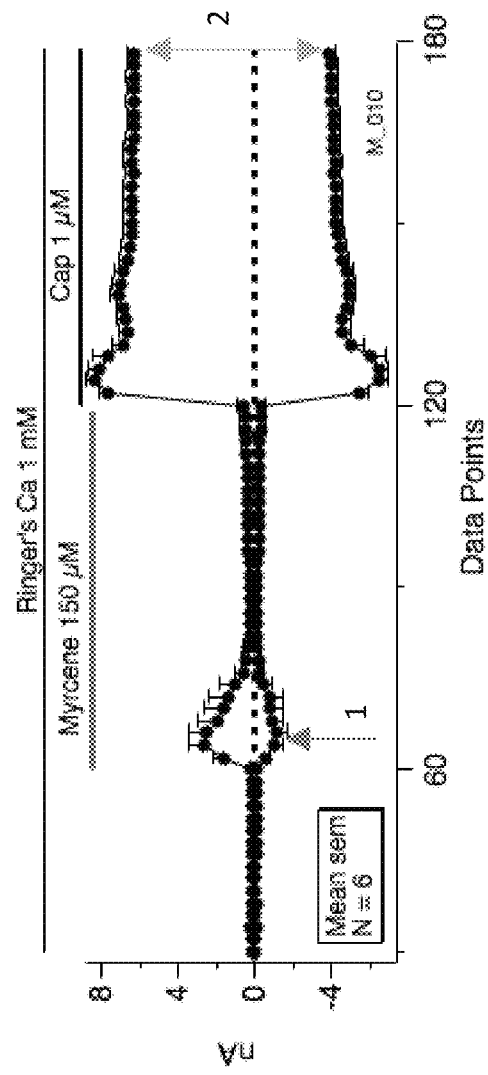
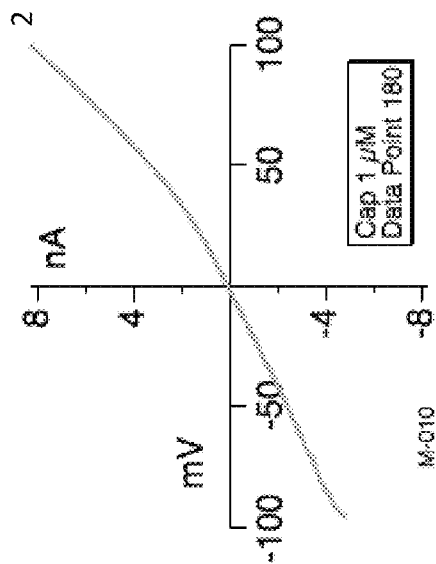
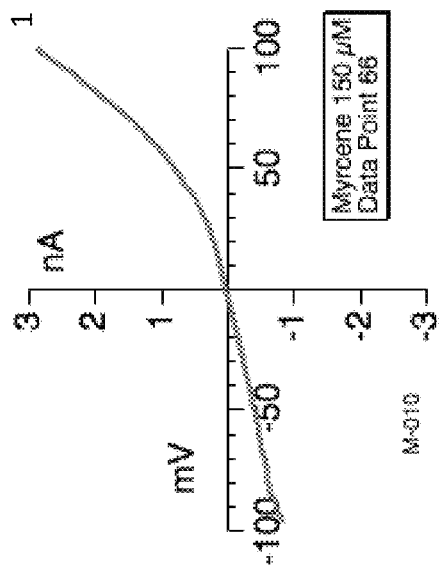
FIG. 11A
FIG. 11B
FIG. 11C

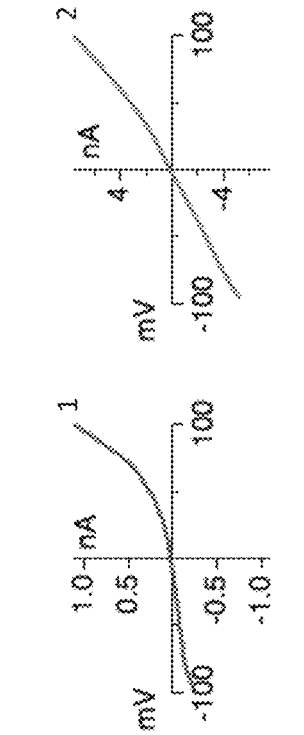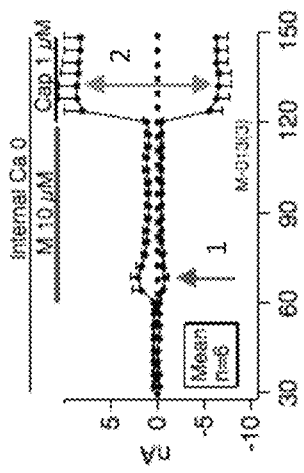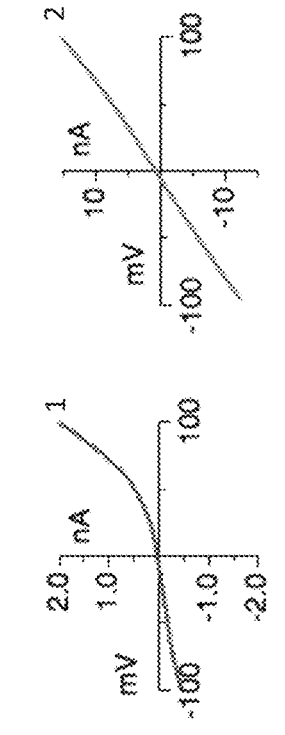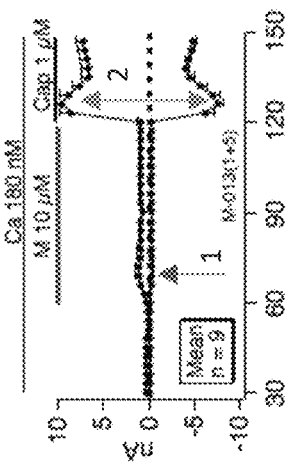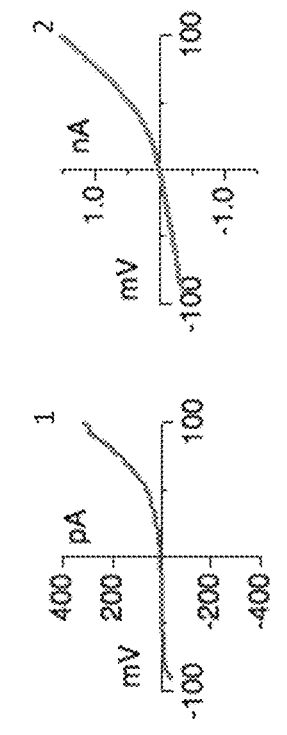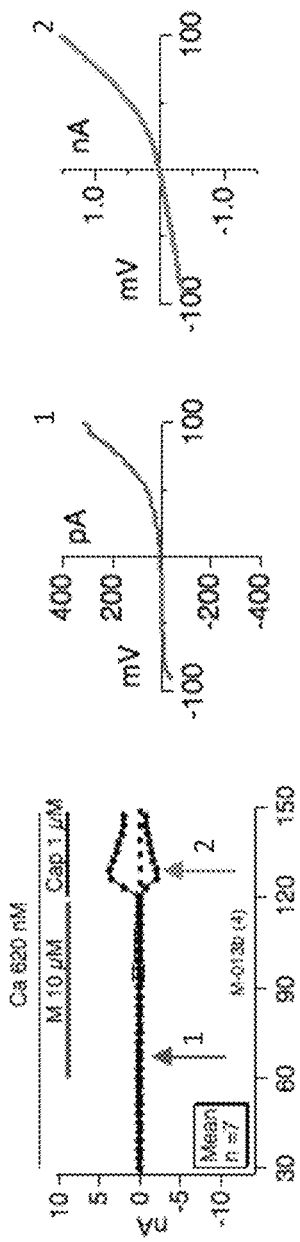

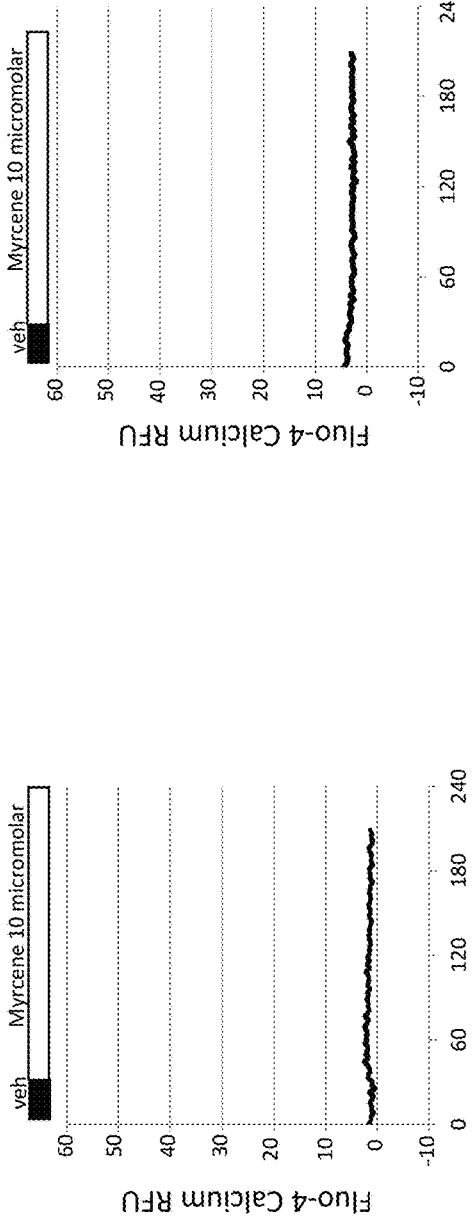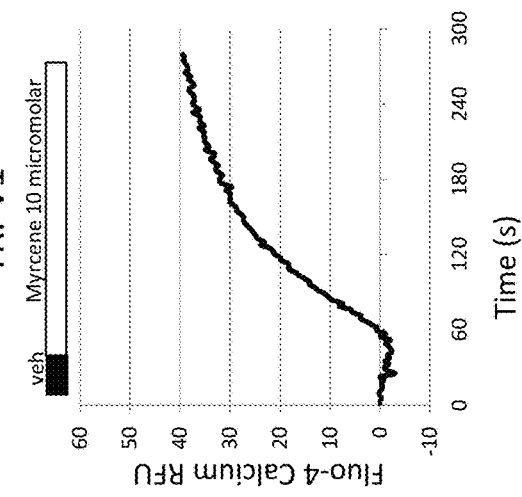

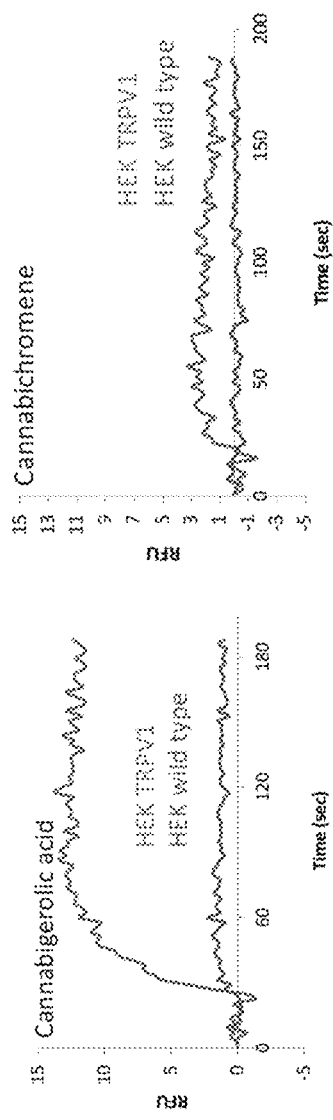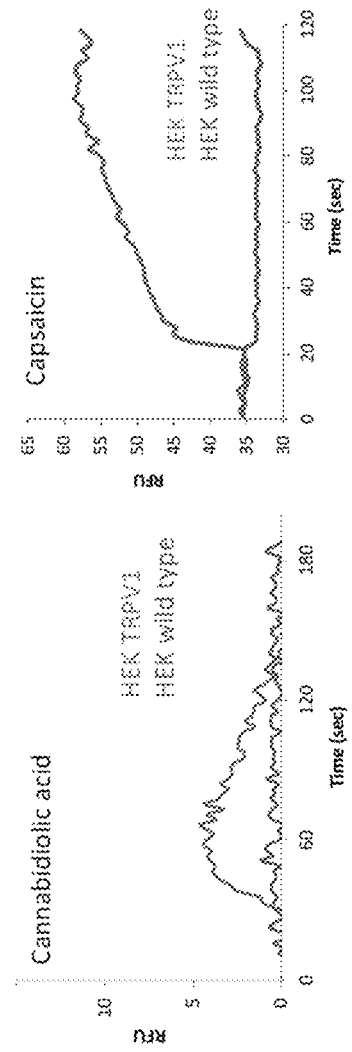

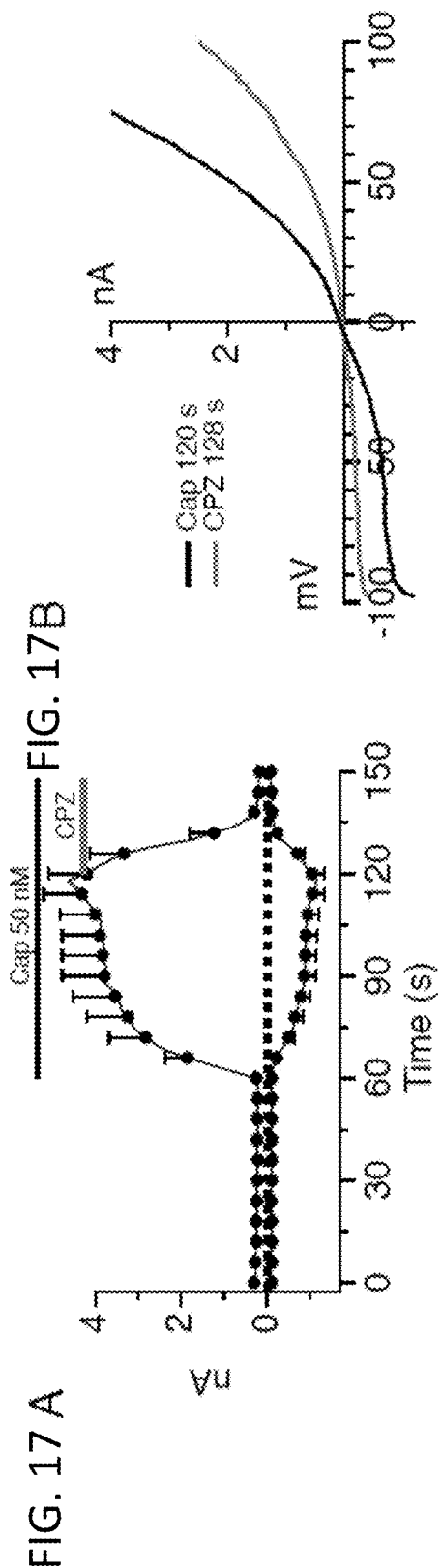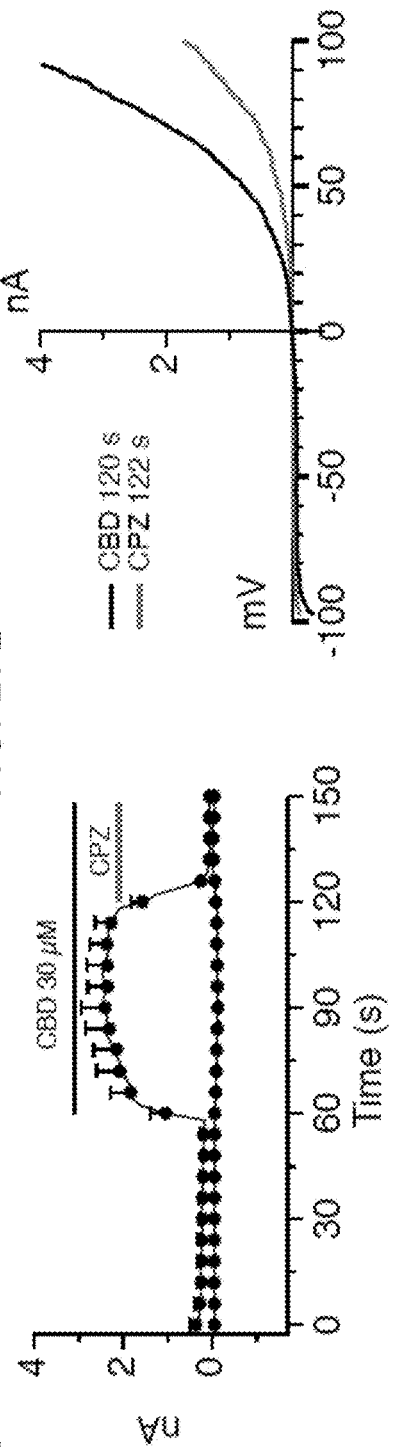
FIG. 17A  FIG. 17B  FIG. 17C  FIG. 17D

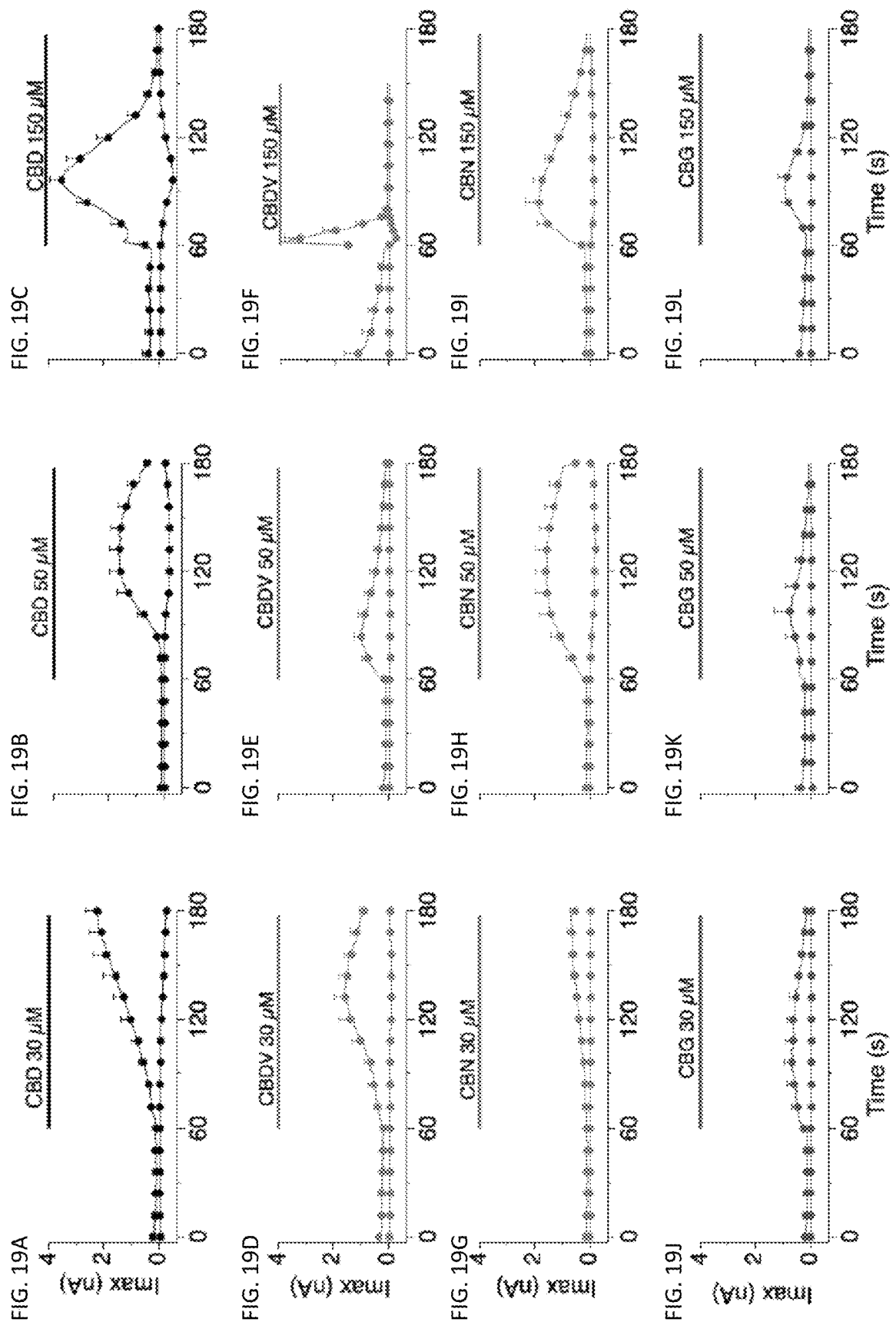

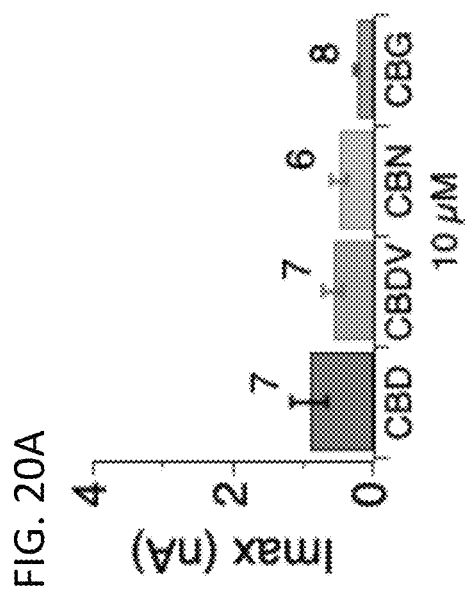
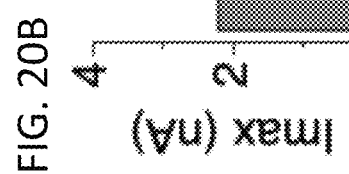
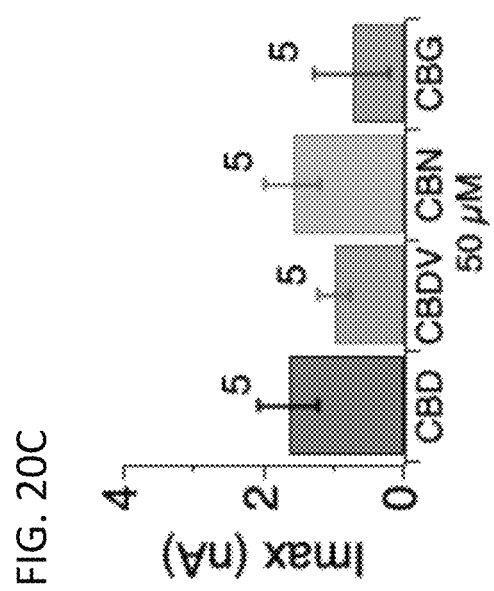
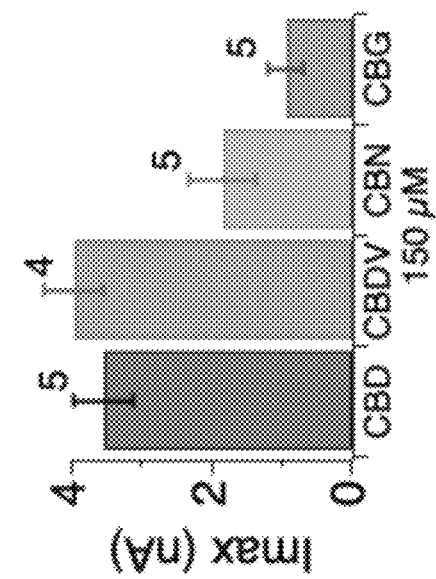

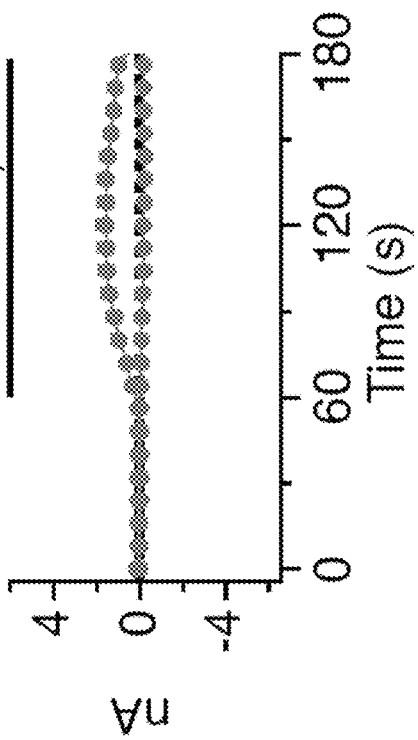
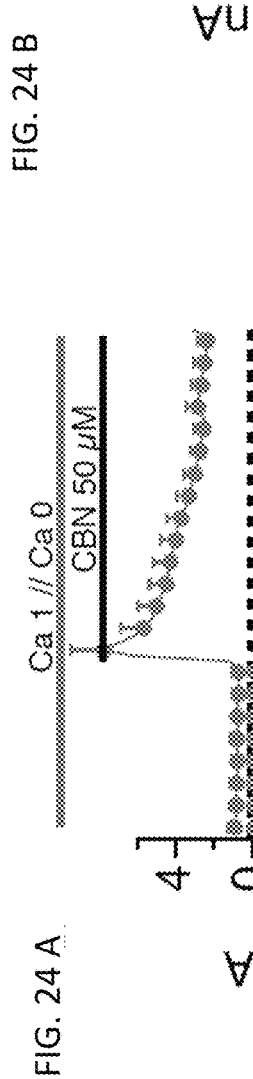
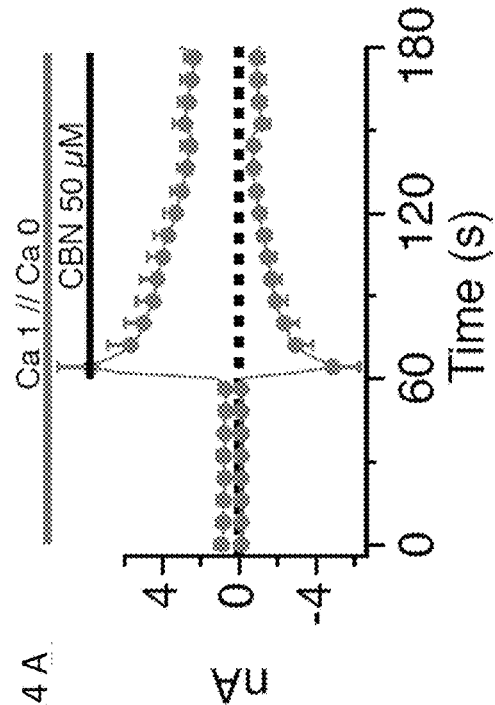
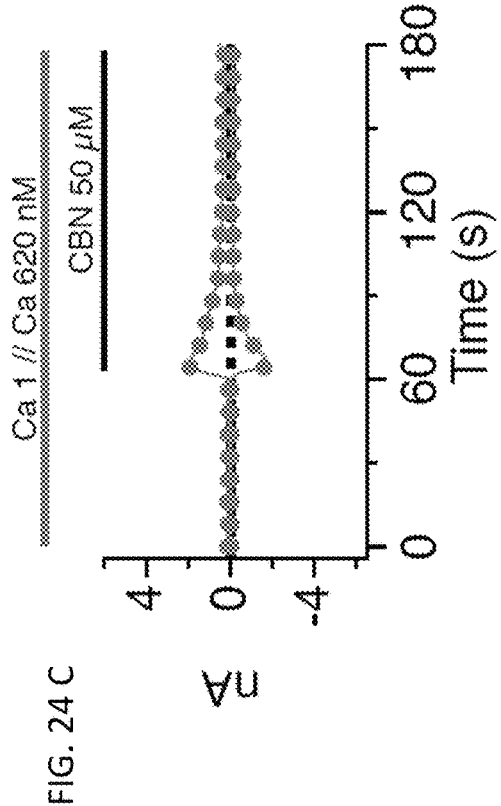
FIG. 24 A
FIG. 24 B
FIG. 24 C
FIG. 24 D

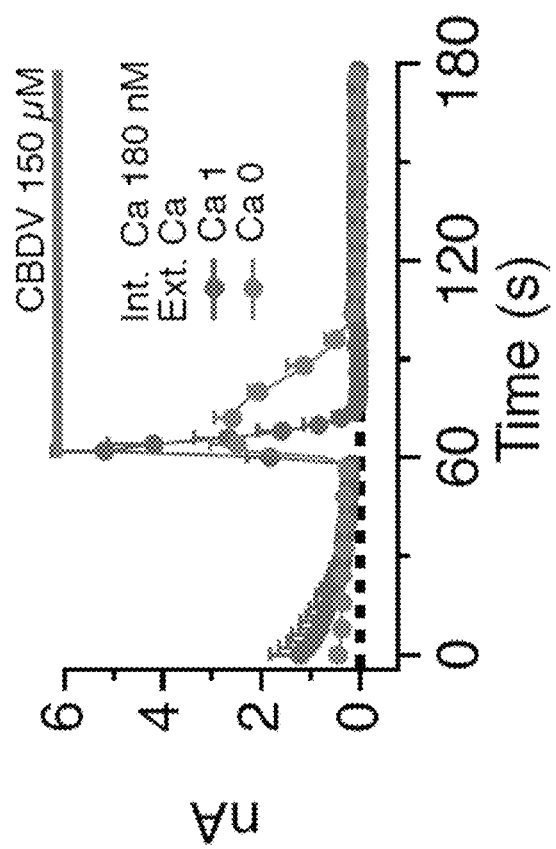
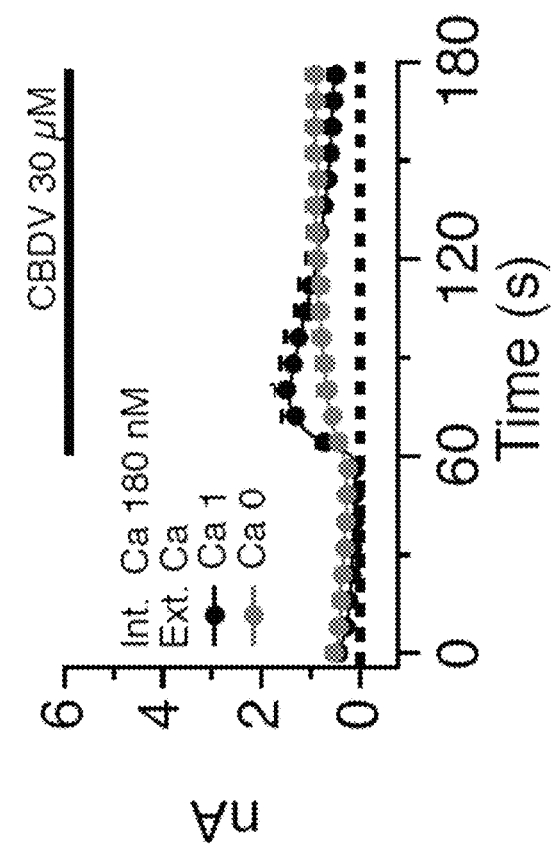
FIG. 28 B
FIG. 28 A

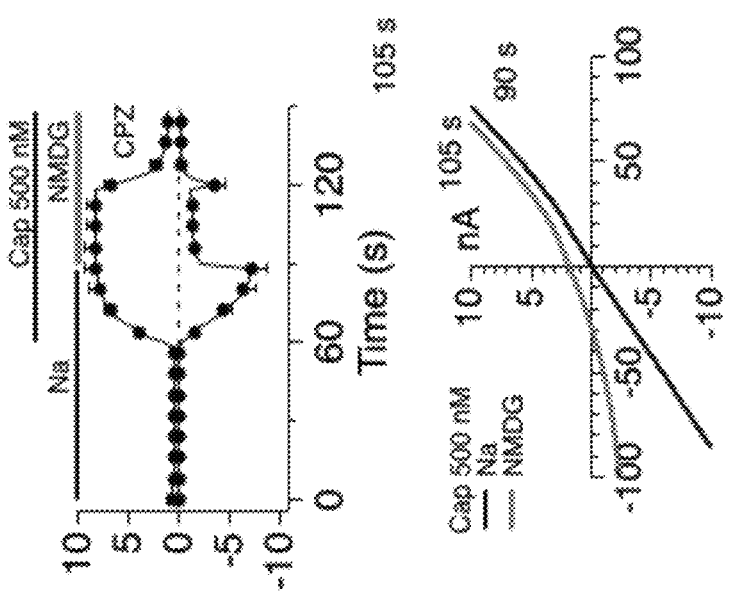
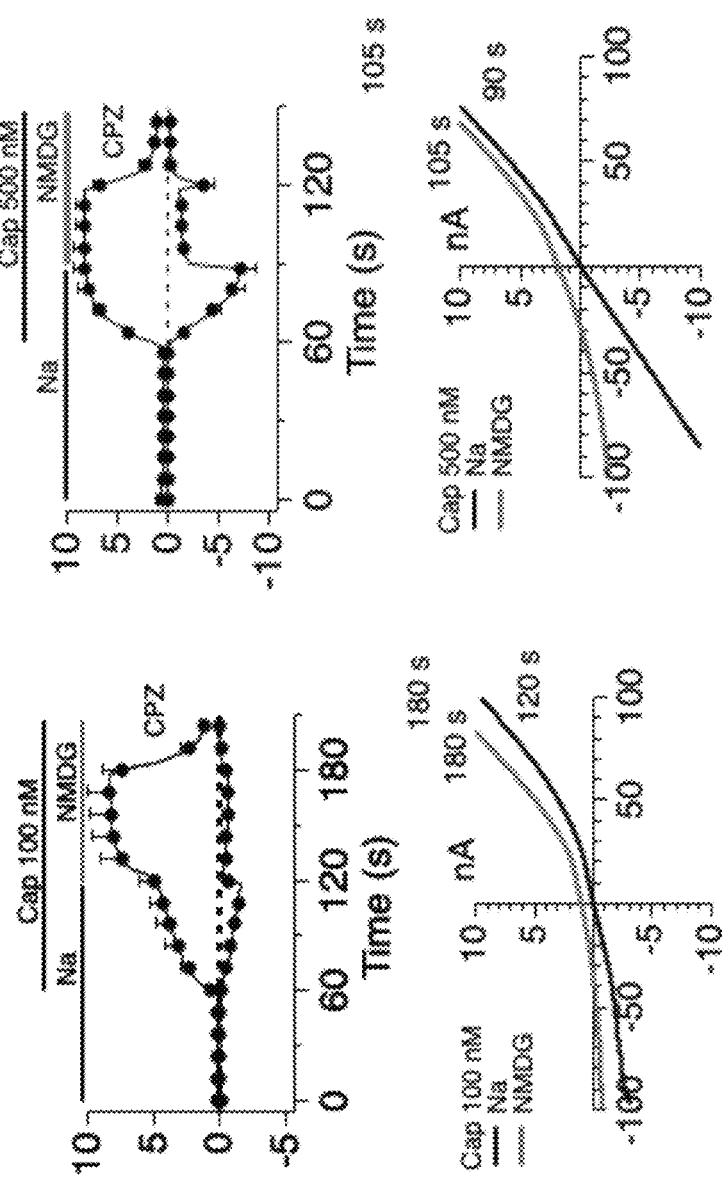
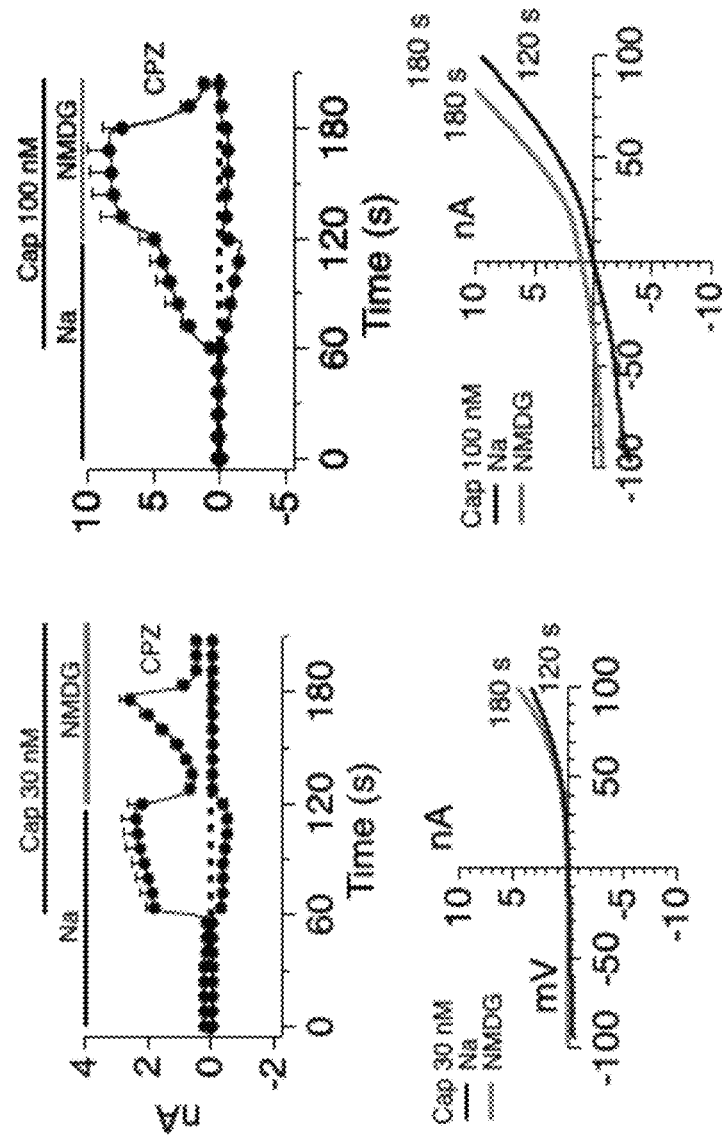
FIG. 31 A   FIG. 31 B   FIG. 31 C

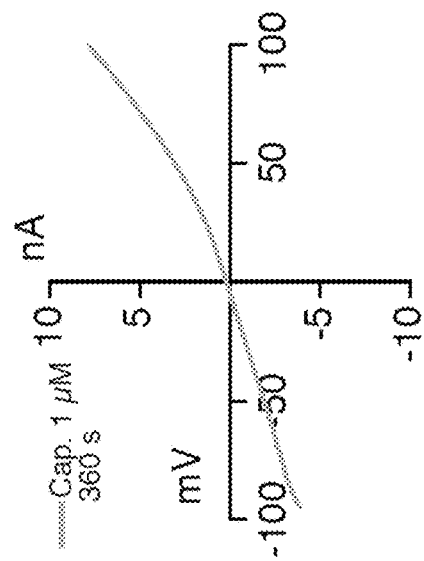
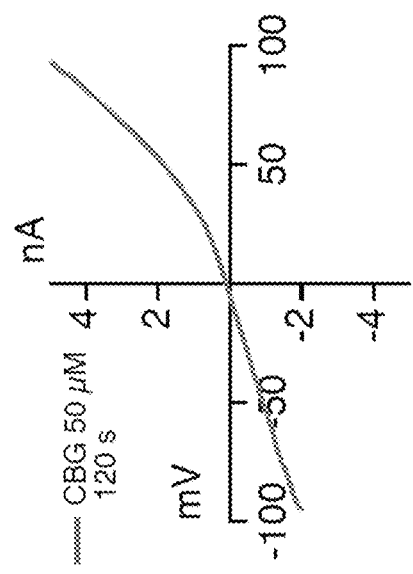
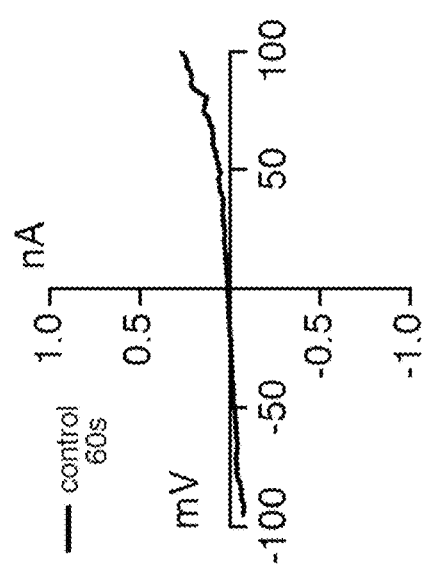

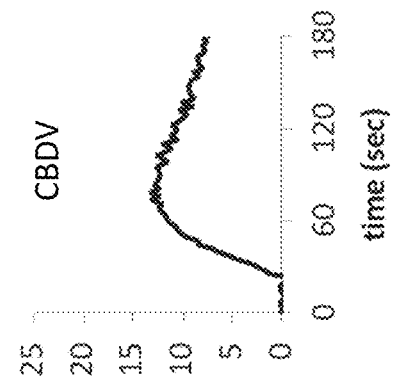
FIG. 41A CBD
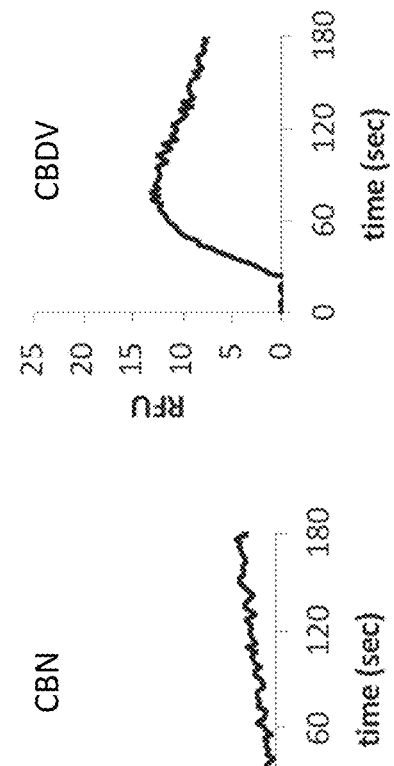
FIG. 41B CBN
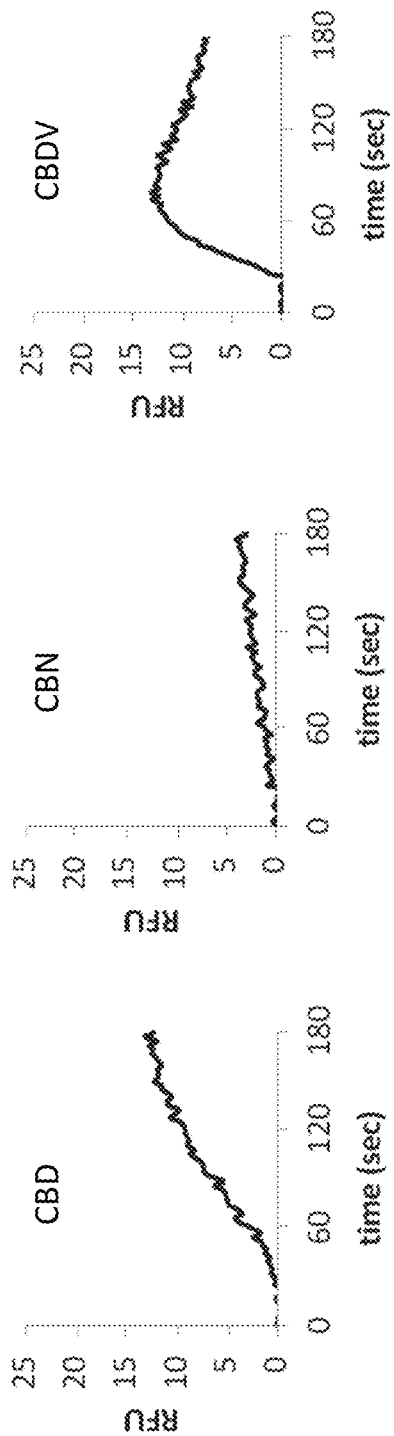
FIG. 41C CBDV
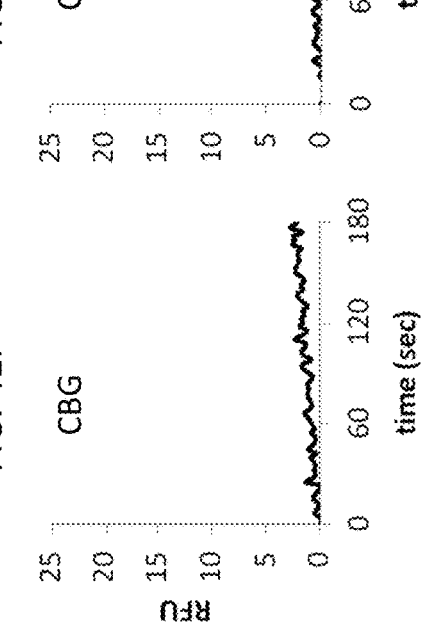
FIG. 41D CBC
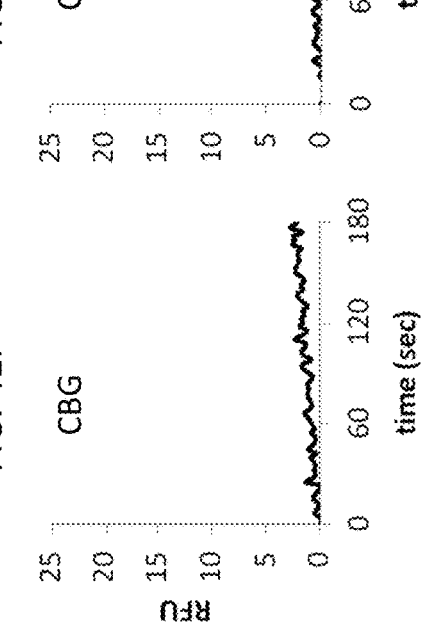
FIG. 41E CBDA
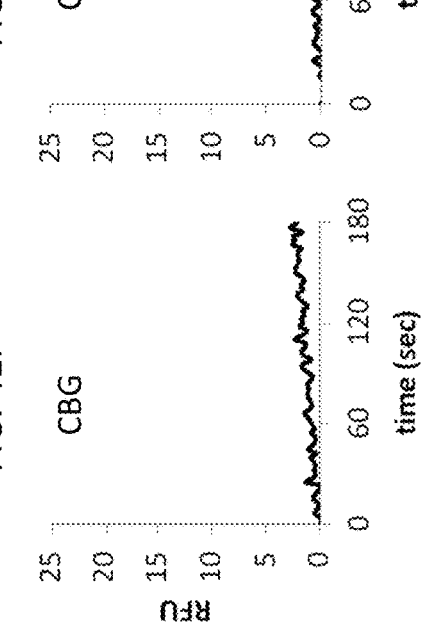
FIG. 41F CBG
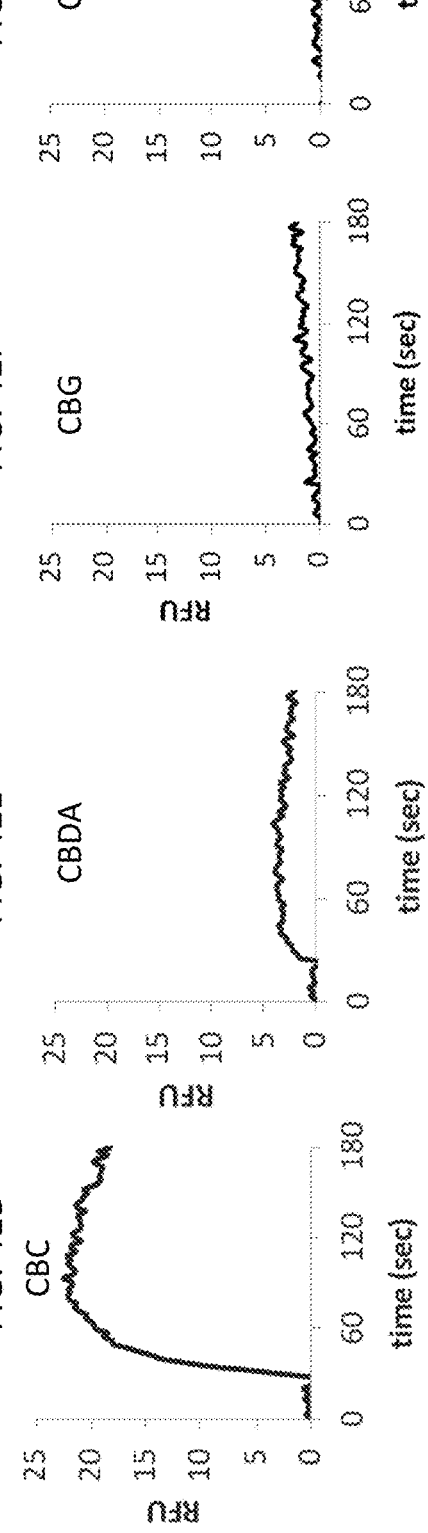
FIG. 41G CBGA

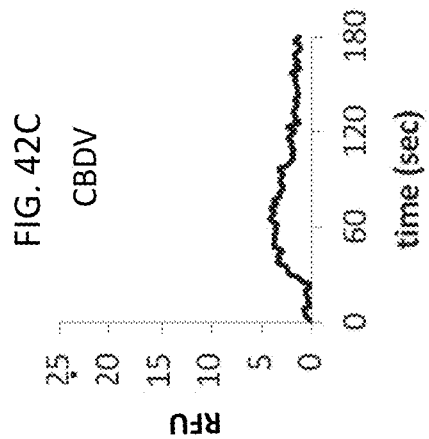
FIG. 42A CBD
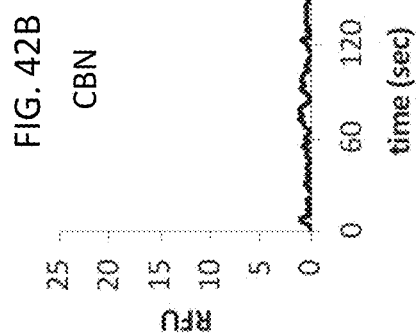
FIG. 42B CBN
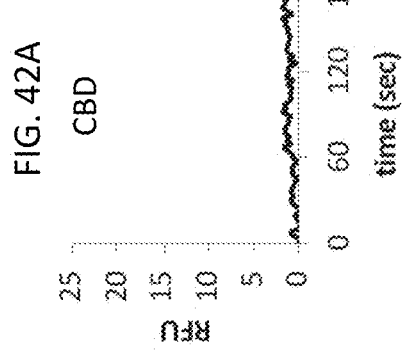
FIG. 42C CBDV

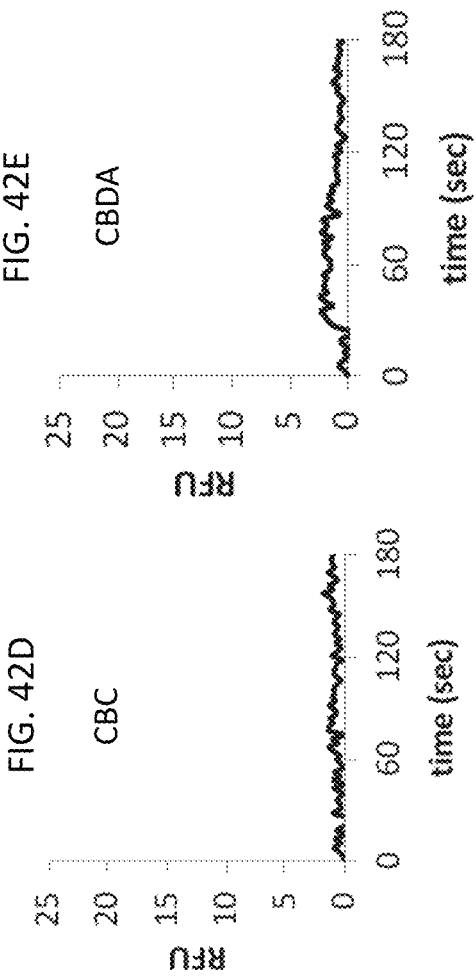
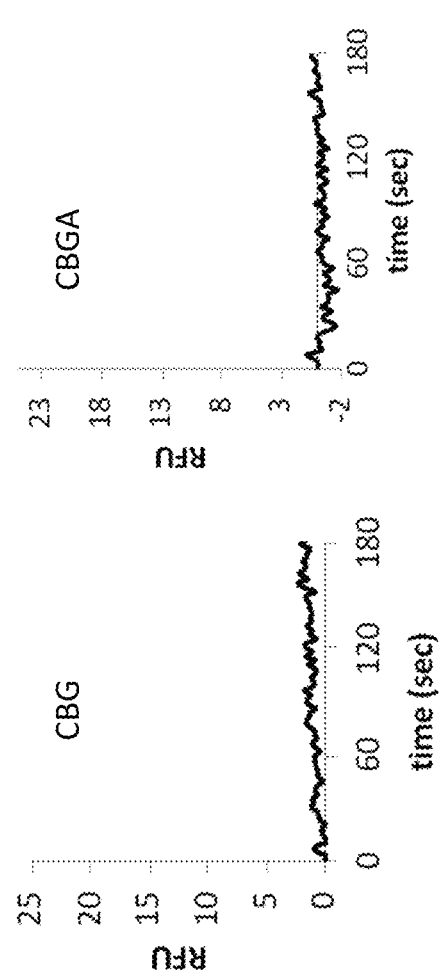
FIG. 42D CBC
FIG. 42E CBDA
FIG. 42F CBG
FIG. 42G CBGA

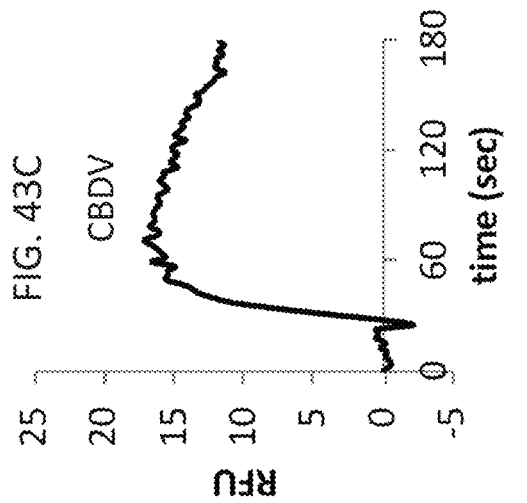
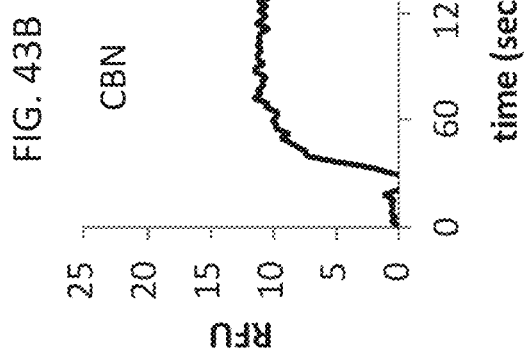
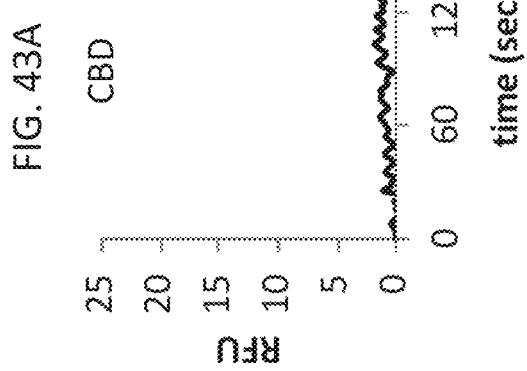

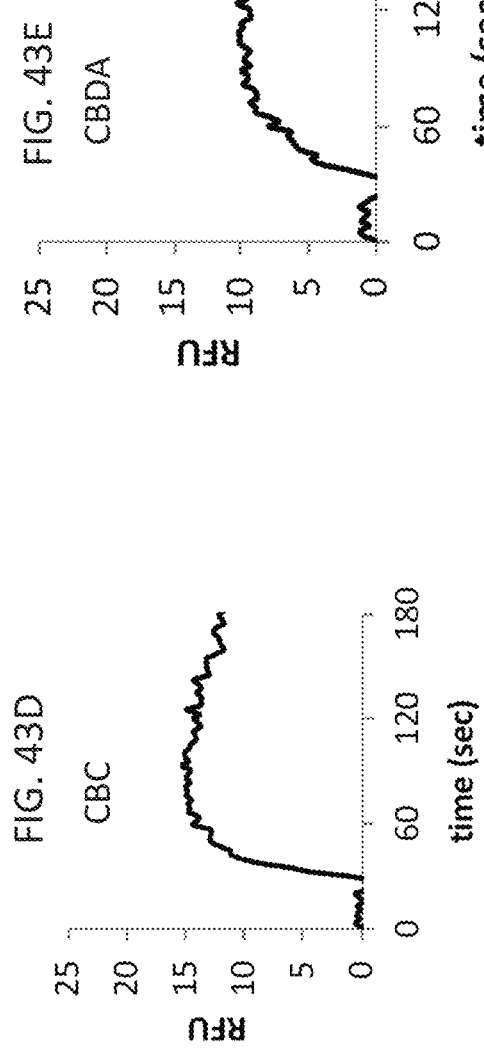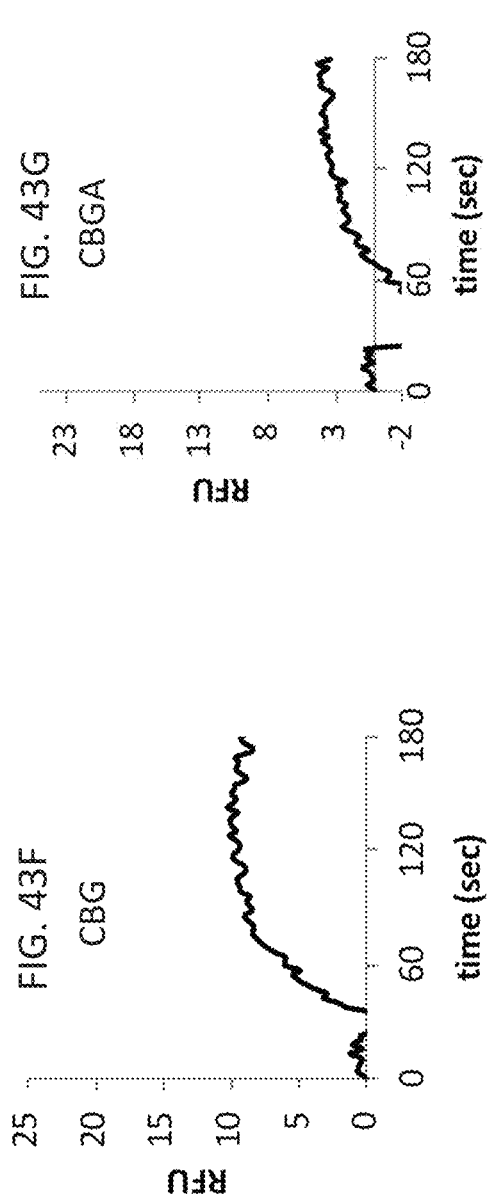

TRPV1 ACTIVATION-MODULATING COMPLEX MIXTURES OF CANNABINOIDS AND/OR TERPENES

CROSS REFERENCE TO RELATED APPLICATIONS

This application claims the benefits of U.S. Provisional Application No. 62/674,843 filed on May 22, 2018, No. 62/769,743 filed on Nov. 20, 2018, and No. 62/849,719 filed on May 17, 2019. The contents of these applications are each incorporated herein by reference.

BACKGROUND

Channels of the Transient Receptor Superfamily (TRP), such as TRPV1, TRPM8 and TRPA1, are non-selective cation channels that conduct calcium and sodium into a range of cell types in mammals. They are present on sensory neurons, and were initially identified as having a role in nociception because of their responsiveness at the molecular level to plant secondary metabolites that are nociomimetic (e.g., capsaicin) and to compounds that are otherwise pungent and mimic burning or cooling sensations (e.g., allicin, cinnamaldehyde, menthol).

The TRPV1 ion channel is known to be involved in certain types of pain, and is the molecular target for capsaicin-based topical analgesics. It has also been implicated in cardiac hypertrophy, and methods have been described for treating cardiac hypertrophy by administration of TRPV1 agonists such as capsaicin and antagonists such as BCTC and capsazepine. See U.S. Pat. No. 9,084,786.

There exists a need to find new compounds that modulate TRPV1 activation and deactivation. Such new compounds would provide novel and more effective ways of treating various diseases associated with the TRPV1 channel, including chronic inflammatory pain conditions, peripheral neuropathy, cardiovascular diseases, urinary cystitis, asthma, and hearing loss.

SUMMARY OF THE INVENTION

Provided herein are methods of modulating the activation of the TRPV1 ion channel by administering at least one cannabinoid or terpene compound.

In one aspect, provided herein are methods of modulating TRPV1 channel permeability, the method comprising externally contacting a TRPV1-expressing cell with at least one compound having a predetermined TRPV1 state-related agonist property. In some embodiments, the method further comprises an earlier step of selecting at least one compound that has the predetermined TRPV1 state-related agonist property. In one embodiment, the ability to modulate TRPV1 with different agonists over a prescribed time course including a pre-treatment, primary treatment, and/or a secondary treatment with or without a wash-out period between treatments may be therapeutically optimized. In various embodiments, the at least one compound is a plurality of compounds, each of the plurality of compounds having different TRPV1 state-related agonist properties.

In some embodiments, the predetermined property is ion selectivity. In one embodiment, the ion selectivity is relative permeation of $Na^+$ and $Ca^{2+}$ ions. In one embodiment, the ion selectivity is the magnitude of $Ca^{2+}$ influx. In one embodiment, the ion selectivity is $Na^+$ selectivity. In one embodiment, the ion selectivity is $Ca^{2+}$ selectivity. In one embodiment, the predetermined property is a pore dilation state. In one embodiment, the predetermined property is a TRPV1 channel activation profile. In another embodiment, the predetermined property is a TRPV1 channel inactivation profile. In one embodiment, the predetermined property is a magnitude of a TRPV1-induced ion current. In one embodiment, the predetermined property is TRPV1 channel activation kinetics. In one embodiment, the predetermined property is TRPV1 channel inactivation kinetics. In one embodiment, the predetermined property is calcium-dependent inactivation. In one embodiment, the predetermined property is calcium-independent inactivation.

In various embodiments, at least one of the at least one compound is a cannabinoid. In one embodiment, the cannabinoid is cannabinol (CBN). In another embodiment, the cannabinoid is cannabidiol (CBD). In one embodiment, the cannabinoid is cannabigerol (CBG). In one embodiment, wherein the cannabinoid is cannabidivarin (CBDV).

In various embodiments, at least one of the at least one compound is a terpene. In one embodiment, the terpene is myrcene. In one embodiment, the terpene is limonene. In one embodiment, the terpene is linalool. In one embodiment, the terpene is phytol. In one embodiment, the terpene is nerolidol. In one embodiment, the terpene is pinene.

In various embodiments, contacting the cell kills the contacted cell. In some embodiments, contacting the cell does not kill the contacted cell. In various embodiments, the contacting is performed in vivo.

In various embodiments, contacting a cell with a TRPV1 state-related agonist induces calcium-dependent cellular signaling pathways. In one embodiment, the signaling pathway results in secretion of secondary mediators. In one embodiment, the signaling pathway results in enzyme activation. In some embodiments, the signaling pathway results in gene expression. In one embodiment, the signaling pathway results in gene regulation. In one embodiment, the signaling pathway results in cellular growth. In one embodiment, the signaling pathway results in cellular death. In one embodiment, the signaling pathway results in cellular replication. In one embodiment, the signaling pathway results in cellular motility.

In another aspect provided herein, the at least one compound is formulated in a pharmaceutical composition, and the method further comprises administering the pharmaceutical composition to a subject in need thereof. In some embodiments, the subject has TRPV1-mediated pain. In other embodiments, the subject has TRPV1-mediated cardiac hypertrophy. In another embodiment, the subject has TRPV1-mediated asthma. In another embodiment, the subject has TRPV1-mediated hearing loss. In another embodiment, the subject has TRPV1-mediated urinary cystitis. In another embodiment, the subject has TRPV1-mediated asthma. In another embodiment, the subject has TRPV1-mediated hearing loss. In another embodiment, the subject has TRPV1-mediated urinary cystitis.

In another aspect, provided herein are methods of treating pain, comprising administering to a subject with pain an effective amount of a pharmaceutical composition comprising at least one compound having a predetermined TRPV1 state-related agonist property, wherein the at least one compound externally contacts a TRPV1-expressing cell that contributes to the subject's sensation of pain.

In another aspect, provided herein are methods of treating cardiac hypertrophy, comprising systemically administering to a subject with cardiac hypertrophy an effective amount of a pharmaceutical composition comprising at least one compound having a predetermined TRPV1 state-related agonist property, wherein the at least one compound externally contacts a TRPV1-expressing cardiac cell.

In another aspect, provided herein are methods of treating asthma, comprising systemically administering to a subject with asthma an effective amount of a pharmaceutical composition comprising at least one compound having a predetermined TRPV1 state-related agonist property, wherein the at least one compound externally contacts a TRPV1-expressing sensory neuron cell. In various embodiments, the sensory neuron innervates a smooth muscle cell, a blood vessel, a trachea, a bronchi, or an alveoli.

In another aspect, provided herein are methods of treating hearing loss related to treatment with an anti-tumor drug, comprising systemically administering to a subject with hearing loss an effective amount of a pharmaceutical composition comprising at least one compound having a predetermined TRPV1 state-related agonist property, wherein the at least one compound externally contacts a TRPV1-expressing sensory neuron. In one embodiment, the anti-tumor drug is cisplatin. In one embodiment, the sensory neuron is in an organ of Corti. In another embodiment, the sensory neuron is in a spiral ganglion cell of an inner ear.

In another aspect, provided herein are methods of treating urinary cystitis, comprising systemically administering to a subject with urinary cystitis an effective amount of a pharmaceutical composition comprising at least one compound having a predetermined TRPV1 state-related agonist property, wherein the at least one compound externally contacts a TRPV1-expressing sensory neuron innervating a urinary bladder or urethra.

BRIEF DESCRIPTION OF THE DRAWINGS

These and other features, aspects, and advantages of the present invention will become better understood with regard to the following description, and accompanying drawings, where:

FIG. 1B, curves 1 and 2), but over time the IV relationship becomes linearized, indicating the channel transitioned into the open pore-dilated state (state 2; FIG. 1B curve 3).

FIGS. 3A-3D show activation of TRPV1 after incubation with control buffer, 50 µM cannabidiol (CBD), or 1 µM capsaicin (Cap). FIG. 3A shows current measurements taken at each discrete data point. FIGS. 3B-3D show the current-voltage relationships (IV) for the three incubations. Each IV curve was selected to illustrate TRPV1 channel selectivity. The control (FIG. 3B) and CBD (FIG. 3C) IV curves are outwardly-rectifying and reverse at slightly negative potentials (state 1). By contrast, the IV curve for capsaicin is linearized and reversed close to zero mV due to the transition to a TRPV1 pore-dilated state (state 2, FIG. 3D).

FIGS. 4A-4D show activation of TRPV1 after incubation with control buffer, 50 µM cannabinol (CBN), or 1 µM capsaicin (Cap). FIG. 4A shows current measurements taken at each discrete data point. FIGS. 4B-4C show the three sets of IV relationships plotted from selected data points for control, CBN and capsaicin. The control (FIG. 4B) and CBN (FIG. 4C) IV curves show an outwardly-rectifying relationship, with the inward current smaller than the outward current. By contrast, the linearized IV curve following capsaicin application (FIG. 4D) shows that the inward current amplitude is close to the outward current amplitude.

FIGS. 5A-5D show that incubation with 10 µM CBN results in partial state transition from state 1 to state 2. The capsaicin stimulus shows a linear IV curve which is indicative of a dilated channel state 2.

FIGS. 6A-6D show activation of TRPV1 after incubation with control buffer, 50 µM cannabidivarin (CBDV), or 1 µM capsaicin (Cap). FIG. 6A shows current measurements taken at each discrete data point. FIGS. 6B-6C show the three sets of IV relationships plotted from selected data points for control, CBDV and capsaicin. The control (FIG. 6B) and CBDV (FIG. 6C) illustrate state 1 of the TRPV1 channel. In contrast, the capsaicin converts the IV into a linear relationship between the inward and outward current (FIG. 6D).

FIG. 7A shows current measurements taken at each discrete data point. FIGS. 7B-7C show the three sets of IV relationships plotted from selected data points for control, CBG and capsaicin. The control (FIG. 7B) and CBG (FIG. 7C) illustrate state 1 of the TRPV1 channel. In contrast, the capsaicin converts the IV into a linear relationship between the inward and outward current (FIG. 7D).

FIG. 8A shows current measurements at discrete data points after exposure to 5 µM myrcene, FIG. 8B shows current measurements at discrete data points after exposure to 10 µM myrcene, and FIG. 8C shows current measurements at discrete data points after exposure to 150 µM myrcene.

FIGS. 9A-9E illustrate activation of TRPV1 after incubation with 5 µM myrcene (M) and 1 µM capsaicin (Cap). FIGS. 9A and 9B show the inward and outward ion current (nA) of the cell before and after myrcene and capsaicin addition. FIG. 9B is an enlarged view of FIG. 9A to further show the myrcene-induced response. FIGS. 9C-9E show the current/voltage relationship curve of the cell before myrcene or capsaicin is added (FIG. 9C), or after 5 µM myrcene (FIG. 9D) or 1 µM capsaicin (FIG. 9E).

FIGS. 10A-10D show activation of TRPV1 following incubation with control buffer, 50 µM myrcene, and 1 µM capsaicin. FIG. 10A shows current measurements taken at each discrete data point. FIGS. 10B-10C show the three sets of IV relationships plotted from selected data points for control, myrcene, and capsaicin. The control (FIG. 10B) and myrcene (FIG. 10C) illustrate state 1 of the TRPV1 channel. In contrast, the capsaicin converts the IV into a linear relationship between the inward and outward current (FIG. 10D).

FIGS. 11A-11C show activation of TRPV1 following incubation with control buffer, 150 µM myrcene, and 1 µM capsaicin. FIG. 11A shows current measurements taken at each discrete data point. FIGS. 11B-11C show the three sets of IV relationships plotted from selected data points for control, myrcene, and capsaicin. The control (FIG. 11B) and myrcene (FIG. 11C) illustrate state 1 of the TRPV1 channel.

In contrast, the capsaicin converts the IV into a linear relationship between the inward and outward current (FIG. 11D)

FIGS. 12A-12I show a $Ca^{2+}$ dose-dependent inactivation of TRPV1. FIG. 12A shows the current development graph at 0 mM internal calcium with external incubation of 10 μM myrcene and the subsequent application of 1 μM capsaicin. FIG. 12B shows the extracted current/voltage relationship after external incubation of 10 μM myrcene and FIG. 12C shows the extracted current/voltage relationship after application of 1 μM capsaicin. FIG. 12D shows the current development graph at 180 mM internal calcium with external incubation of 10 μM myrcene and the subsequent application of 1 μM capsaicin. FIG. 12E shows the extracted current/voltage relationship after external incubation of 10 μM myrcene and FIG. 12F shows the extracted current/voltage relationship after application of 1 μM capsaicin. FIG. 12G shows the current development graph at 620 mM internal calcium with external incubation of 10 μM myrcene and the subsequent application of 1 μM capsaicin. FIG. 12H shows the extracted current/voltage relationship after external incubation of 10 μM myrcene and FIG. 12I shows the extracted current/voltage relationship after application of 1 μM capsaicin. Increasing concentrations of internal (cytosol) calcium (0, 180 nM, and 620 nM) reduce the TRPV1 current peak amplitude activated by external incubation of 10 μM myrcene and the subsequent application of 1 μM capsaicin. In addition, increasing levels of internal calcium shows a minor effect on the falling phase or inactivation kinetics from myrcene but a stronger effect on inactivation induced by capsaicin.

Figure 13A:
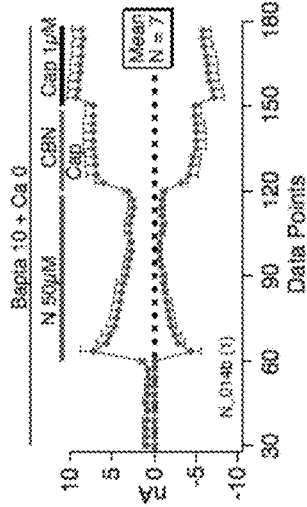
Figure 13B:
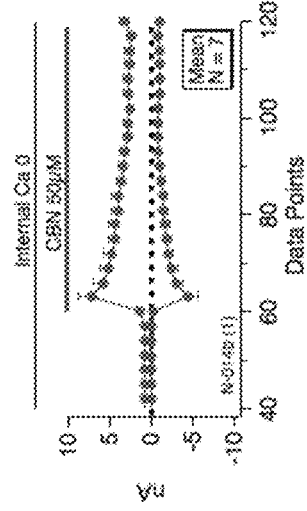
Figure 13C:
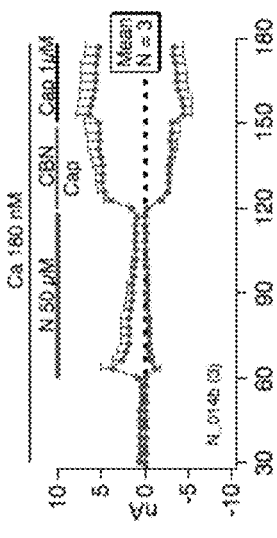
Figure 13D:
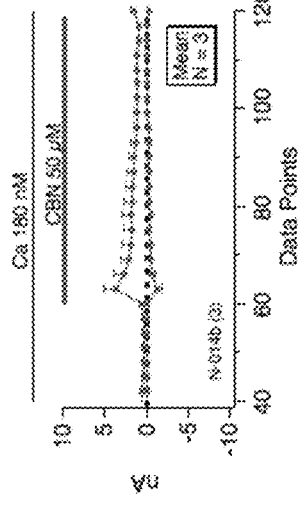
Figure 13E:
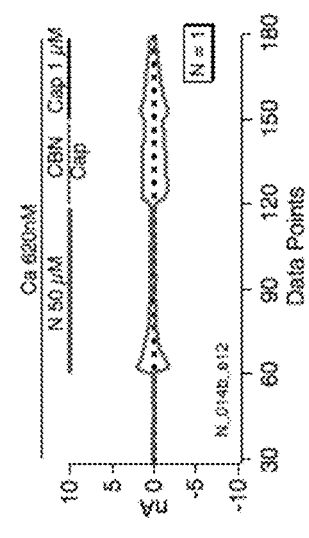
Figure 13F:
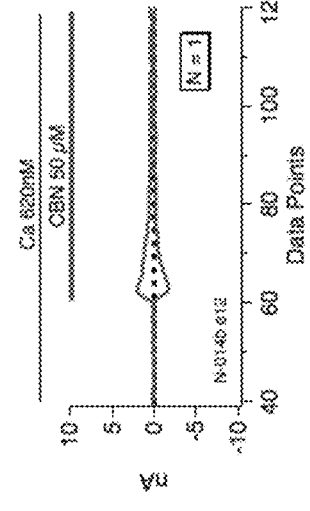

FIGS. 13A-13F show a $Ca^{2+}$ dose-dependent inactivation of TRPV1. FIG. 13A shows the current development graph at 0 mM internal calcium with external incubation of 50 μM FIG. 13B shows the current development graph at 0 mM internal calcium with external incubation of 50 μM CBN alone, 50 μM CBN and 1 μM capsaicin, and 1 μM capsaicin alone. FIG. 13C shows the current development graph at 180 mM internal calcium with external incubation of 50 μM CBN. FIG. 13D shows the current development graph at 180 mM internal calcium with external incubation of 50 μM CBN alone, 50 μM CBN and 1 μM capsaicin, and 1 μM capsaicin alone. FIG. 13E shows the current development graph at 620 mM internal calcium with external incubation of 50 μM CBN. FIG. 13F shows the current development graph at 620 mM internal calcium with external incubation of 50 μm CBN alone, 50 μM CBN and 1 μM capsaicin, and 1 μM capsaicin alone. Increasing concentrations of internal (cytosol) calcium (0, 180 nM, and 620 nM) reduce the TRPV1 current peak amplitude activated by external incubation of 50 μM CBN alone, 50 μM CBN and 1 μM capsaicin, and 1 μM capsaicin alone. The results are similar to FIGS. 12A-12I. The CBN reduced the peak current amplitude but did not have a strong effect on the inactivation or falling phase kinetics. In comparison to the mixture of CBN and capsaicin, internal 0 nM $Ca^{2+}$ removed the falling phase kinetics or inactivation. By contrast, the high internal $Ca^{2+}$ at 620 nM showed a significant reduction on current amplitude and acceleration of inactivation kinetics.

Figure 14:
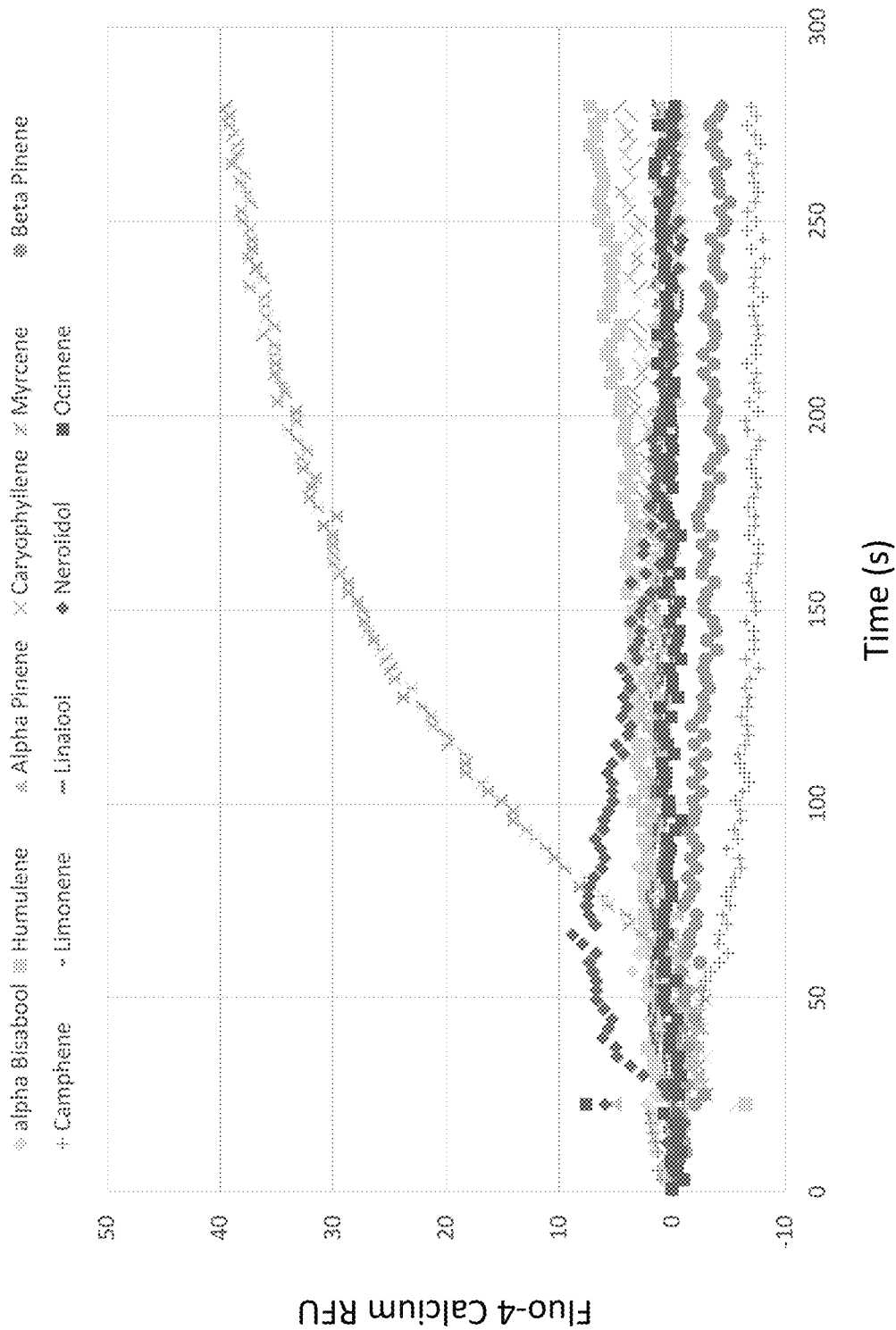

FIG. 14 shows the TRPV1-mediated calcium entry in an HEK-TRPV1 cell line after treatment with 10 μM of alpha-bisabool, alpha-pinene, myrcene, camphene, linalool, ocimene, humulene, beta-caryophyllene, beta-pinene, limonene, or nerolidol.

FIGS. 15A-D show the effect of 10 μM myrcene on TRPA1 (FIG. 15A), TRPM8 (FIG. 15B), TRPV1 (FIG. 15C), or TRPV2 (FIG. 15D) in a calcium entry assay.

FIGS. 16A-H show the initiation of a calcium flux in HEK-TRPV1 overexpressing cells by cannabidiol (FIG. 16A), cannabinol (FIG. 16B), cannabividarin (FIG. 16C), cannabidigerol (FIG. 16D), cannabigerolic acid (FIG. 16E), cannabichromene (FIG. 16F), cannabidiolic acid (FIG. 16G), and capsaicin (FIG. 16H) respectively. Cannabigerol and cannabinol did not initiate a calcium flux.

FIGS. 17A-D show sensitivity of capsaicin- and cannabinoid-induced conductances to Capsazepine (CPZ). FIG. 17A shows the current development graph and FIG. 17B provides the extracted current/voltage relationship, respectively, in HEK-TRVP1 stimulated with 50 nM Capsaicin followed by application of 10 μM of CPZ. FIG. 17C shows the current development graph and FIG. 17D provides the extract current/voltage relations, respectively, in HEK-TRVP1 stimulated with 30 μM of cannabidiol (CBD). The recording solution were Ca 0 internally and externally and the n determinations were form 5-6 patches. The current development graphs of FIGS. 17A and 17C were generated by extracting currents at the voltages of −80 mV and +80 mV.

Figure 18C:
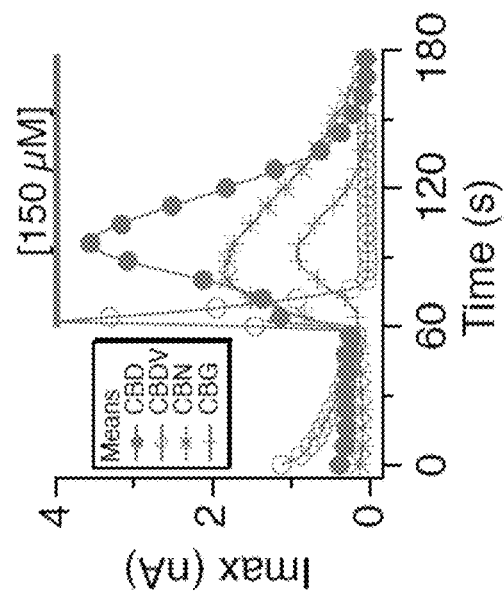
Figure 18B:
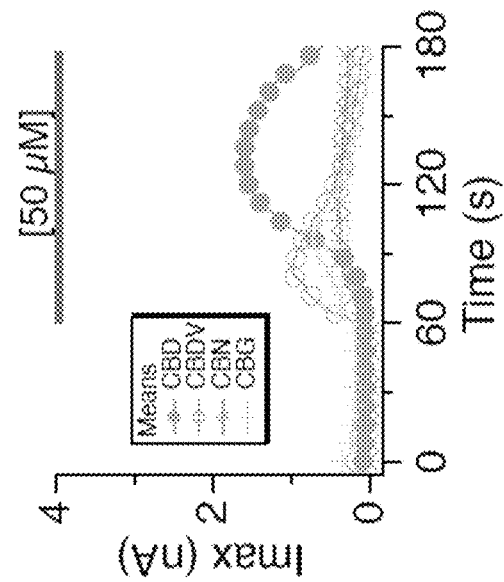
Figure 18A:
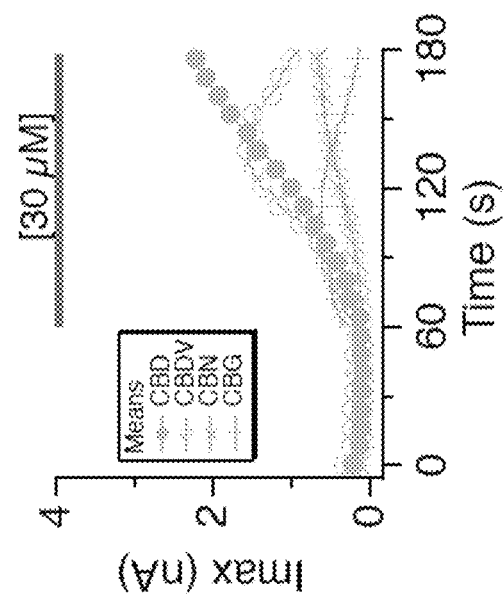
Figure 21A:
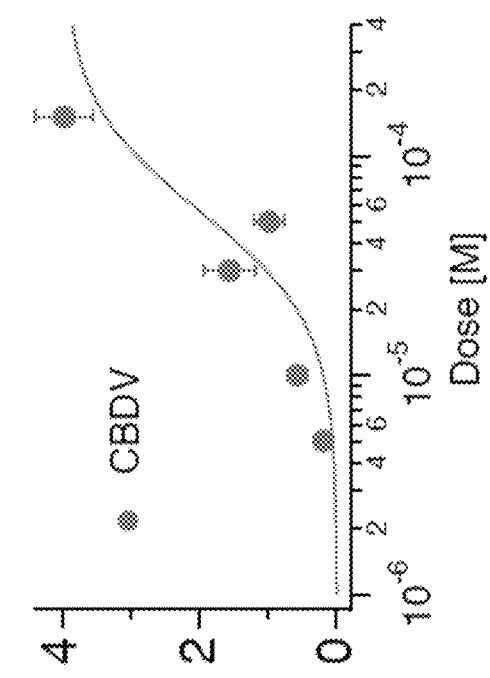
Figure 21B:
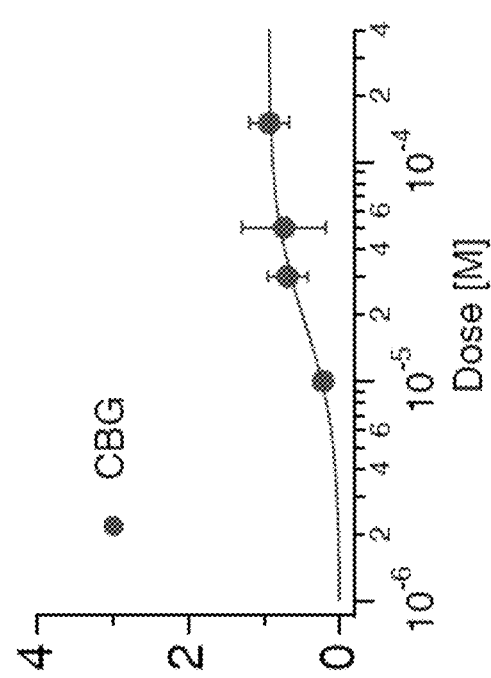
Figure 21C:
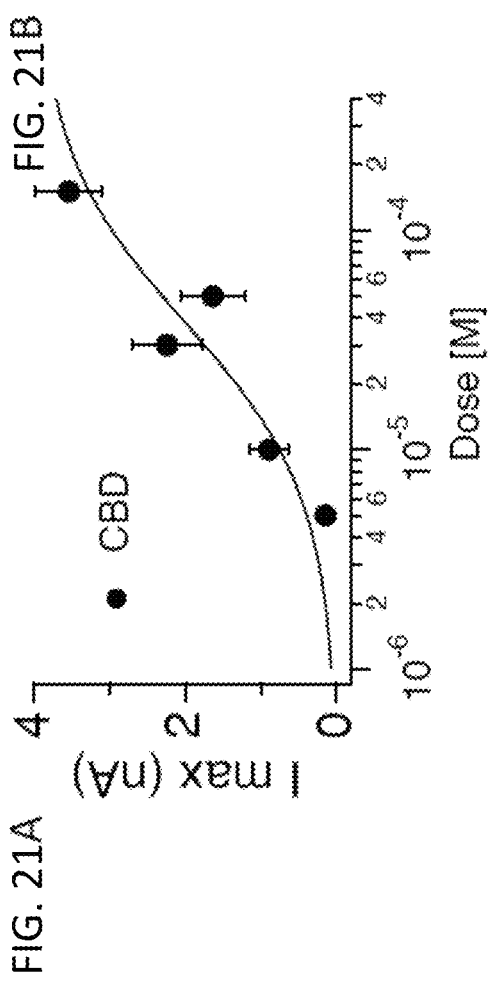
Figure 21D:
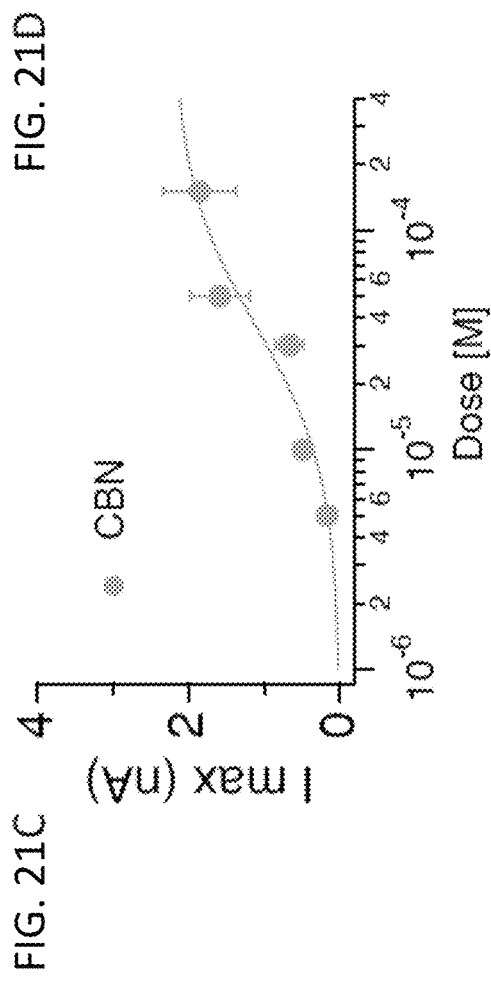

FIGS. 18A-C show current development graphs for HEK-TRPV1 exposed for 120 seconds at various doses of CBD (closed circle), CBDV (open circle), CBN (asterisk), and CBG (cross). FIG. 18A shows results from dosing individual cannabinoids at 30 μM. FIG. 18B shows the results from dosing individual cannabinoids at 50 μM. FIG. 18C shows the results from dosing individual cannabinoids at 150 μM.

FIGS. 19A-L show the individual current development graphs of HEK-TRPV1 exposed for 120 seconds at various doses of CBD, CBDV, CBN, and CBG. FIG. 19A-C show current development graphs of HEK-TRVP1 dosed with CBD at 30 μM (FIG. 19A), 50 μM (FIG. 19B), and 150 μM (FIG. 19C) respectively. FIG. 19D-F show current development graphs of HEK-TRVP1 dosed with CBDV at 30 μM (FIG. 19D), 50 μM (FIG. 19E), and 150 μM (FIG. 19F) respectively. FIG. 19G-I show current development graphs of HEK-TRVP1 dosed with CBN at 30 μM (FIG. 19G), 50 μM (FIG. 19H), and 150 μM (FIG. 19I) respectively. FIG. 19J-L show current development graphs of HEK-TRVP1 dosed with CBG at 30 μM (FIG. 19J), 50 μM (FIG. 19K), and 150 μM (FIG. 19L) respectively.

FIGS. 20A-D show histograms of Imax data from the data shown in FIGS. 20A-L. FIG. 20A shows the Imax data of cannabinoids dosed at 10 μM. FIG. 20B shows the Imax data of cannabinoids dosed at 30 μM. FIG. 20C shows the Imax data of cannabinoids dosed at 50 μM. FIG. 20D shows the Imax data of cannabinoids dosed at 150 μM. Recording conditions were NaR, Ca 1 mM with unbuffered internal calcium (FCa) and the n determinations varied from 5 to 10 patches and as indicated by FIGS. 20A-D.

FIGS. 21A-D show the dose responses and EC50 calculations of CBD (FIG. 21A), CBDV (FIG. 21B), CBN (FIG. 21C), and CBG (FIG. 21D) for TRPV1.

Figure 22:
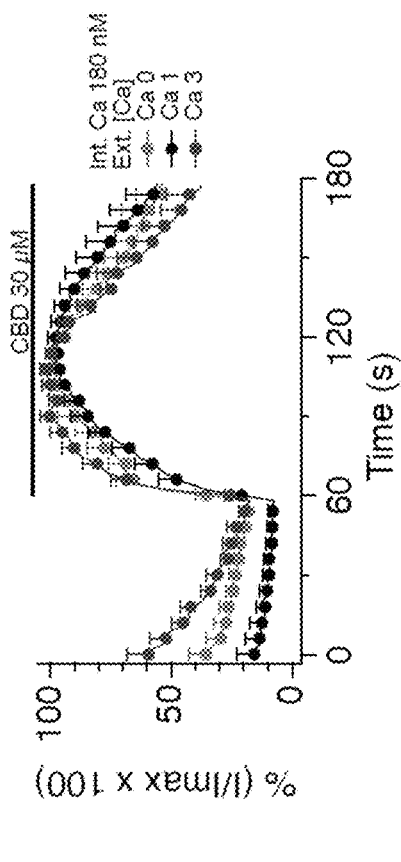
Figure 22:
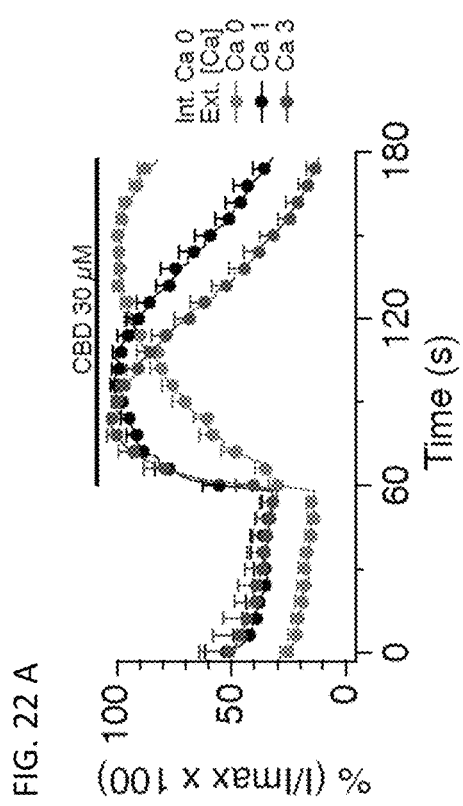
Figure 22:
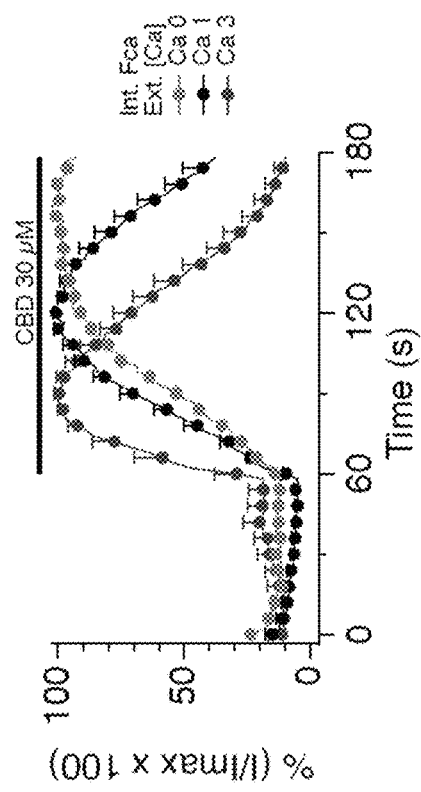
Figure 23:
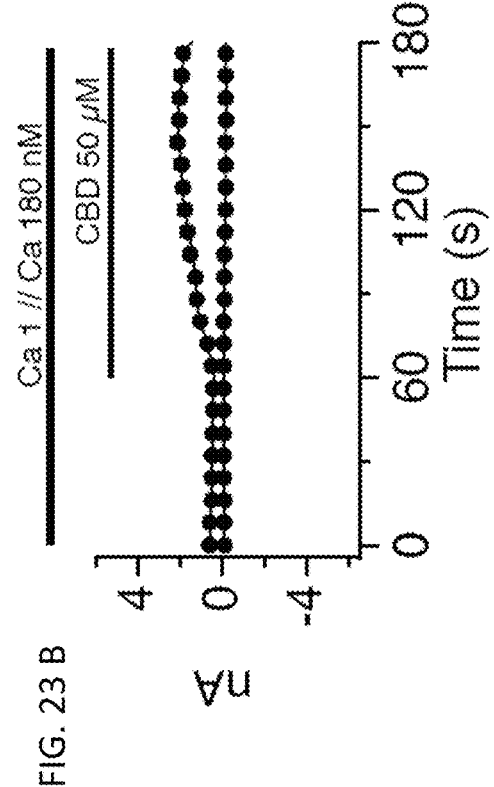
Figure 23:
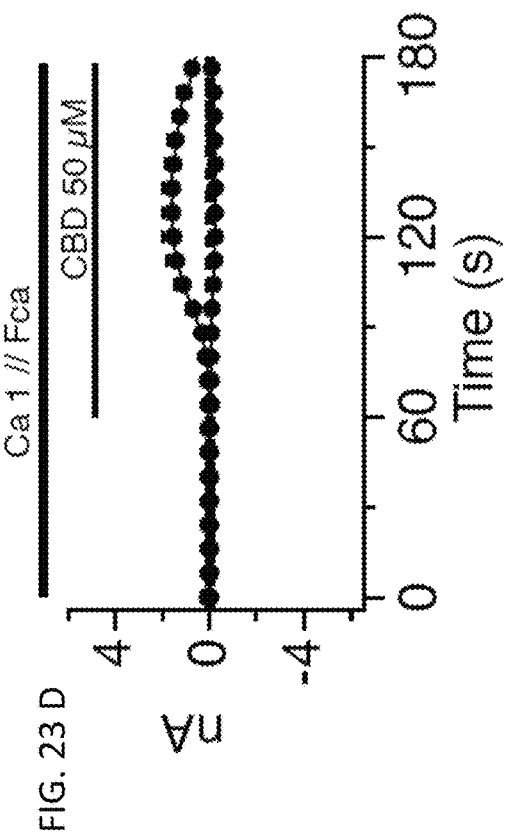
Figure 23:
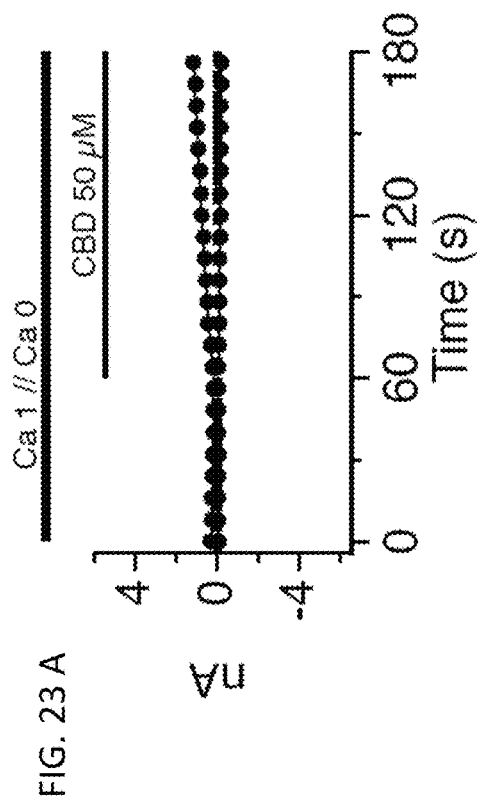
Figure 23:
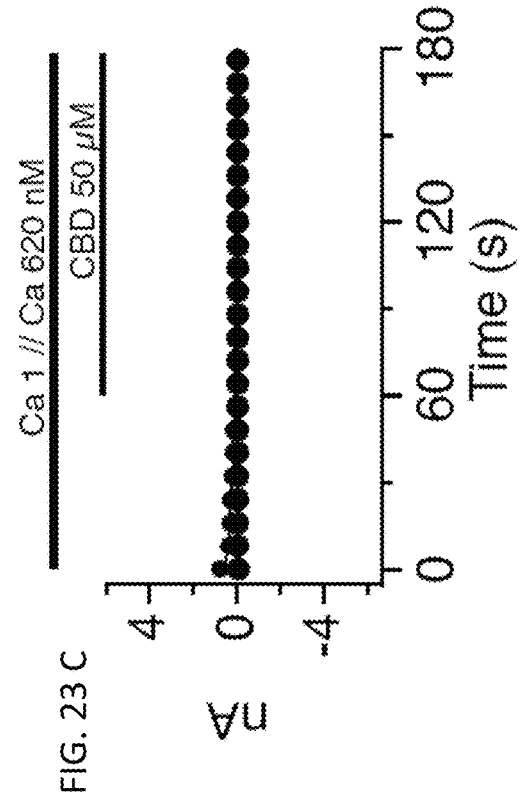

FIGS. 22A-C show the impact of internal and external calcium levels upon CBD-induced TRPV1 currents. Specifically, FIG. 20A-C shows normalized current development graphs (percentage of Imax) for CBD at 30 μM with external calcium concentration of 0 mM (red), 1 mM (black), and 3 mM (blue) and internal calcium concentration buffered to 0 nM (FIG. 22A), 180 nM (FIG. 22B), and as determined by influx (FCa, free calcium) (FIG. 22C), respectively.

FIGS. 23A-D show CBD responses in constant external calcium with varying internal $Ca^{2+}$ concentrations of 0 nM (FIG. 23A), 180 nM (FIG. 23B), 620 nM (FIG. 23C), and FCa (FIG. 23D) respectively.

FIGS. 24A-D show CBN responses in constant external calcium with varying internal $Ca^{2+}$ concentrations of 0 nM (FIG. 24A), 180 nM (FIG. 24B), 620 nM (FIG. 24C), and FCa (FIG. 24D) respectively.

Figure 25:
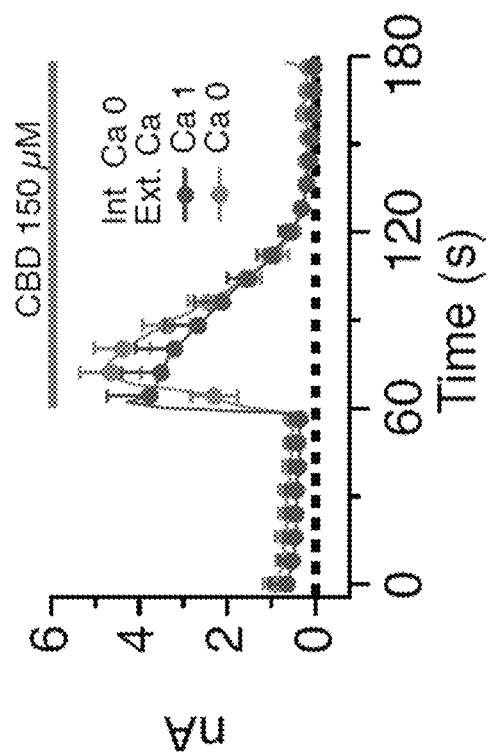
Figure 25:
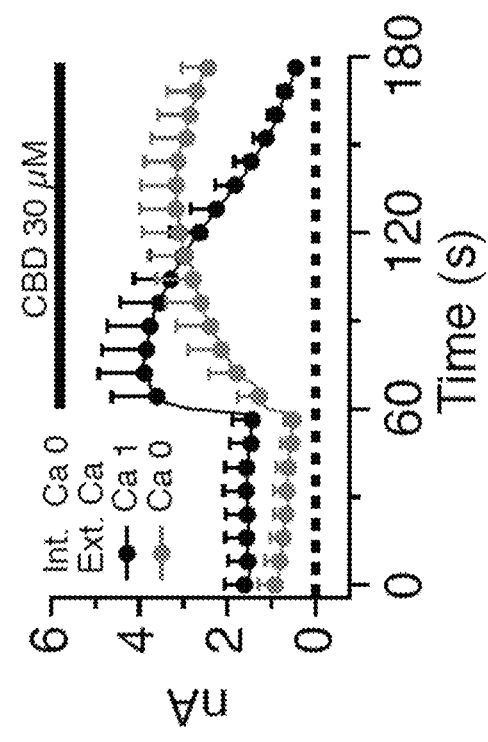

FIGS. 25A-B show the comparison of responses with different CBD concentrations in constant external calcium concentrations and internal $Ca^{2+}$ concentrations of 0 nM. FIG. 25A shows results with CBD concentration of 30 µM. FIG. 25B shows results with CBD concentration of 150 µM.

Figure 26:
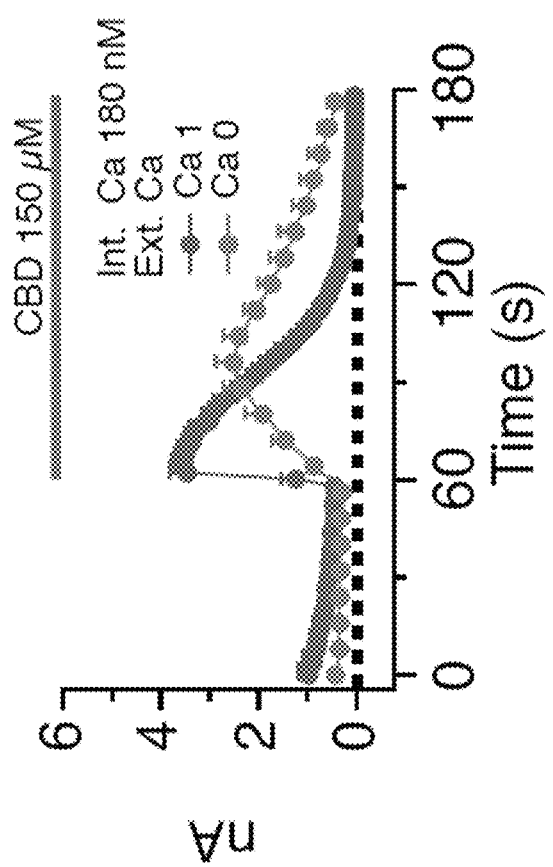
Figure 26:
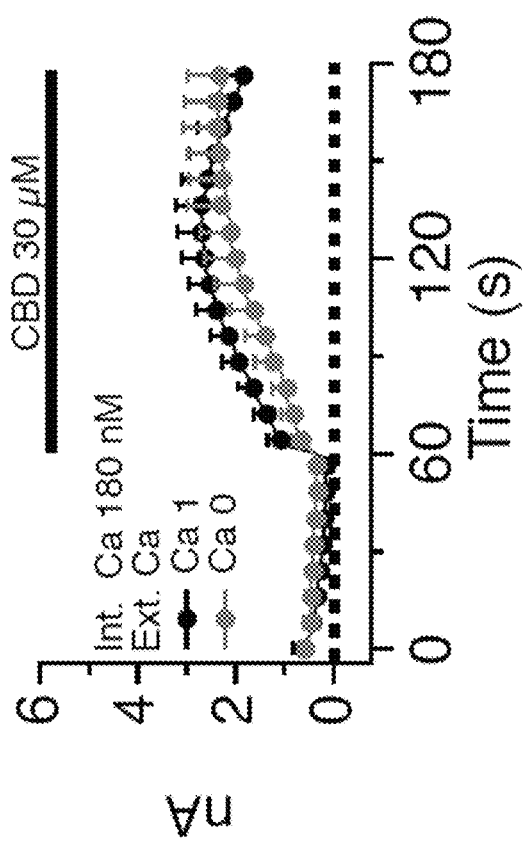

FIGS. 26A-B show the comparison of responses with different CBD concentrations in constant external calcium concentrations and internal $Ca^{2+}$ concentrations of 180 nM. FIG. 26A shows results with CBD concentration of 30 µM. FIG. 26B shows results with CBD concentration of 150 µM.

Figure 27:
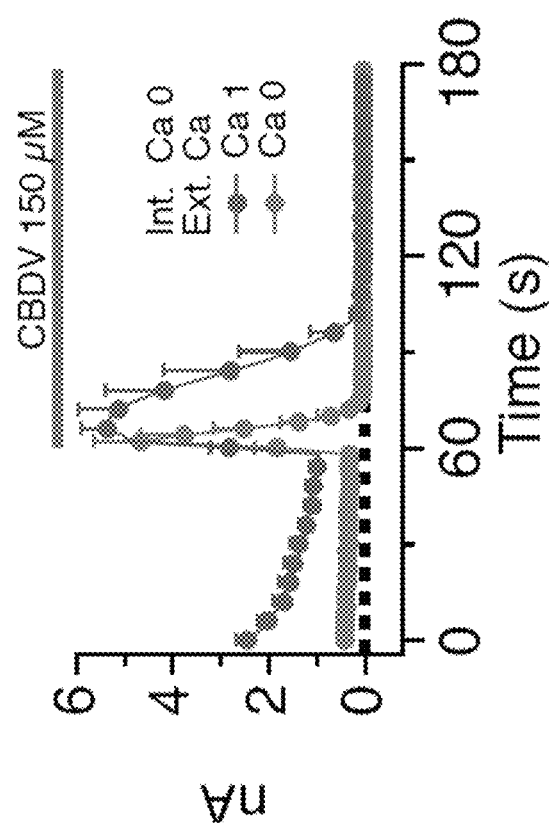
Figure 27:
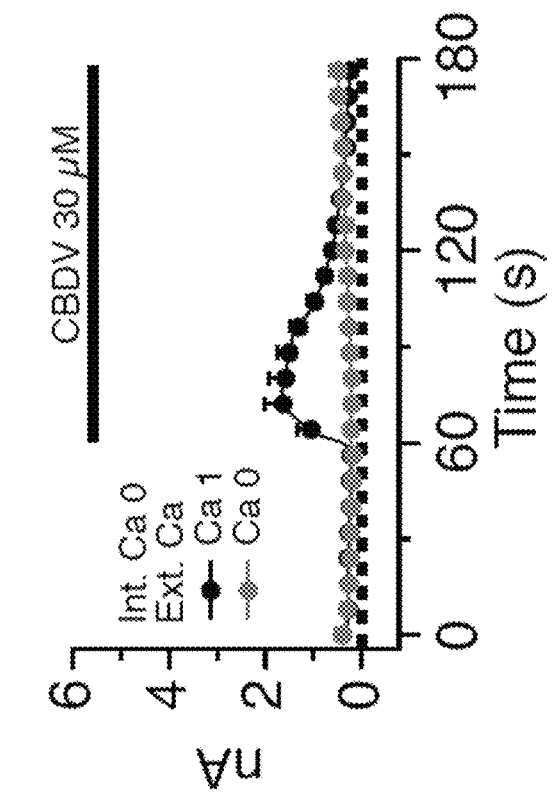

FIGS. 27A-B show the comparison of responses with different CBDV concentrations in constant external calcium concentrations and internal $Ca^{2+}$ concentrations of 0 nM. FIG. 27A shows results with CBDV concentration of 30 µM. FIG. 27B shows results with CBDV concentration of 150 µM.

FIGS. 28A-B show the comparison of responses with different CBDV concentrations in constant external calcium concentrations and internal $Ca^{2+}$ concentrations of 180 nM. FIG. 28A shows results with CBDV concentration of 30 µM. FIG. 28B shows results with CBDV concentration of 150 µM.

Figure 29:
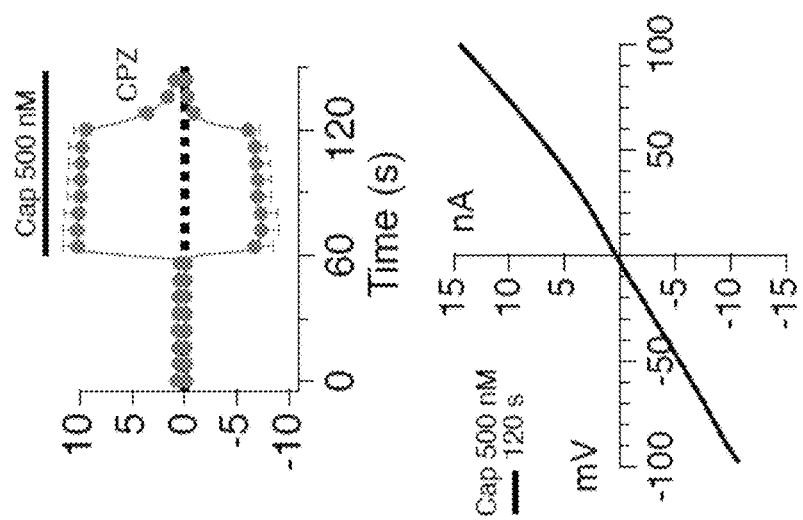
Figure 29:
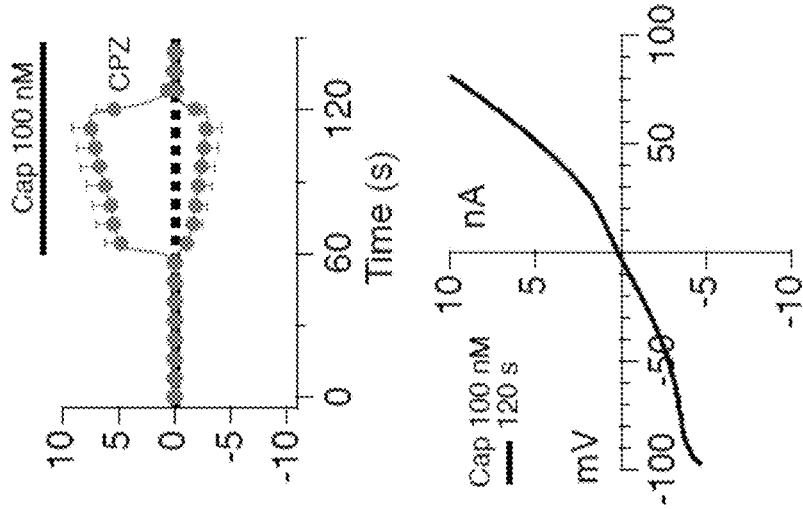
Figure 29:
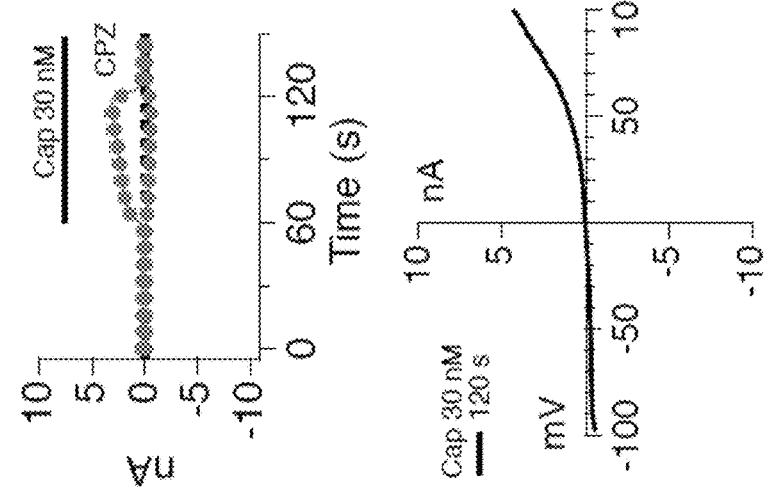

FIGS. 29A-C show dose-dependent attainment of pore-dilated state by TRPV1 in response to Capsaicin. Specifically, FIGS. 29A-C shows the current development graph and extracted I/V curves demonstrating transition from rectifying to non-rectifying state with increasing dose/current amplitude for Capsaicin at concentration of 30 nM (FIG. 29A), 100 nM (FIG. 29B), and 500 nM (FIG. 29C) respectively.

Figure 30:
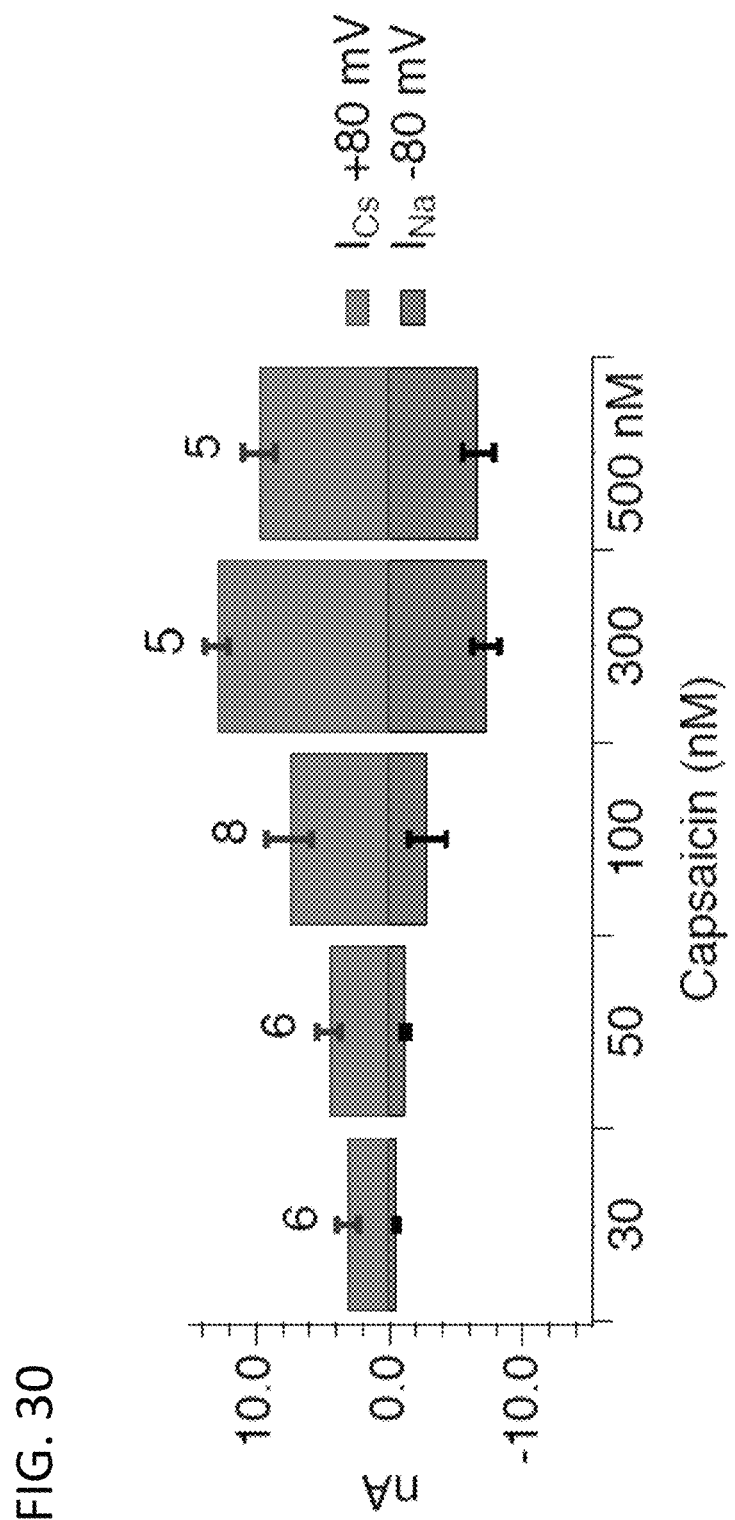

FIG. 30 shows the linearized I/V relationship corresponds to pore-dilated state by demonstrating increased Na current amplitude.

FIGS. 31A-C show current development graphs and extracted current/voltage relationships for Capsaicin at concentrations of 30 nM (FIG. 31A), 100 nM (FIG. 31B), and 500 nM (FIG. 31C) respectively. These figures suggest that some pore-dilation (N-Methyl-D-glucamine permeation) exist even at the lowest Capsaicin dose.

Figure 32C:
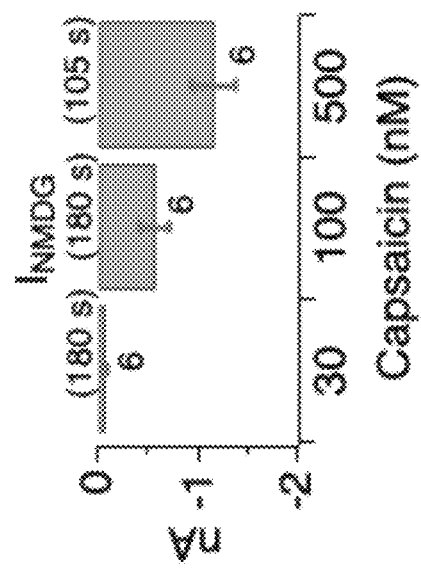
Figure 32B:
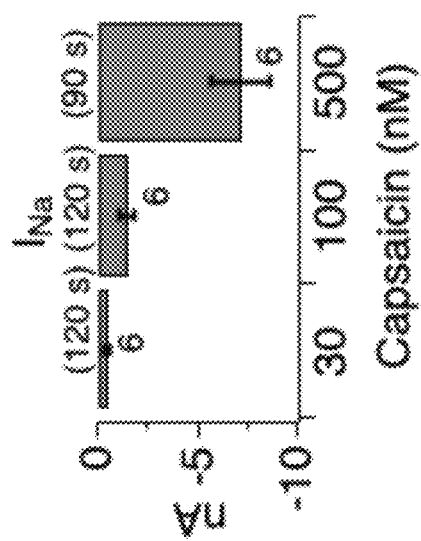
Figure 32A:
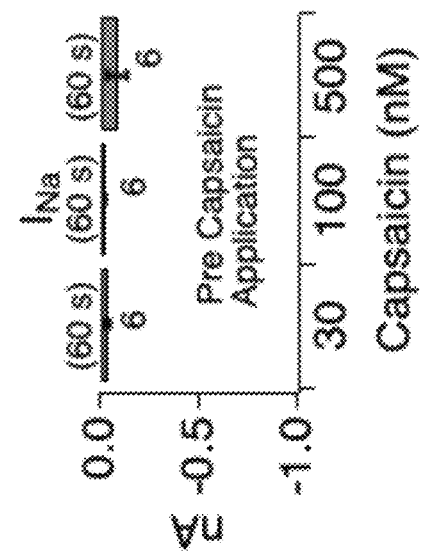
Figure 33A:
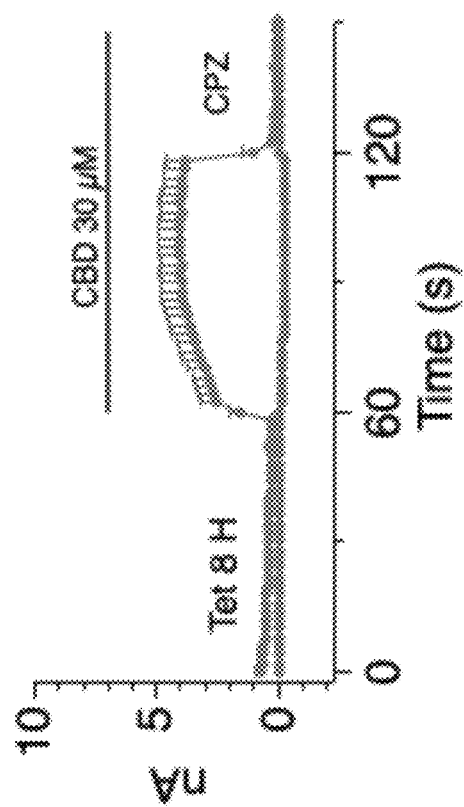
Figure 33B:
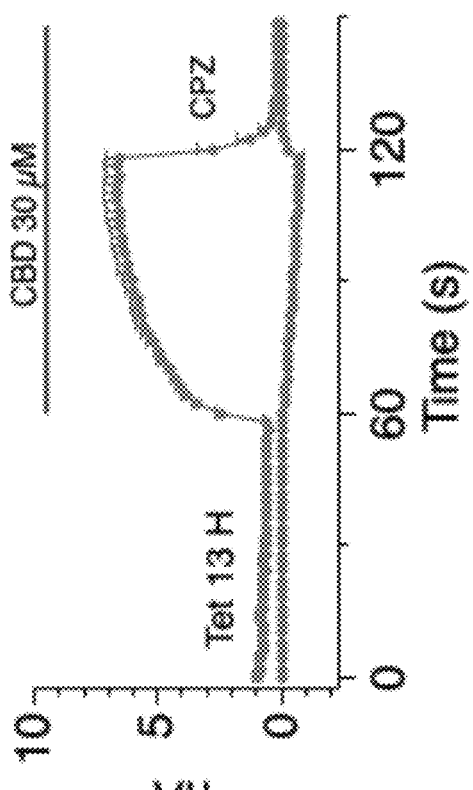
Figure 33C:
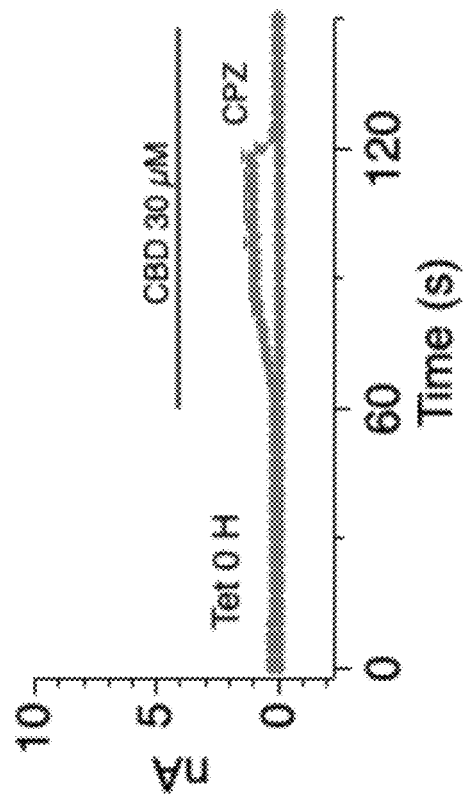
Figure 33D:
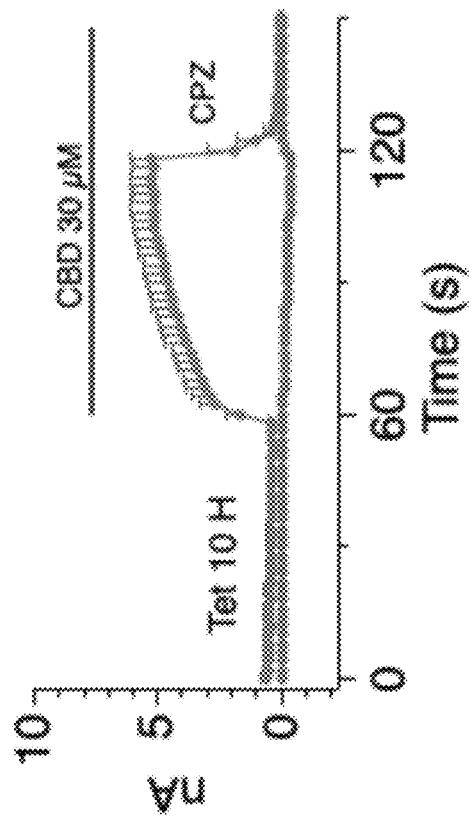

FIGS. 32A-C show the Imax histograms for sodium and N-methyl-D-glucamine (NMDG) permeation in the presence of various concentrations of Capsaicin at different times of 60 seconds (FIG. 32A), 90 and 120 seconds (FIG. 32B), and 105 and 180 seconds (FIG. 32C) respectively, demonstrating that distinct states exist.

FIGS. 33A-D show current development graphs of CBD at 30 µM after various tetracycline induction periods of 0 hours (FIG. 33A), 8 hours (FIG. 33B), 10 hours (FIG. 33C), and 13 hours (FIG. 33D) respectively.

Figure 34:
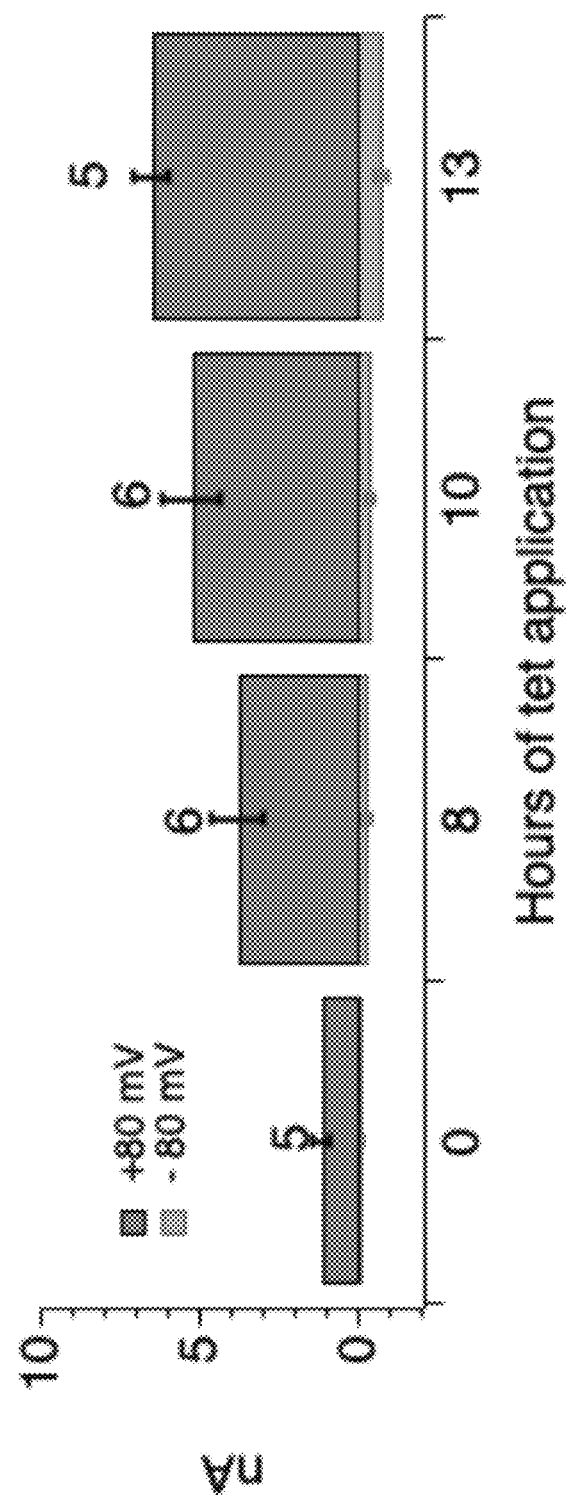

FIG. 34 shows the Imax histograms of the results shown in FIGS. 33A-D.

Figure 35:
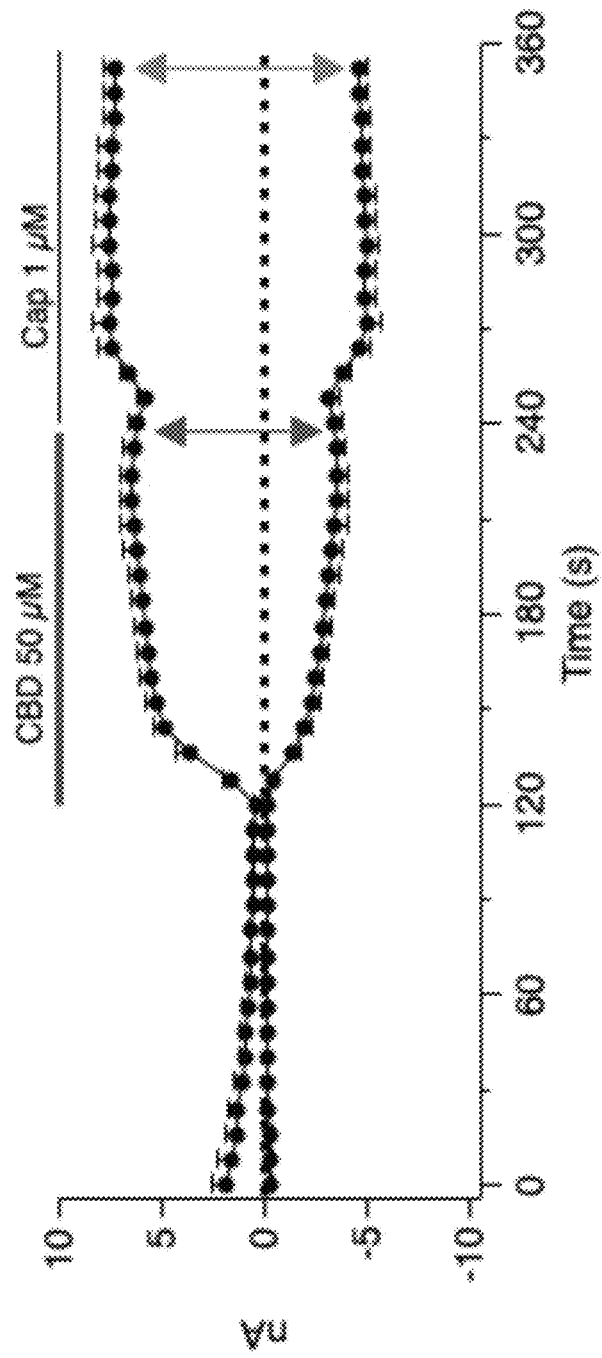

FIG. 35 shows the currents evoked by CBD and Capsaicin at concentrations of 50 µM and 1 µM respectively. An induction time of 25 hours was allowed and CBD was dosed at 50 µM followed by Capsaicin at 1 µM.

Figure 36A:
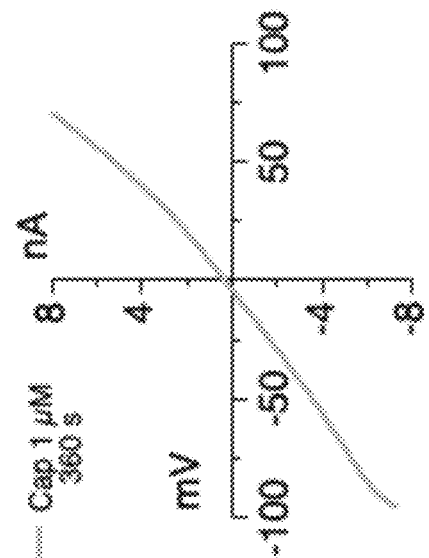
Figure 36B:
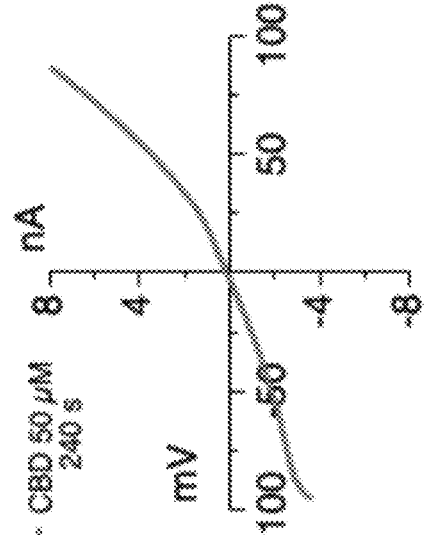
Figure 36C:
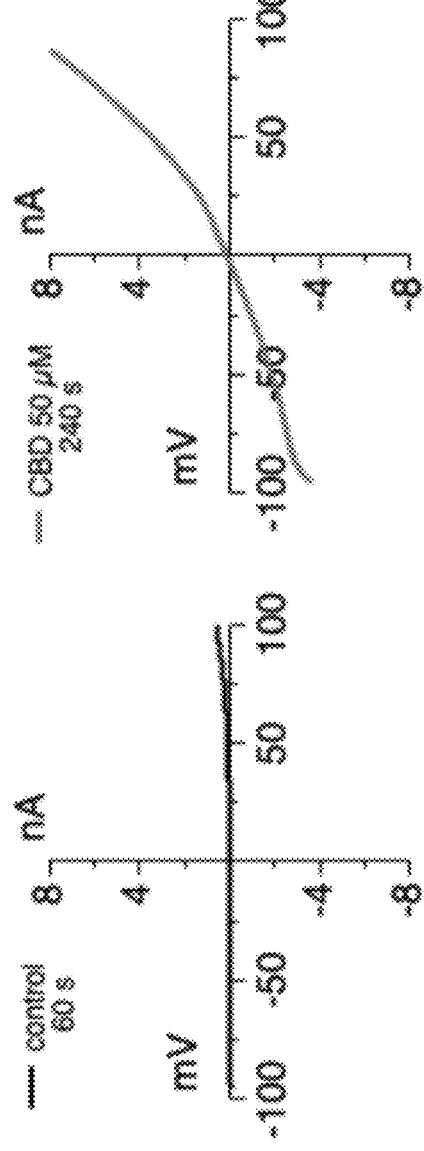

FIGS. 36A-C show the UV relationships of control (FIG. 36A), CBD at 50 µM for 360 seconds (FIG. 36B), and Capsaicin at 1 µM for 360 seconds (FIG. 36C).

Figure 37:
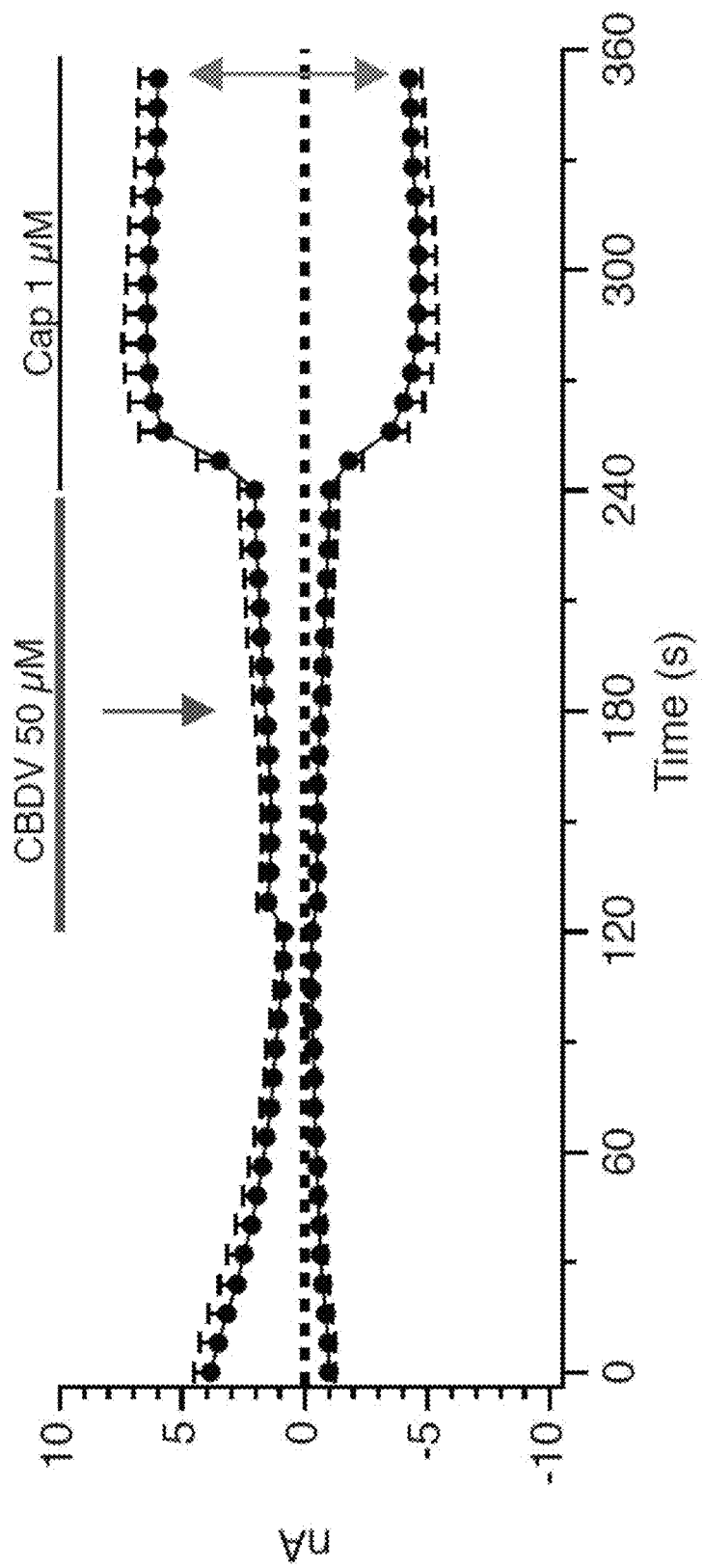

FIG. 37 shows the currents evoked by CBDV and Capsaicin at concentrations of 50 µM and 1 µM respectively. An induction time of 25 hours was allowed, and CBDV was dosed at 50 µM followed by Capsaicin at 1 µM.

Figure 38A:
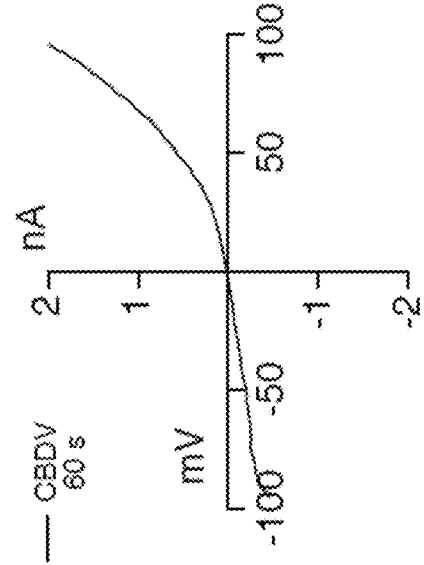
Figure 38B:
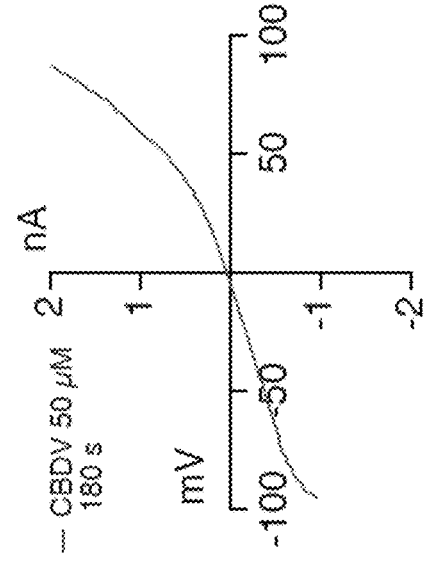
Figure 38C:
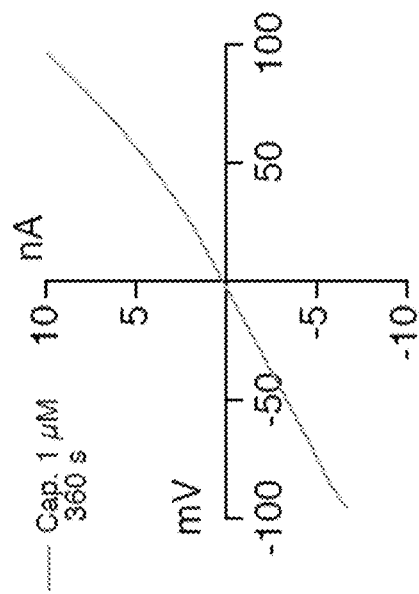

FIGS. 38A-C show the UV relationships of control (FIG. 38A), CBDV at 50 µM for 180 seconds (FIG. 38B), and Capsaicin at 1 µM for 360 seconds (FIG. 38C).

Figure 39:
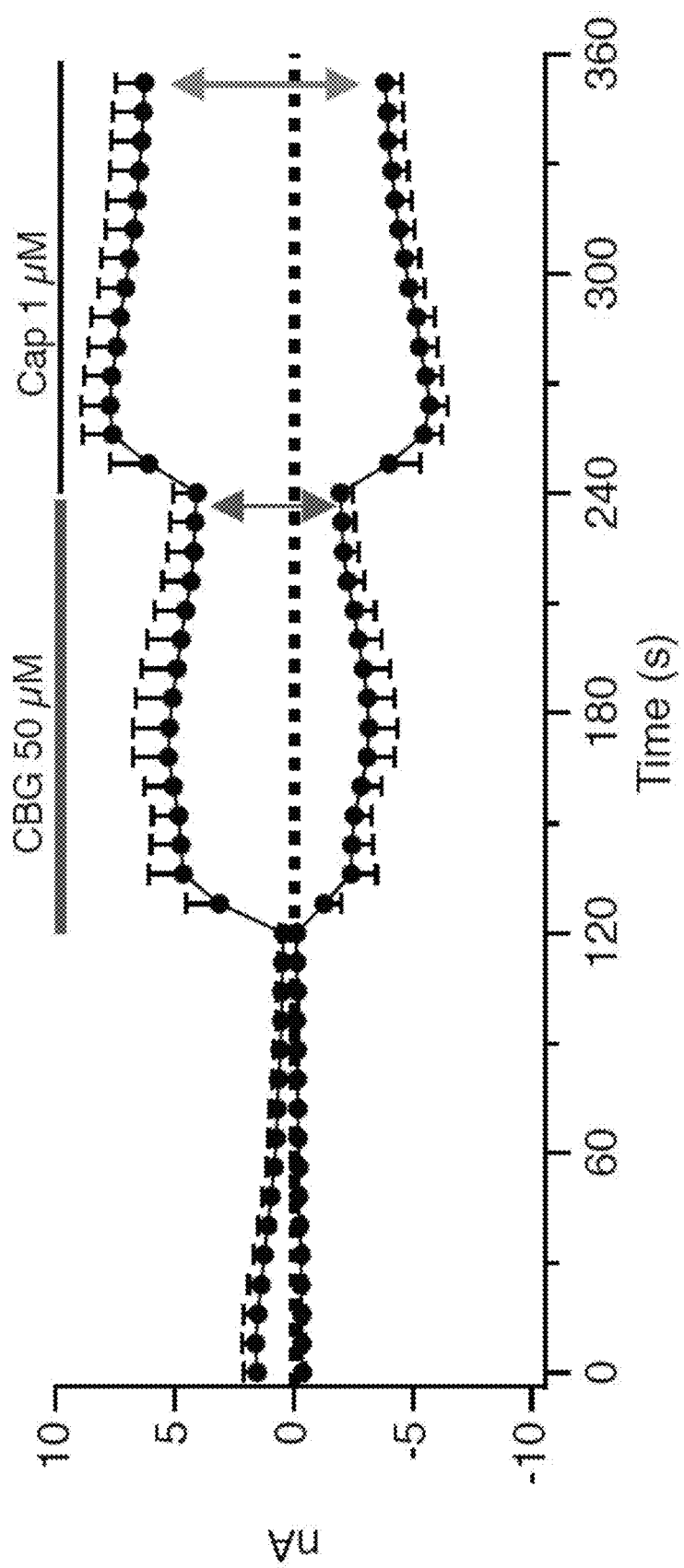

FIG. 39 shows the currents evoked by CBG and Capsaicin at concentrations of 50 µM and 1 µM respectively. An induction time of 25 hours was allowed, and CBG was dosed at 50 µM followed by Capsaicin at 1 µM.

FIGS. 40A-C show the UV relationships of control (FIG. 40A), CBG at 50 µM for 180 seconds (FIG. 40B), and Capsaicin at 1 µM for 360 seconds (FIG. 40C).

FIGS. 41A-G show the responses of a variety of cannabinoids, such as CBD (FIG. 41A), CBN (FIG. 41B), CBDV (FIG. 41C), CBC (FIG. 41D), CBDA (FIG. 41E), CBG (FIG. 41F), and CBGA (FIG. 41G), in cells overexpressing nociceptive TRPV2.

FIG. 42A-G show the responses of a variety of cannabinoids, such as CBD (FIG. 42A), CBN (FIG. 42B), CBDV (FIG. 42C), CBC (FIG. 42D), CBDA (FIG. 42E), CBG (FIG. 42F), and CBGA (FIG. 42G), in cells overexpressing nociceptive TRPM8.

FIG. 43A-G show the responses of a variety of cannabinoids, such as CBD (FIG. 43A), CBN (FIG. 43B), CBDV (FIG. 43C), CBC (FIG. 32D), CBDA (FIG. 32E), CBG (FIG. 32F), and CBGA (FIG. 32G), in cells overexpressing nociceptive TRPA1.

DETAILED DESCRIPTION OF THE INVENTION

Definitions

Terms used in the claims and specification are defined as set forth below unless otherwise specified.

"Myrcene" (synonymously "β-myrcene") is 7-methyl-3-methylideneocta-1,6-diene.

"Terpenes" mean alpha-bisabolol (α-bisabolol), alpha-humulene (αhumulene), alpha-pinene (α-pinene), beta-caryophyllene (β-caryophyllene), myrcene, (+)-beta-pinene (β-pinene), camphene, limonene, linalool, phytol, and nerolidol.

"State-related property" means a chemical or physical property of the open state of the TRPV1 ion channel. Exemplary state-related properties include, but are not limited to, monovalent or divalent ion selectivity or non-selectivity, current rectification profile, ion channel activation profile, ion channel deactivation profile, ion channel activation kinetics, ion channel deactivation kinetics, ion flux, open state selectivity, or the magnitude or amplitude of the TRPV1 ion current.

A "TRPV1 state-related agonist property" of a compound means the ability of the compound to modulate TRPV1 channel permeability by modulating at least one state-related property of the channel, including altering or inducing a change in the TRPV1 channel from one state to another state, or maintaining the channel in a specific non-dilated state without transition to a second state.

"Pharmaceutically active ingredient" (synonymously, active pharmaceutical ingredient) means any substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body. Such substances or mixture of substances are preferably generated in compliance with the Current Good Manufacturing Practice (CGMP) regulations pursuant to Section 501(a)(2)(B) of the Federal Food, Drug, and Cosmetic Act.

A pharmaceutically active ingredient is "substantially free of THC" if the ingredient contains less than 0.3% (w/w) of delta-9 tetrahydrocannabinol. A pharmaceutical composition is "substantially free of THC" if the pharmaceutical composition contains less than 0.3% (w/v) of delta-9 tetrahydrocannabinol.

A "*Cannabis sativa* extract" is a composition obtained from *Cannabis sativa* plant materials by fluid and/or gas extraction, for example by supercritical fluid extraction (SFE) with $CO_2$. The *Cannabis sativa* extract typically contains myrcene, cannabinoids, and terpenes, and also can contain phytocannabinoids and other secondary metabolites.

"Pain disorders" include various diseases causing pain as one of their symptoms—including, but not limited to, those associated with strains, sprains, arthritis or other joint pain, bruising, backaches, fibromyalgia, endometriosis, pain after surgery, diabetic neuropathy, trigeminal neuralgia, postherpetic neuralgia, cluster headaches, psoriasis, irritable bowel syndrome, chronic interstitial cystitis, vulvodynia, trauma, musculoskeletal disorders, shingles, sickle cell disease, heart disease, cancer, stroke, or mouth sores due to chemotherapy or radiation.

The terms "treatment," "treating," and the like are used herein to generally mean obtaining a desired pharmacologic and/or physiologic effect. The effect may be prophylactic, in terms of completely or partially preventing a disease, condition, or symptoms thereof, and/or may be therapeutic in terms of a partial or complete cure for a disease or condition and/or adverse effect, such as a symptom, attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method includes subjects suffering from the undesirable condition or disease, as well as subjects at risk for development of the condition or disease.

By the term "therapeutically effective dose" or "therapeutically effective amount" is meant a dose or amount that produces the desired effect for which it is administered. The exact dose or amount will depend on the purpose of the treatment, and will be ascertainable by one skilled in the art using known techniques (see, e.g., Lloyd (2012) The Art, Science and Technology of Pharmaceutical Compounding, Fourth Edition). A therapeutically effective amount can be a "prophylactically effective amount" as prophylaxis can be considered therapy.

The term "sufficient amount" means an amount sufficient to produce a desired effect.

The term "ameliorating" refers to any therapeutically beneficial result in the treatment of a disease state, e.g., an immune disorder, including prophylaxis, lessening in the severity or progression, remission, or cure thereof. The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

Other Interpretational Conventions

It must be noted that, as used in the specification and the appended claims, the singular forms "a," "an" and "the" include plural referents unless the context clearly dictates otherwise.

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereo centers intends each stereoisomer, and all combinations of stereoisomers, thereof.

Methods of Modulating TRPV1 Activation

We have discovered that a variety of cannabinoids and terpenes have agonistic effects on TRPV1, and that the agonist effects of each compound can be distinguished, both from one another and from the effects of the major TRPV1 agonist in current therapeutic use, capsaicin, by electrophysiological analysis of TRPV1-expressing cells. These compounds can therefore be used, either alone, or in combination with each other, with capsaicin, or with other appropriate compounds, to modulate TRPV1 permeability. Our data support a multivariate model for selection of TRPV1 agonists and agonist mixtures with desirable therapeutic properties. The method allows for bespoke design of formulations that are informed by desired ranges of current amplitude, ion permeation characteristics, and activation/inactivation kinetics. These agonists or agonist mixtures can be chosen based on their predetermined TRPV1 state-related agonist properties to acutely activate TRPV1, desensitize TRPV1 by chronic application, or both, with therapeutic effects.

Accordingly, in a first aspect, methods are presented for modulating TRPV1 channel permeability. The methods comprise externally contacting a TRPV1-expressing cell with at least one compound having a predetermined TRPV1 state-related agonist property. In some embodiments, the method further comprises an earlier step of selecting a compound that has the predetermined TRPV1 state-related agonist property. In some embodiments, the at least one compound comprises a plurality of compounds, each of the plurality of compounds having different TRPV1 state-related properties.

In some embodiments, the predetermined property is ion selectivity. In one embodiment, the ion selectivity is relative permeation of $Na^+$ and $Ca^{2+}$ ions. In one embodiment, the ion selectivity is the magnitude of $Ca^{2+}$ influx. In one embodiment, the ion selectivity is $Na^+$ selectivity. In one embodiment, the ion selectivity is $Ca^{2+}$ selectivity. In one embodiment, the predetermined property is a pore dilation state. In one embodiment, the predetermined property is a TRPV1 channel activation profile. In another embodiment, the predetermined property is a TRPV1 channel inactivation profile. In one embodiment, the predetermined property is a magnitude of a TRPV1-induced ion current. In one embodiment, the predetermined property is TRPV1 channel activation kinetics. In one embodiment, the predetermined property is TRPV1 channel inactivation kinetics. In one embodiment, the predetermined property is calcium-dependent inactivation. In one embodiment, the predetermined property is calcium-independent inactivation.

In various embodiments, contacting the cell with the at least one compound kills the contacted cell. In various embodiments, contacting the cell does not kill the contacted cell. In some embodiments, the contacting is performed in vivo.

In various embodiments, contacting a cell with a TRPV1 state-related agonist induces calcium-dependent cellular signaling pathways. In one embodiment, the signaling pathway results in secretion of secondary mediators. In one embodiment, the signaling pathway results in enzyme activation. In some embodiments, the signaling pathway results in gene expression. In one embodiment, the signaling pathway results in gene regulation. In one embodiment, the signaling pathway results in cellular growth. In one embodiment, the signaling pathway results in cellular death. In one embodiment, the signaling pathway results in cellular replication. In one embodiment, the signaling pathway results in cellular motility.

In various embodiments, the method further comprises administering a pharmaceutical composition comprising at least one compound having a predetermined TRPV1 state-related agonist property.

Compounds

The at least one compound may be a cannabinoid or a terpene.

In various embodiments, the at least one compound is a cannabinoid. In one embodiment, the cannabinoid is cannabinol (CBN). In one embodiment, the cannabinoid is cannabidiol (CBD). In one embodiment, the cannabinoid is cannabigerol (CBG). In one embodiment, the cannabinoid is cannabidivarin (CBDV).

In various embodiments, the at least one compound is a terpene. In one embodiment, the terpene is myrcene. In one embodiment, the terpene is limonene. In one embodiment, the terpene is linalool. In one embodiment, the terpene is phytol. In one embodiment, the terpene is pinene. In one embodiment, the terpene is nerolidol.

Pharmaceutical Compositions

In another aspect, pharmaceutical compositions are provided. The pharmaceutical composition comprises at least one compound having a predetermined TRPV1 state-related agonist property and a pharmaceutically acceptable carrier or diluent. In the context of pharmaceutical compositions, the at least one compound having a predetermined TRPV1 state-related agonist property is the active pharmaceutical ingredient of the composition.

Content of Pharmaceutically Active Ingredient

In typical embodiments, the active ingredient is present in the pharmaceutical composition at a concentration of at least 0.01 mg/ml, at least 0.1 mg/ml, at least 0.5 mg/ml, or at least 1 mg/ml. In certain embodiments, the active ingredient is present in the pharmaceutical composition at a concentration of at least 1 mg/ml, 2 mg/ml, 3 mg/ml, 4 mg/ml, 5 mg/ml, 10 mg/ml, 15 mg/ml, 20 mg/ml, or 25 mg/ml. In certain embodiments, the active ingredient is present in the pharmaceutical composition at a concentration of at least 30 mg/ml, 35 mg/ml, 40 mg/ml, 45 mg/ml or 50 mg/ml.

Formulation Generally

The pharmaceutical composition can be in any form appropriate for human or veterinary medicine, including a liquid, an oil, an emulsion, a gel, a colloid, an aerosol or a solid.

The pharmaceutical composition can be formulated for administration by any route of administration appropriate for human or veterinary medicine, including enteral and parenteral routes of administration.

In various embodiments, the pharmaceutical composition is formulated for administration by inhalation. In certain of these embodiments, the pharmaceutical composition is formulated for administration by a vaporizer. In certain of these embodiments, the pharmaceutical composition is formulated for administration by a nebulizer. In certain of these embodiments, the pharmaceutical composition is formulated for administration by an aerosolizer.

In various embodiments, the pharmaceutical composition is formulated for oral administration, for buccal administration, or for sublingual administration.

In some embodiments, the pharmaceutical composition is formulated for intravenous, intramuscular, or subcutaneous administration.

In some embodiments, the pharmaceutical composition is formulated for intrathecal or intracerebroventricular administration.

In some embodiments, the pharmaceutical composition is formulated for topical administration.

Pharmacological Compositions Adapted for Administration by Inhalation

In some embodiments, unit dosage forms of the pharmaceutical composition described herein are provided that are adapted for administration of the pharmaceutical composition by vaporizer, nebulizer, or aerosolizer. In some embodiments, the dosage form is a vial, an ampule, optionally scored to allow user opening. In particular embodiments, the nebulizer is a jet nebulizer or an ultrasonic nebulizer.

Inhalable compositions are generally administered in an aqueous solution e.g., as a nasal or pulmonary spray. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering the solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien Ed., Elsevier Publishers, New York, 1985; M. Naef et al. Development and pharmacokinetic characterization of pulmonal and intravenous delta-9-tetrahydrocannabinol (THC) in humans, J. PHARM. SCI. 93, 1176-84 (2004); and in U.S. Pat. Nos. 4,778,810; 6,080,762; 7,052,678; and 8,277,781 (each incorporated herein by reference). Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Mucosal formulations are administered as dry powder formulations e.g., comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5 micron mass median equivalent aerodynamic diameter (MMEAD), commonly about 1 micron MMEAD, and more typically about 2 micron MMEAD. Maximum particle size appropriate for deposition within the nasal passages is often about 10 microns MMEAD, commonly about 8 micron MMEAD, and more typically about 4 micron MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI) which rely on the patient's breath, upon pulmonary or nasal inhalation, to disperse the power into an aerosolized amount. Alternatively, the dry powder may be administered via air assisted devices that use an external power source to disperse the powder into an aerosolized amount, e.g., a piston pump.

Pharmacological Compositions Adapted for Oral/Buccal/Sublingual Administration

Formulations for oral, buccal or sublingual administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral, buccal or sublingual administration (capsules, tablets, pills, dragees, powders, granules, and the like), one or more therapeutic agents may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Pharmacological Compositions Adapted for Injection

For intravenous, intramuscular, or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

In various embodiments, the unit dosage form is a vial, ampule, bottle, or pre-filled syringe. In some embodiments, the unit dosage form contains 0.01 mg, 0.1 mg, 0.5 mg, 1 mg, 2.5 mg, 5 mg, 10 mg, 12.5 mg, 25 mg, 50 mg, 75 mg, or 100 mg of the cannabinoid composition. In some embodiments, the unit dosage form contains 125 mg, 150 mg, 175 mg, or 200 mg of the cannabinoid composition. In some embodiments, the unit dosage form contains 250 mg of the cannabinoid composition.

In typical embodiments, the pharmaceutical composition in the unit dosage form is in liquid form. In various embodiments, the unit dosage form contains between 0.1 mL and 50 ml of the pharmaceutical composition. In some embodiments, the unit dosage form contains 1 ml, 2.5 ml, 5 ml, 7.5 ml, 10 ml, 25 ml, or 50 ml of pharmaceutical composition.

In particular embodiments, the unit dosage form is a vial containing 1 ml of the cannabinoid composition at a concentration of 0.01 mg/ml, 0.1 mg/ml, 0.5 mg/ml, or 1 mg/ml. In some embodiments, the unit dosage form is a vial containing 2 ml of the cannabinoid composition at a concentration of 0.01 mg/ml, 0.1 mg/ml, 0.5 mg/ml, or 1 mg/ml.

In some embodiments, the pharmaceutical composition in the unit dosage form is in solid form, such as a lyophilate, suitable for solubilization.

Unit dosage form embodiments suitable for subcutaneous, intradermal, or intramuscular administration include pre-loaded syringes, auto-injectors, and autoinject pens, each containing a predetermined amount of the pharmaceutical composition described hereinabove.

In various embodiments, the unit dosage form is a pre-loaded syringe, comprising a syringe and a predetermined amount of the pharmaceutical composition. In certain pre-loaded syringe embodiments, the syringe is adapted for subcutaneous administration. In certain embodiments, the syringe is suitable for self-administration. In particular embodiments, the preloaded syringe is a single use syringe.

In various embodiments, the preloaded syringe contains about 0.1 mL to about 0.5 mL of the pharmaceutical composition. In certain embodiments, the syringe contains about 0.5 mL of the pharmaceutical composition. In specific embodiments, the syringe contains about 1.0 mL of the pharmaceutical composition. In particular embodiments, the syringe contains about 2.0 mL of the pharmaceutical composition.

In certain embodiments, the unit dosage form is an autoinject pen. The autoinject pen comprises an autoinject pen containing a pharmaceutical composition as described herein. In some embodiments, the autoinject pen delivers a predetermined volume of pharmaceutical composition. In other embodiments, the autoinject pen is configured to deliver a volume of pharmaceutical composition set by the user.

In various embodiments, the autoinject pen contains about 0.1 mL to about 5.0 mL of the pharmaceutical composition. In specific embodiments, the autoinject pen contains about 0.5 mL of the pharmaceutical composition. In particular embodiments, the autoinject pen contains about 1.0 mL of the pharmaceutical composition. In other embodiments, the autoinject pen contains about 5.0 mL of the pharmaceutical composition.

Pharmacological Compositions Adapted for Topical Administration

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the cannabinoid-containing complex mixtures featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearoylphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). The cannabinoid-containing complex mixtures featured in the invention may be encapsulated within liposomes or may form complexes thereto, in particular to cationic liposomes. Alternatively, the cannabinoid-containing complex mixtures may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a C1-10 alkyl ester (e.g., isopropylmyristate IPM), monoglyceride, diglyceride or pharmaceutically acceptable salt thereof.

Dose Ranges

In vivo and/or in vitro assays may optionally be employed to help identify optimal dosage ranges for use. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

Unit Dosage Forms

The pharmaceutical compositions may conveniently be presented in unit dosage form.

The unit dosage form will typically be adapted to one or more specific routes of administration of the pharmaceutical composition.

In various embodiments, the unit dosage form is adapted for administration by inhalation. In certain of these embodiments, the unit dosage form is adapted for administration by a vaporizer. In certain of these embodiments, the unit dosage form is adapted for administration by a nebulizer. In certain of these embodiments, the unit dosage form is adapted for administration by an aerosolizer.

In various embodiments, the unit dosage form is adapted for oral administration, for buccal administration, or for sublingual administration.

In some embodiments, the unit dosage form is adapted for intravenous, intramuscular, or subcutaneous administration.

In some embodiments, the unit dosage form is adapted for intrathecal or intracerebroventricular administration.

In some embodiments, the pharmaceutical composition is formulated for topical administration.

The amount of active ingredient which can be combined with a carrier material to produce a single dosage form will generally be that amount of the compound which produces a therapeutic effect.

Methods of Treatment

In other aspects, methods of treatment are provided.

In one series of embodiments, methods of treating pain are provided. The method comprises administering to a subject with pain an effective amount of a pharmaceutical composition comprising at least one compound having a predetermined TRPV1 state-related agonist property, wherein the at least one compound externally contacts a TRPV1-expressing cell that contributes to the subject's sensation of pain.

In another series of embodiments, methods of treating cardiac hypertrophy are provided. The methods comprise systemically administering to a subject with cardiac hypertrophy an effective amount of a pharmaceutical composition comprising at least one compound having a predetermined TRPV1 state-related agonist property, wherein the at least one compound externally contacts a TRPV1-expressing cardiac cell.

Suitable compounds are described above in Section 5.3.1, incorporated here by reference. Suitable pharmaceutical compositions are described above in Section 5.4, incorporated here by reference.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B(1992).

Methods

Cell Culture:

HEK TRexTRPV1 were cultured in DMEM, 10% Fetal Bovine Serum, 2 mM Lglutamine, 10 µg/ml Blasticidin (Calbiochem, San Diego, Calif.), 400 µg/ml Zeocin (InvivoGen, San Diego, Calif.), where indicated transgene expression was induced using 1 µg/ml Tetracycline for 16-24 hrs. Unless otherwise indicated, basal expression of TRPV1 without induction was sufficient for these studies, and comparisons were made to untransfected HEK where needed. HEKTRex293 over-expressing human TRPV2, human TRPA1 and human TRPM8 were obtained from SB Drug Discovery (Glasgow, Scotland) and cultured as described above. The cannabinoids and terpenes were assayed in HEK cells that have been transfected with the TRPV1 ion channel protein. These cells are called HEK293-V1 cells.

Chemicals, Reagents and Stimulations:

General chemicals were from VWR (West Chester, Pa.) and Sigma Aldrich (St. Louis, Mo.). PMA and Ionomycin were from Calbiochem (Gibbstown, N.J.). IgE anti-DNP is from Sigma and KLH-DNP was from Calbiochem. Capsaicin and Capsazepine were from Sigma Aldrich. Cannabidivarin (CBDV), Cannabichromene (CBC), Cannabidiol (CBD), Cannabidiolic Acid (CBDA), Cannabigerol (CBG), Cannabigerolic Acid (CBGA), Cannabinol (CBN) were from Sigma Aldrich.

Calcium Assay (Bulk Method):

Cells were washed and incubated with 0.2 micromolar Fluo-4 for 30 minutes at 37° C. in a standard modified Ringer's solution of the following composition (in mM): NaCl 145, KCl 2.8, CsCl 10, $CaCl_2$ 10, $MgCl_2$ 2, glucose 10, Hepes.NaOH 10, pH 7.4, 330 mOsm. Cells were transferred to 96-well plates at 50,000 cells/well and stimulated as indicated. Calcium signals were acquired using a Flexstation 3 (Molecular Devices, Sunnydale, USA). Data was analyzed using SoftMax® Pro 5 (Molecular Devices). Where indicated, nomically calcium-free external conditions were achieved by the preparation of 0 mM $CaCl_2$ Ringer solution containing 1 mM EGTA.

Patch Clamp Method:

This technique is used to study ionic currents from HEK293-V1. The voltage across the cell membrane is controlled and the ionic currents associated with changes in voltage are measured. A micropipette tip is pulled to a few micrometers in diameter followed by heating the tip to produce a smooth surface that assists in forming a high resistance seal with the cell membrane. To obtain this high resistance seal, the micropipette is pressed against a cell membrane and suction is applied. The membrane then fuses onto the glass surface creating a high resistance in the gigaohm range. This makes it possible to isolate electronically the ionic currents measured across the membrane patch or across the entire cell.

Electrophysiology:

Patch-clamp experiments were performed in the whole-cell configuration at 21-25° C. Patch pipettes had resistances of 2-3 MΩ. Data was acquired with PatchMaster software (HEKA, Lambrecht, Germany), controlling an EPC-9 amplifier. Voltage ramps of 50 ms spanning the voltage range from −100 to 100 mV were delivered from a holding potential of 0 mV at a rate of 0.5 Hz over a period of 500 ms to 180 seconds (3 minutes). Voltages were corrected for a liquid junction potential of 10 mV. Currents were filtered at 2.9 kHz and digitized at 100 μs intervals. Capacitive currents were determined and corrected before each voltage ramp. The development of currents for a given potential was extracted from individual ramp current records by measuring the current amplitudes at voltages of −80 mV and −80 mV. Data were analyzed with FitMaster (HEKA, Lambrecht, Germany), and IgorPro (WaveMetrics, Lake Oswego, Oreg., USA). Where applicable, statistical errors of averaged data are given as mean±s.e.m with n determinations. The activated current amplitudes are analyzed by nA rather than pA/pF. This decision was made due to high current amplitudes (1 to 6 nA) resulting from the TRPV1 transfection of the channel. Also the cell size selected for patching was in the 9-12 pF range. The analyses in nA and pA/pF were compared and no significant differences were found mainly due to consistent cell size selection and high current amplitudes in the nA range.

For patch-clamp recordings, HEK293 cells were kept in a standard sodium-based external Ringer's solution containing (mM): 140 NaCl, 1 CaCl2, 2 MgCl2, 2.8 KCl, 11 glucose, 10 HEPES-NaOH with a pH of 7.2 and osmolarity of 300 mOsmol. To assess the effects of external Calcium (Ca) on TRPV1 inactivation kinetics, Ca at different levels were tested including 0, 1, and 3 mM. In Experiments with zero external Ca, EGTA 10 mM was added and the Na concentration was lowered to 130 mM to maintain standard osmotic conditions at 300 mOsmol. For rapid external solution application and exchanges we used the SmartSquirt delivery system (Auto-Mate Scientific, San Francisco, Calif., USA) that included four cryo tubes allowing for solution exchanges within one patch. This system included a ValveLink TTL interface between the electronic valves and the EPC10 amplifier (HEKA, Lambrecht, Germany). This electronic configuration allowed for programmable solution changes via the PatchMaster software (HEKA, Lambrecht, Germany).

The cytosol was perfused with an intracellular patch pipette solution containing (mM): 140 Cs-glutamate, 8 NaCl, 1 MgCl2, 3 MgATP, 10 HEPES-CsOH. The pH of the pipette solution was adjusted to pH 7.2 and osmolarity measured at 300 mOsmol. The level of free unbuffered Ca in the cytosol was adjusted using the calculator provided with WebMaxC http://www.stanford.edu/~cpatton/webmaxcS.htm). Cytosol $[Ca_{2+}]_i$ was buffered to 180 and 620 nM with 10 mM Cs-BAPTA and Ca 4.5 or 7.4 mM respectively, calculated with WebMaxC and as indicated in the text. Whenever 10 mM Cs-BAPTA was added, we lowered the external Cs-glutamate from 140 to 120 mM to maintain consistent osmolarities at 300 mOsmol. When experimental aims required using unbuffered Ca that excluded both BAPTA and Ca (identified in the results as Fca), this absence of buffering allowed for free accumulation of internal Ca that was determined primarily by the permeation of external Ca into the cytosol.

Solutions:

Channel currents were assessed via patch clamp experiments in single HEK293 cells overexpressing rat TRPV1. HEK293 cells were kept in sodium-based extracellular Ringer's solution containing 140 mM NaCl, 1 mM $CaCl_2$, 2 mM $MgCl_2$, 2.8 mM KCl, 11 mM glucose, and 10 mM HEPES-NaOH, pH 7.2 and osmolarity 300 mOsmol. The cells' cytosol was perfused with intracellular patch pipette solution containing 140 mM Cs-glutamate, 8 mM NaCl, 1 mM $MgCl_2$, 3 mM MgATP, and 10 mM HEPES-CsOH. The standard internal $Ca^{2+}$ concentration was buffered to 180 nM with 4 mM $Ca^{2+}$ and 10 mM BAPTA. The level of free unbuffered $Ca^{2+}$ was adjusted using the calculator provided with WebMaxC (http://www.stanford.edu/~cpatton/webmaxcS.htm). The pH of the final solution was adjusted to pH 7.2 and osmolarity measured at 300 mOsmol. TRPV1 currents were activated by adding cannabinoids, terpenes, or capsaicin to the above external solution.

Rapid extracellular solution application and exchange was performed with the SmartSquirt delivery system (Auto-Mate Scientific, San Francisco). The system includes a ValveLink TTL interface between the electronic valves and the EPC-9 amplifier (HEKA, Lambrecht, Germany). This configuration allows for programmable solution changes via the PatchMaster software (HEKA, Lambrecht, Germany).

Analysis

Results are generally shown as the mean+standard deviation. The electrophysiology results error bars display standard error of mean (SEM). Statistical significance was determined based on Student's t-test or ANOVA. Adjacent to data points in the respective graphs, significant differences were recorded as follows: single asterisk, $p<0.05$; double asterisk, $p<0.01$; triple asterisk, $p<0.001$; no symbol, $p>0.05$. Experiments are all n of at least 3.

Example 1

TRPV1 State-Related Agonist Properties of Capsaicin

A number of prior studies suggest that TRPV1 can undergo dynamic changes in the channel properties that may contribute to the mechanisms of pain hypersensitivity. By dynamic changes in channel properties, we are referring to the ion selectivity of the TRPV1 ion channel. In biophysical terms, ion selectivity refers to the channel's ability to have a high permeation for a selected ionic species. The ion selectivity of canonical ion channels is not thought to change under various physiological conditions. This understanding has been challenged by recent studies on TRPV1, whose selectivity for specific ions can change from open pore (state 1) to a dilated pore (state 2). In state 1, the channel is ion non-selective and permeable for both $Na^+$ and $Ca^{2+}$. Exposure to the agonist, capsaicin, results in the pore dilating into state 2 in which the pore allows high fluxes of $Ca^{2+}$ and $Na^+$ ions, in addition to allowing permeation of large cations such as N-Methyl-D-glucamine (NMDG).

Figures 1A, 1B:
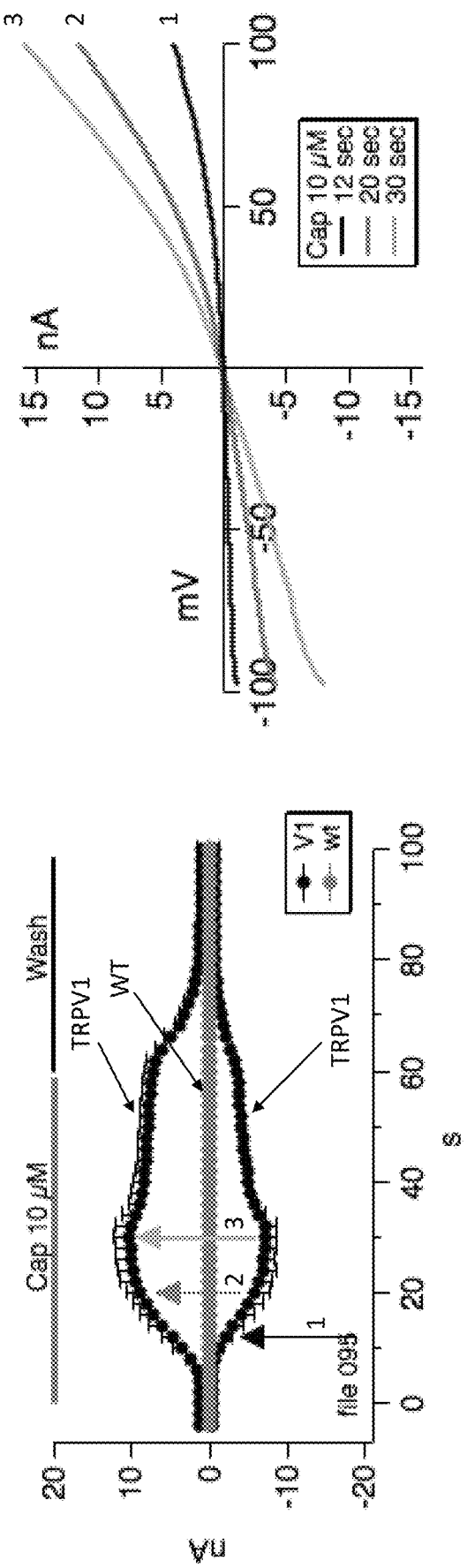
FIG. 1A shows capsaicin (Cap) activation currents in HEK cells transfected with the TRPV1 channel protein. No current is activated in un-transfected wild type (WT) HEK cells.
FIG. 1B shows the current-voltage (IV) relationship undergoing a linear transition: at the early stages of capsaicin application the channel is outwardly rectifying (open channel state 1.

To confirm this finding, we performed whole-cell patch-clamp experiments on wild type and TRPV1-transfected HEK cells. Internal calcium was buffered to 150 µM. Cells were incubated with 10 µM capsaicin for 59 s. The buffer was replaced at 60 s with a wash buffer that did not contain capsaicin (FIG. 1A). The capsaicin-induced currents reverted to baseline upon the removal of capsaicin (indicated by "wash"). No ion channel voltage was seen in the wild type cells, indicating that the voltage induced by capsaicin was due to the exogenous TRPV1 channel.

Voltage ramps were performed at 12 s, 20 s, and 30 s (arrows 1, 2, and 3 in FIG. 1A, results shown in FIG. 1B). At the early stages of capsaicin application the channel is in the open state (state 2, FIG. 1B, lines 1 and 2) but over time the IV relationship became linearized, indicating that the channel underwent a transition into the dilate state (state 2, FIG. 1B, lines 3).

Next, the dynamic selectivity of TRPV1 activation by capsaicin was assessed (FIGS. 2A-2D). Cells were incubated with 10 µM capsaicin in the presence or absence of internal 10 mM BAPTA and 150 nM $Ca^{2+}$. BAPTA is an intracellular calcium chelator.

Figure 2A:
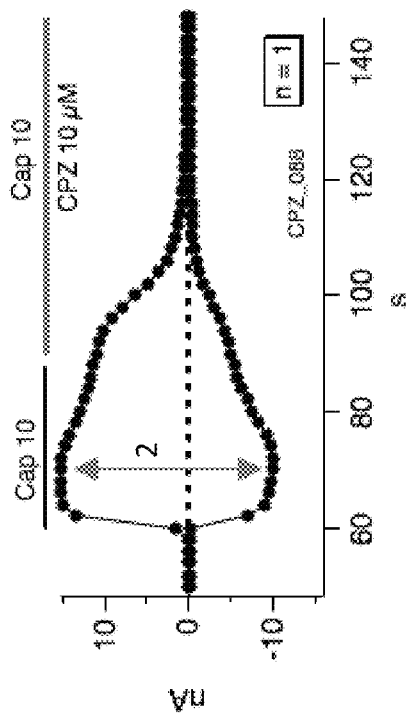
FIGS. 2A-2B shows capsaicin (Cap) activation currents in HEK cells transfected with the TRPV1 channel protein in the presence (FIG. 2A) or absence (FIG. 2B) of internal 10 mM BAPTA and 150 nM $Ca^{2+}$.
Figure 2B:
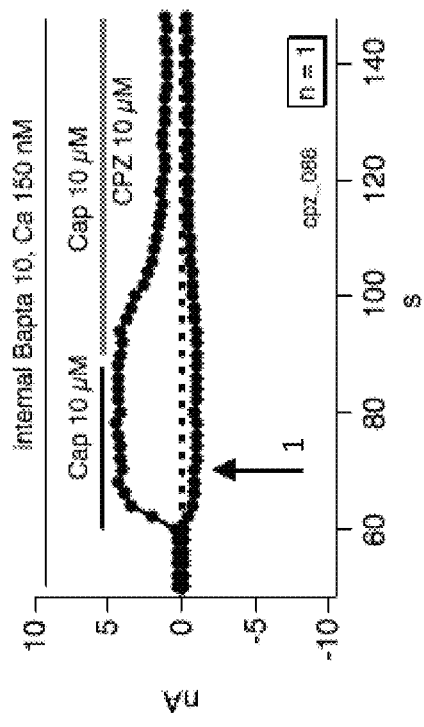
Figure 2C:
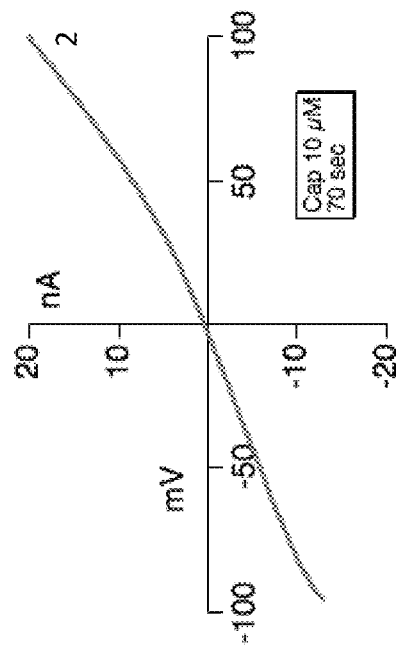
FIGS. 2C-2D show two states of the channel after capsaicin-induced activation: the open channel state 1 (FIG. 2C) and the open dilated state 2 (FIG. 2D). Both state 1 and state 2 can be blocked by capsazepine (CPZ), a well know blocker of the TRPV1 channel.
Figure 2D:
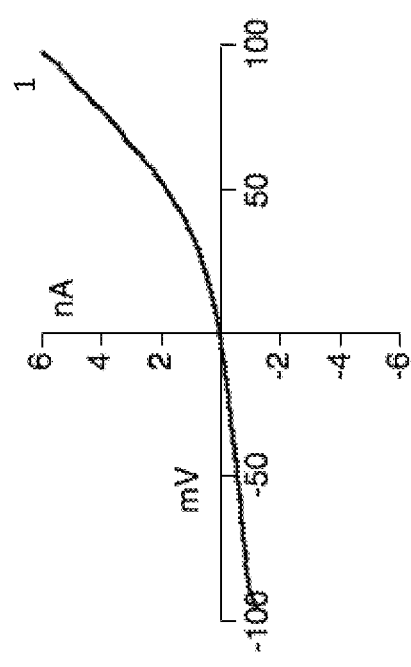

Voltage ramps were performed at 70 s in each experiment (arrows in FIGS. 2A and 2B) and the related IV curves are shown in FIGS. 2C and 2D. In the presence of internal BAPTA and $Ca^{2+}$, capsaicin induced $Na^+$ ion selective TRPV1 activation (state 1, FIGS. 2A and 2C), whereas in the absence of internal BAPTA and $Ca^{2+}$, capsaicin induced $Ca^{2+}$ ion selective TRPV1 activation (state 2, FIGS. 2B and 2C). In both experiments, the addition of Capsazepine (CPZ), a known TRPV1 inhibitor, resulted in rapid TRPV1 channel deactivation, indicating that a TRPV1 inhibitor can block both state 1 and state 2 activation. These results also show that the experimental data are due to specific activation of the TRPV1 channel and not due to destruction of the cellular membrane integrity.

Upon exposure to capsaicin, the TRPV1 channel moved into state 2 and the current amplitude decreased, a phenomenon referred to as desensitization. Desensitization requires high permeation of extracellular calcium to increase the levels of intracellular calcium. Desensitization can be reduced or eliminated by lowering external calcium levels or by buffering internal calcium to low levels.

Example 2

TRPV1 State-Related Agonist Properties of Cannabinoids and Myrcene

Next, the ability of various cannabinoids or terpenes to induce ion selective TRPV1 activation, and the resulting activation of TRPV1 in a state 1 or state 2 condition, was assessed. TRPV1 channels were activated by adding various concentrations of cannabinoids or terpenes to the extracellular solution of patch-clamped HEK293-V1 cells at data point 60. The cannabinoid or terpene solution was replaced by buffer containing 1 µM capsaicin at data point 121 as a positive control for TRPV1 activation. Inward and outward current development is shown over time. Each data point (DP) corresponds to approximately 2 seconds.

Cannabidiol

Cannabidiol (CBD) induced a sustained inward 4-6 nA current compared to the sustained 7-8 nA current induced by application of capsaicin (FIG. 3A). Both CBD and capsaicin also induced an outward current at a lower amplitude than the inward current.

Next, the relationship between the CBD- and capsaicin-induced current and the experimental voltage was analyzed. Voltage ramps were performed at data points 1, 120, and 180 (FIG. 3A, arrows 1-3), and the IV relationship assessed before and after addition of CBD and capsaicin (FIGS. 3B-D). FIG. 3B shows the break-in current ("1" on FIG. 3A) of the cell in the presence of Ringer's solution. FIG. 3C shows the CBD-induced TRPV1 activation ("2" on FIG. 3A). FIG. 3D shows the capsaicin-induced TRPV1 activation ("3" on FIG. 3A). The IV curves of the un-treated cell and after CBD-induced TRPV1 activation have an outwardly-rectifying IV curve consistent with un-dilated TRPV1 (state 1). Under these conditions, the inward current is smaller than the outward current. By contrast the IV curve for capsaicin is linear due to TRPV1 transitioning to the dilated state (state 2). In these conditions, the amplitude of the inward current is close to the amplitude of the outward current.

Cannabinol

Cannabinol (CBN) induced an inward 0.5-2 nA current compared to the sustained 7-8 nA current induced by application of capsaicin (FIG. 4A). CBN also induced an outward current at a lower amplitude than the inward current. The CBN-induced current was rapidly inactivating, in contrast to the sustained TRPV1 currents induced by capsaicin and CBD.

As with CBD, the relationship between the CBN- and capsaicin-induced current and the experimental voltage was analyzed. Voltage ramps were performed at data points 1, 60, and 180 (FIG. 4A, arrows 1-3), and the IV relationship assessed before and after addition of CBN and capsaicin (FIGS. 4B-D). FIG. 4B shows the break-in current ("1" on FIG. 4A) of the cell in the presence of Ringer's solution. FIG. 4C shows the CBN-induced TRPV1 activation ("2" on FIG. 4A). FIG. 4D shows the capsaicin-induced TRPV1 activation ("3" on FIG. 4A). As with the CBN experiments, the IV curves of the un-treated cell and after CBN-induced TRPV1 activation have an outwardly-rectifying IV curve consistent with un-dilated TRPV1 (state 1).

10 µM CBN resulted in greater inward and outward current magnitude (FIG. 5A) as compared to 50 µM CBN.

Interestingly, the transition of the TRPV1 ion channel from a state 1 to state 2 activation is more obvious with the lower concentration of CBN. As seen in the IV curves, the outwardly-rectifying shape of the IV curve of the un-induced cell (arrow 1 on FIG. 5A, and FIG. 5B) becomes more linear after 10 µM CBN application (arrow 2 on FIG. 5A, and FIG. 5C), and is fully linear after capsaicin addition (arrow 3 on FIG. 5A, and FIG. 5D).

Cannabidivarin

Cannabidivarin (CBDV) induced a sustained inward 2-3 nA current compared to the sustained 7-8 nA current induced by application of capsaicin (FIG. 6A). CBDV also induced an outward current at a lower amplitude than the inward current. Like CBD and capsaicin, the CBDV-induced current was sustained and larger than the current induced by CBN.

As with the other cannabinoids, the relationship between the CBDV- and capsaicin-induced current and the experimental voltage was analyzed. Voltage ramps were performed at data points 1, 90, and 180 (FIG. 6A, arrows 1-3), and the IV relationship assessed before and after addition of CBDV and capsaicin (FIGS. 6B-D). FIG. 6B shows the break-in current ("1" on FIG. 6A) of the cell in the presence of Ringer's solution. FIG. 6C shows the CBDV-induced TRPV1 activation ("2" on FIG. 6A). FIG. 6D shows the capsaicin-induced TRPV1 activation ("3" on FIG. 6A). As with the CBN and CBD experiments, the IV curves of the un-treated cell and after CBDV-induced TRPV1 activation have an outwardly-rectifying IV curve consistent with un-dilated TRPV1 (state 1).

Cannabigerol

Figure 7A:
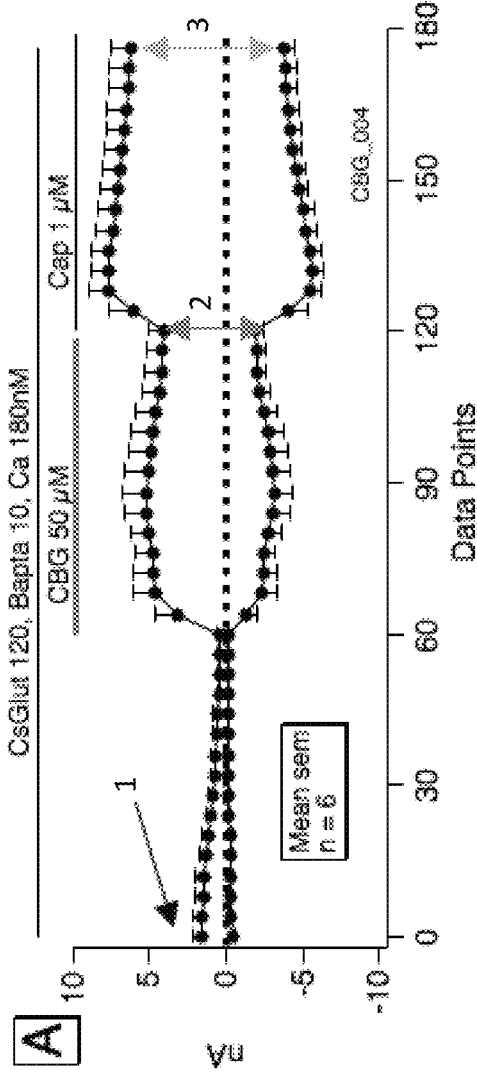
FIGS. 7A-7D show activation of TRPV1 after incubation with control buffer, 50 µM cannabigerol (CBG), and 1 µM capsaicin.

Cannabigerol (CBG) induced a sustained inward 4-5 nA current compared to the sustained 7-8 nA current induced by application of capsaicin (FIG. 7A). CBG also induced an outward current at a lower amplitude than the inward current. Like CBD, CBDV, and capsaicin, the CBG-induced current was sustained and larger than the current induced by CBN.

Figure 7B:
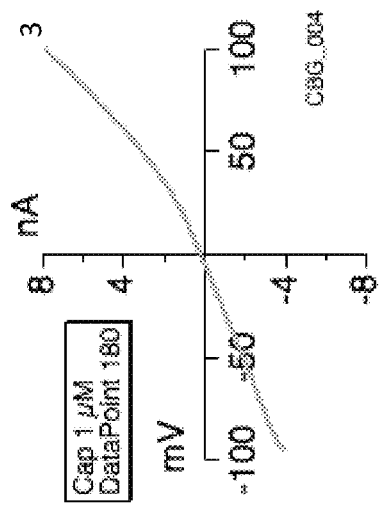
Figure 7C:
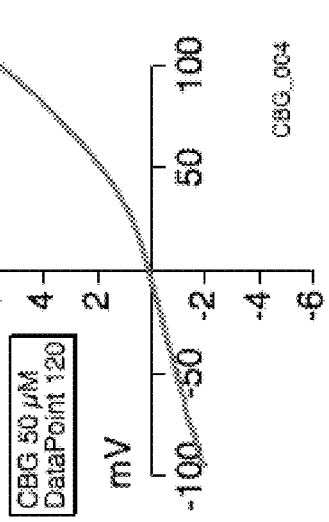
Figure 7D:
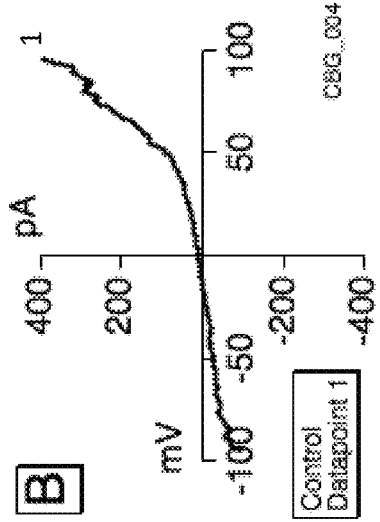

As with the other cannabinoids, the relationship between the CBG- and capsaicin-induced current and the experimental voltage was analyzed. Voltage ramps were performed at data points 1, 120, and 180 (FIG. 7A, arrows 1-3), and the IV relationship assessed before and after addition of CBG and capsaicin (FIGS. 7B-D). FIG. 7B shows the break-in current ("1" on FIG. 7A) of the cell in the presence of Ringer's solution. FIG. 7C shows the CBG-induced TRPV1 activation ("2" on FIG. 7A). FIG. 7D shows the capsaicin-induced TRPV1 activation ("3" on FIG. 7A). As with the CBN, CBD, and CBDV experiments, the IV curves of the un-treated cell and after CBG-induced TRPV1 activation have an outwardly-rectifying IV curve consistent with un-dilated TRPV1 (state 1).

Myrcene

Figure 8A:
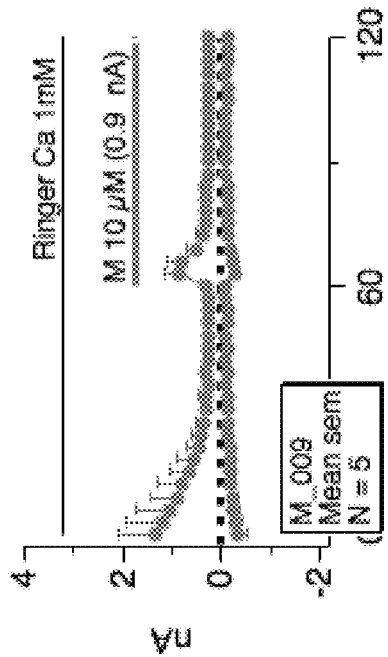
FIGS. 8A-8C illustrate TRPV1 ion channel activation after incubation with increasing amounts of myrcene (M).
Figure 8B:
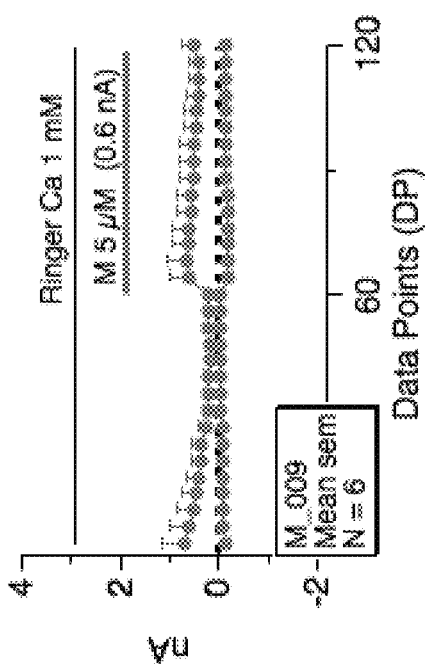
Figure 8C:
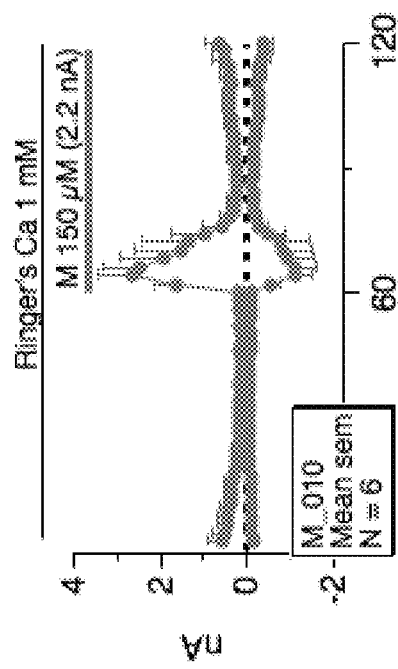

First, various concentrations of myrcene were assessed for TRPV1 activation. As shown in FIGS. 8A-8C, myrcene induced a dose-dependent response in TRPV1 activation. In this figure, each data point (DP) corresponds to approximately 1 second. 5 µM (FIG. 8A), 10 µM (FIG. 8B), and 150 µM (FIG. 8C) myrcene induced 0.5-2.2 nA current compared to 4-10 nA current induced by application of 1 µM capsaicin (not shown). Increasing doses of myrcene result in an inwardly rectifying non-selective cation current which inactivated in a manner dependent both on activation current amplitude (FIGS. 8A-8C) and calcium influx (FIGS. 12A-12I). Induction of TRPV1 activation with 50 µM myrcene followed by 1 µM capsaicin is shown in FIG. 10A-D. A similar experiment using 150 µM myrcene is shown in FIGS. 11A-11C.

FIG. 9A shows the same experiment as FIG. 8A, but with the addition of 1 µM capsaicin after the myrcene application. FIG. 9A shows the average inward and outward currents of 6 independent experiments. 5 µM myrcene induced an approximately 0.5 nA inward current over time, while 1 µM capsaicin induced an approximately 9 nA inward current. Both myrcene and capsaicin also induced an outward current at a lower amplitude than the inward current. FIG. 9B shows a magnified view of the myrcene-induced current. Like CBN, the myrcene-induced current was rapidly inactivating, in contrast to the sustained TRPV1 currents induced by CBD, CBDV, CBG, and capsaicin.

As with the cannabinoid experiments, the relationship between the myrcene- and capsaicin-induced current and the experimental voltage was analyzed. Voltage ramps were performed at data points 1, 59, 119, and 179 (FIG. 9A, arrows 1-4 IV), and the IV relationship assessed before and after addition of myrcene and capsaicin (FIGS. 9C-E). FIG. 9C shows the break-in current ("1 IV" on FIG. 9A) of the cell and the early current development ("2 IV" on FIG. 9A) in the presence of Ringer's solution. FIG. 9D shows the myrcene-induced TRPV1 activation ("3 IV" on FIG. 9A). FIG. 9E shows the capsaicin-induced TRPV1 activation ("4 IV" on FIG. 9A). Similar IV curves were observed for 50 µM myrcene (FIGS. 10B-10D, FIG. 10C is the myrcene-induced IV curve) and 150 µM myrcene (FIGS. 11B-11C, 11B is the myrcene-induced IV curve).

Conclusion

Capsaicin is the therapeutic standard for TRPV1 activation and pain desensitization. However, it is known that therapeutic application of capsaicin as a topical pain treatment results in high levels of initial discomfort prior to desensitization. In these studies, exposure to capsaicin activates the TRPV1 channel into the state 2 dilated channel within a few seconds. In contrast, TRPV1 exposure to the cannabinoids and the terpene myrcene activates the channel primarily into state 1. Interestingly, there are kinetic distinctions among the CBD-, CBN-, CBDV-, CBG-, and myrcene-induced TRPV1 activation and inactivation profiles. These differences suggest that a specific TRPV1 activation or inactivation profile may be selectively induced by the application of a predetermined cannabinoid or terpene, or a combination of cannabinoids or terpenes, to TRPV1-expressing cells. In addition, the cannabinoids and terpene only induced TRPV1 activation in the non-selective state 1, while still inducing current amplitude responses similar to that of capsaicin. Thus, these compounds may offer more therapeutic alternatives for activating TRPV1 in a non-dilated state 1 manner, in contrast to the current capsaicin treatment regime which activates TRPV1 in a dilated state 2 manner.

Example 3

Role of Internal $Ca^{2+}$ Concentration on TRPV1 Activation

To investigate the role of internal calcium on the activation and inactivation dynamics of TRPV1, we next altered the internal $Ca^{2+}$ of HEK239-V1 cells and measured the TRPV1 activation after application of myrcene (FIGS. 12A-12I) and cannabinol (CBN, FIGS. 13A-13F). Cells were perfused with the intracellular patch pipette solution described above supplemented with 0 nM, 180 nM, or 620 nM $Ca^{2+}$ and 10 mM BAPTA.

Role of $Ca^{2-}$ on Myrcene-Induced TRPV1 Activation

10 µM myrcene (FIGS. 12A-12I) was added to cells at data point 60 and replaced with buffer containing 1 µM capsaicin at data point 120. Increasing concentrations of cytosolic $Ca^{2+}$ reduced the TRPV1V1 current peak amplitude activated by external applications of 10 µM myrcene and the subsequent application of capsaicin. In addition to increasing levels of internal calcium shows a minor effect on the falling phase or inactivation kinetics from Myrcene but a stronger effect on inactivation induced by capsaicin.

Voltage ramps were performed at data points 65 and 125 (FIGS. 12A, 12D, and 12G, arrows 1 and 2) and the IV relationship assessed after addition of myrcene and capsaicin. FIGS. 12B and 12C show the myrcene (FIG. 12B) and capsaicin (FIG. 12C) IV curves in the presence of 0 nM Ca2+. FIGS. 8E and 8F show the myrcene (FIG. 12E) and capsaicin (FIG. 12F) IV curves in the presence of 180 nM $Ca^{2+}$. FIGS. 12H and 12I show the myrcene (FIG. 12H) and capsaicin (FIG. 12I) IV curves in the presence of 620 nM $Ca^{2+}$.

Role of $Ca^{2+}$ on CBN-Induced TRPV1 Activation

50 µM CBN (FIGS. 13A-13F) was added to cells at data point 60, supplemented with buffer containing 50 µM CBN and 1 µM capsaicin at data point 120, and replaced with buffer containing 1 µM capsaicin at data point 150. The CBN reduced the peak current amplitude but did not have a strong effect on the inactivation or falling phase kinetics. In comparison with mix CBN and capsaicin application, 0 nM $Ca^{2+}$ internal application removed the falling phase kinetics or inactivation. By contrast the high internal $Ca^{2+}$ at 620 nM showed a significant reduction on current amplitude and acceleration of inactivation kinetics.

Example 4

TRPV1-Mediated Calcium Influx in Response to Terpenes

The cell culture system described in U.S. patent application Ser. No. 15/986,316 was used to test the TRPV1-mediated calcium response to various terpenes. The HEK293 cell line was stably transfected with the pcDNA6TR (Invitrogen, Calif.) plasmid (encoding the tetracycline-sensitive TREx repressor protein), and was maintained in DMEM+10% fetal bovine serum (inactivated at 55° C. for 1 h)+2 mM glutamine in humidified 5% CO2 atmosphere at 37° C. Selection pressure on the TRex 293 cells was maintained by continuous culture in 10 µg/ml Blasticidin (Sigma, St Louis, Mo.).

For production of TRex HEK293 cells with inducible expression of TRPV1, parental cells were electroporated with the rat TRPV1 cDNA in the pcDNA4TO vector and clonal cell lines were selected by limiting dilution in the presence of 400 µg/ml zeocin (Invitrogen, Calif.). TRPV1 expression was induced using 1 µg/ml tetracycline for 16 h at 37° C. Stable lines were screened for inducible protein expression using anti-FLAG Western blot, and inducible expression was confirmed.

Calcium responses mediated by TRPV1 were tested by calcium assay in the cell culture system. Cells were washed and incubated with 0.2 µM fluo-4 acetoxymethyl ester ("Fluo-4") for 30 minutes at 37° C. in a standard modified Ringer's solution of the following composition (in mM): NaCl 145, KCl 2.8, CsCl 10, CaCl2 10, MgCl2 2, glucose 10, Hepes.NaOH 10, pH 7.4, 330 mOsm. Cells were transferred to 96-well plates at 50,000 cells/well and stimulated as indicated. The terpenes used were alpha-bisabool, alpha-pinene, myrcene, camphene, linalool, ocimene, humulene, beta-caryophyllene, beta-pinene, limonene, and nerolidol. The terpenes were diluted in DMSO and added to the wells to a final concentration of 10 µM. Vehicle (DMSO) alone was run as a negative control and subtracted from the terpene traces. Calcium signals were acquired using a Flexstation 3 (Molecular Devices, Sunnydale, USA). Data was analyzed using SoftMax® Pro 5 (Molecular Devices).

FIG. 14 shows the effects of various terpenes on TRPV1-mediated calcium entry. Myrcene treatment resulted in the greatest amount of calcium influx, while nerolidol resulted in a brief initial calcium influx. The remaining terpenes, alpha-bisabool, alpha-pinene, camphene, linalool, ocimene, humulene, beta-caryophyllene, beta-pinene, and limonene resulted in little to no calcium influx as compared to vehicle alone.

Example 5

Effect of Myrcene on TRP Channels

Next, the effect of myrcene to activate various TRP channels was detected. HEK293 cells were stably transfected with TRPA1, TRPM8, and TRPV2, as previously described. These TRP channels, in addition to TRPV1, are associated with sensory neuron bundles.

Calcium responses mediated by TRPA1, TRPM8, TRPV2, and TRPV1 were tested by calcium assay in the cell culture system. Cells were washed and incubated with 0.2 µM fluo-4 acetoxymethyl ester ("Fluo-4") for 30 minutes at 37° C. in a standard modified Ringer's solution of the following composition (in mM): NaCl 145, KCl 2.8, CsCl 10, CaCl2 10, MgCl2 2, glucose 10, Hepes.NaOH 10, pH 7.4, 330 mOsm. Cells were transferred to 96-well plates at 50,000 cells/well and stimulated with 10 µM myrcene diluted in DMSO. Vehicle (DMSO) was used as a negative control. Vehicle traces were subtracted from the myrcene traces for each cell line.

As shown in FIGS. 15A-D, myrcene activated only the cells overexpressing TRPV1 (FIG. 15C) and not the cells expressing TRPA1 (FIG. 15A), TRPM8 (FIG. 15B), or TRPV2 (FIG. 15D), indicating that myrcene is a TRPV1-channel specific activator.

Example 6

Calcium Fluxes in HEK-TRPV1 Overexpressing Cells Initiated by Cannabinoids

Calcium fluxes in response to various cannabinoids were studied in HEK-TRPV1 overexpressing cells.

Figure 16B:
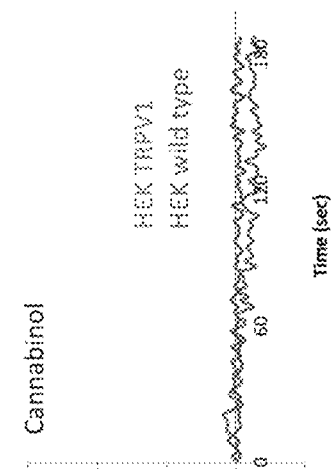
Figure 16A:
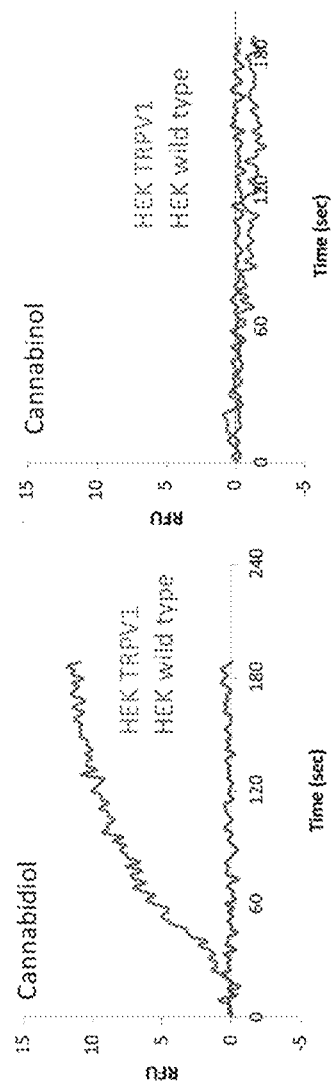
Figure 16D:
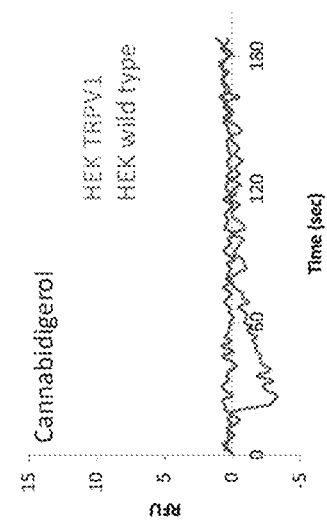
Figure 16C:
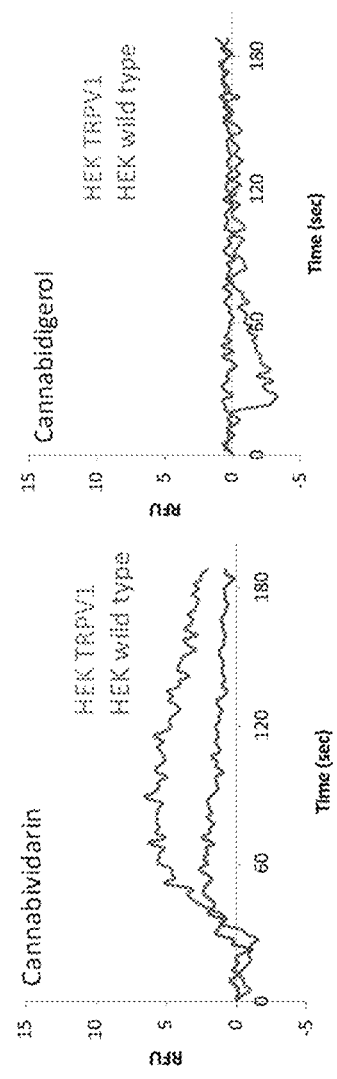

As shown in FIGS. 16A-H, a variety of cannabinoids were capable of initiating $Ca^{2+}$ fluxes in HEK-TRPV1 overexpressing cells, except for cannabigerol and cannabinol. Comparative responses to a single dose (10 µM concentration) of a variety of cannabinoids were made in the presence of 1 mM external $Ca^{2+}$, which are population-based, or bulk $Ca^{2+}$, measurements with each trace representing averaged triplicates of 100,000 cells per sample. It is noted that in most cases, these responses were dependent on the overexpression of TRPV1, with WT HEK293 responding slightly to cannabidivarin and cannabigerolic acid. For comparison purposes, FIG. 16H shows the response for Capsaicin. For each of the cannabinoid compounds, dose responses at the population level were performed. CBG at dosing concentrations of 30-50 μM imitated small calcium fluxes. CBN at concentrations of 30-50 μM initiated small and transient calcium transient fluxes. The lower limit of detectable calcium responses in this system varied from 10-100 nM (CBDV, CBGA) to 1-10 μM.

Example 7

TRPV1 Conductances Evoked by Capsaicin and CBD in the Presence of Capsazepine

TRPV1 conductances in response to Capsaicin and CBD were tested in the presence of Capsazepine.

The effects of Capsaicin and CBD upon TRPV1 conductance were first examined using whole-cell patch-clamping experiment. The fidelity of the HEK-TRVP1 expression system was verified for the detection of the TRPV1 conductances. When Capsaicin (Cap) at 50 nM concentration was applied for 60 seconds, an outwardly rectifying TRPV1 current was recorded while the application of Capsazepine (CPZ) at 10 μM concentration reduced both the inward and outward currents during a subsequent 30 second application, as illustrated in FIGS. 17A and 17B. Furthermore, when CBD at 30 μM concentration was applied to the TRPV1 overexpression system, an outwardly rectifying current recorded and was subsequently reduced by CPZ application 30 seconds later, as illustrated in FIGS. 17C and 17D. These data verifies that this expression system is reporting TRPV1 currents which are responsive to both Capsaicin and cannabinoids, such as CBD.

Example 8

Diverse TRPV1 Activation Responses Initiated by CBD, CBN, CBDV, and CBG

Activation of TRPV1 was studied in response to difference concentrations of cannabinoids, i.e., CBD, CBN, CBDV, and CBG.

Current development graphs of TRPV1 in response to various concentrations (30 μM, 50 μM, and 150 μM) of CBD, CBDV, CBN, and CBG are shown in FIGS. 18A-C. These responses were measured under unbuffered internal and external $Ca^{2+}$ concentrations. This unbuffered condition allowed for free accumulation of internal $Ca^{2+}$ that was determined by permeation of external $Ca^{2+}$ into the cytosol.

The kinetics of the activation and deactivation of TRPV1 via cannabinoid application is affected by the dose and the type of cannabinoid, as illustrated by the individual Imax graphs as shown in FIGS. 19A-L for CBD, CBDV, CBN, and CBG respectively. As can be seen, as the concentration increased from 30 μM to 50 μM to 150 μM, the speed of both activation and deactivation accelerated. The activation kinetics also showed that the time to reach maximal current peak was accelerated, which resulted in less amount of time spent at peak current. Furthermore, FIG. 20A-D show the attained Imax for each cannabinoid used by dosing concentration. These results demonstrated that the maximal attained current was variant between the different cannabinoids with typical Imax ranging from 1-4 nA depending upon the dosing concentration and the cannabinoid species.

Example 9

EC50 Measurements of Cannabinoid Activations of TRPV1

EC50 for activation of TRPV1 were calculated for CBD, CBDV, CBN, and CBG.

The Imax and mean Imax per dose were measured for CBD, CBBV, CBN, and CBG, and these data were used to calculate and generate the corresponding EC50 values as shown in FIGS. 21A-D, and as tabulated in Table 1.

TABLE 1

EC50 Values and Various Kinetic Parameters of CBD, CBDV, CBN, and CBG

| | Cannabinoid | | | | | | | | | | | | | | | |
|---|---|---|---|---|---|---|---|---|---|---|---|---|---|---|---|---|
| | CBD | | | | CBDV | | | | CBN | | | | CBG | | | |
| | EC50 at TRPV1 (micromolar) | | | | | | | | | | | | | | | |
| | 30 | | | | 56 | | | | 36 | | | | 19 | | | |
| | Dose (micromolar) | | | | | | | | | | | | | | | |
| | 10 | 30 | 50 | 150 | 10 | 30 | 50 | 150 | 10 | 30 | 50 | 150 | 10 | 30 | 50 | 150 |
| Max I amplitude (nA) | 0.8 | 2.2 | 1.6 | 3.5 | 0.5 | 1.5 | 0.9 | 3.9 | 0.4 | 0.6 | 1.5 | 1.8 | 0.2 | 0.6 | 0.7 | 0.9 |
| Time to max (secs) | 178 | 180 | 130 | 96 | 148 | 136 | 82 | 62 | 174 | 176 | 120 | 82 | 120 | 94 | 96 | 92 |
| Rate of inactivation (dpsec$^{-1}$) | 0 | 0 | .02 | .042 | 0 | .013 | .009 | .14 | 0 | 0 | .010 | .019 | 0 | .007 | .008 | .014 |

Example 10

Dependence of External and Internal Calcium Concentrations of Cannabinoid Regulation of TRPV1

The dependency of CBD responses on external calcium levels was first studied while buffering the internal calcium level to a constant concentration of 180 nM (which is close to resting cytosolic levels), to a concentration of 0 nM, or leaving the internal calcium levels unbuffered (Fca), as shown in FIGS. 22A-C. Also illustrated are the time courses of current Imax with external calcium at 0, 1 or 3 mM under each of the three internal buffering conditions. Under any constant internal calcium condition, external calcium concentrations influenced the activation time and inactivation kinetics of the TRPV1 responses. For example, FIG. 22A shows that lower external calcium concentrations slow activation kinetics, due to the current carrying contribution of the calcium ions, and lead to far slower inactivation once maximal currents were obtained. By contrast, increasing the external calcium concentrations from 1 to 3 mM showed no effect on activation kinetics but resulted in the acceleration of the inactivation kinetics. Furthermore, FIG. 22B shows the data, normalized to Imax, with constant internal calcium concentration of 180 nM, as well as external calcium constant for each panel. These data highlight the differences in current development when sodium (0 $Ca_{ext}$, 0 $Ca_{int}$) rather than a mix of sodium/calcium ions are flowing through the non-selective cation channel of TRPV1.

The hypothesis that increasing external calcium concentrations accelerates the activation kinetics followed by a faster inactivation kinetics, with no calcium buffering, was also demonstrated, as shown in FIGS. 23A-D. Furthermore, the effect of internal calcium concentrations on shaping of the kinetics of responses to CBD and CBN were also explored. As shown in FIGS. 23A-D and FIGS. 24A-D, under constant external calcium conditions and dosing concentrations of the respective cannabinoids, higher internal calcium concentrations (from Ca 0 nM to Ca 180 nM, 620 nM, and unbuffered Fca) were associated with lower attained maximal currents and faster inactivation of developed currents. The documented cytosolic calcium-dependent inactivation of TRPV1 was also important. As demonstrated in FIGS. 23A-D, CBD caused gradual current development, which inactivated only when internal calcium is buffered above zero. Furthermore, when internal calcium concentration was buffered to 620 nM, the TRPV1 channel became completed inactivated. On the other hand, CBN caused a different presentation of TRPV1, which activated quickly, but rapidly inactivated with a slower kinetic profile, presumably in relationship to the amount of calcium entering via the channel, as shown in FIGS. 24A-D. However, in some cases, inactivation seemed to outpace current development, leading to inactivation and cancellation of the channel's flux, as can be seen in FIGS. 23C-D and FIGS. 24C-D for CBD and CBN respectively with 620 nM internal or unbuffered calcium concentrations. Additionally, the effect on internal calcium concentrations on responses to CBD and CBDV, with low and high doses, were studied and the results are shown in FIGS. 25A-B, FIGS. 26A-B, FIGS. 27A-B, and FIGS. 28A-B respectively. Similarly, high doses of cannabinoid inactivated faster as associated with increased availability of calcium in the cytosol. Table 2 summarizes the results of CBD-induced regulation of the physiological properties of TRPV1, as discussed in this example.

TABLE 2

CBD-induced regulation TRPV1

| Internal $Ca^{2+}$ Level | CBD-induced current property | External $Ca^{2+}$ Level (mM) | | |
|---|---|---|---|---|
| | | 0 | 1 | 3 |
| 0 | Max rate of activation | 1.1% per S 136 S | 1.9% per S 94 S | 3% per S 82 S |
| | Time to max amplitude | 0.41% per S | 0.82% per S | 0.94% per S |
| | Rate of inactivation | | | |
| 180 nM | Max rate of activation | 1.6% per S 108 S | 1.6% per S 116 S | 2.4% per S 92 S |
| | Time to max amplitude | 0.67% per S | 0.71% per S | 0.72% per S |
| | Rate of inactivation | | | |
| >620 nM (free $Ca^{2+}$) | Max rate of activation | 0.83% per S 160 S | 1.5% per S 120 S | 2.7% per S 88 S |
| | Time to max amplitude | 0.49% per S | 1.1% per S | 1% per S |
| | Rate of inactivation | | | |

Example 10

Differences of Cannabinoid Regulation of TRPV1 and Capsaicin Responses

TRPV1 is a two-state channel. Under Capsaicin activation, TRPV1 passed through a rectifying state rapidly, followed by attainment of a non-rectifying, pore-dilated state as characterized by a linear I/V relationship and high level of permeability, including small cations, such as sodium, to large cations, such as N-Methyl-D-glucamine (NMDG). This pore-dilation leads to sustained and high permeation characteristics of the channel to Capsaicin, which are important drivers of neuronal activation and eventual desensitization of the neuron due to unfettered calcium and sodium entries. As such, the two-state behavior of TRPV1 in response to cannabidiol was examined. First, the two-state nature of TRPV1 with Capsaicin was determined. As shown in FIGS. 29A-C and FIG. 30, low (30 nM) and medium (100 nM) doses of Capsaicin resulted in rectifying currents, but a higher concentration (500 nM) did not. On the other hand, both dilated and non-dilated states of the current were sensitive to Capsazepine, as shown in FIGS. 29A-C. Furthermore, FIGS. 31A-C and FIG. 32 demonstrated the increasing permeation of N-Methyl-D-glucamine (NMDG) as the rectifying nature of the channel decreased, which led to TRPV1 attaining its dilated state. This further illustrates that the linearized I/V relationship is indeed a marker of the dilated, or NMDG-permeant, state.

Next, the state transition of TRPV1 in response to CBD was explored. At highly attained Imax and induction times, the TRPV1 currents remained rectified and sensitive to Capsazepine, as demonstrated in FIGS. 33-36. Additionally, even when the currents were attained at about 10 nA, there was no transition to the pore-dilated state in response to CBD dosing. Even with induction times of 0-25 hours and CBD dosing concentrations of up to 150 μM, only one recording of CBD causing a linear non-rectifying current to develop was observed in a cell with a large breaking current. Similarly, a lack of attainment of the pore-dilated state for CBG and CBDV were also observed and shown in FIGS. 37-40C.

Example 11

Cannabinoid Responses at Different TRP Channels

This example shows the different responses of a variety of cannabinoids at TRPV2, TRPM8, and TRPA1 channels.

The potential for different cannabinoids to target specific TRP channels, or to co-target more than one channel type, are of potential therapeutic options for the treatment and management of pain. Comparison of the impacts of a variety of cannabinoid on overexpression systems for TRPV2, TRPM8, and TRPA1 were performed in a side-by-side fashion, under bulk calcium assays where the measurements with each trace representing averaged triplicates of 100,000 cells per sample. As shown in FIGS. 41-43 and summarized in Table 3, there are clear differences in responsiveness between cannabinoids at a single channel type than between channel types to a given cannabinoid.

TABLE 3

| Bulk calcium assay with mean maximal $Ca^{2+}$ signal RFU achieved 0-180 s (SD) | | | | |
|---|---|---|---|---|
| | TRPV1 | TRPV1 | TRM8 | TRPA1 |
| CBD | 11.88 (0.23) | 12.53 (0.28) | 1.12 (0.02) | 1.28 (0.03) |
| CBN | 0.89 (0.08) | 4.03 (0.64) | 0.09 (0.01) | 10.97 (0.4) |
| CBDV | 6.51 (0.07) | 13.07 (0.03) | 3.89 (0.05) | 16.17 (2.68) |
| CBC | 3.23 (0.12) | 21.66 (1.89) | 0.97 (0.03) | 15.13 (3.35) |
| CBDA | 4.62 (0.66) | 3.69 (1.2) | 1.92 (0.04) | 10.09 (3.08) |
| CBG | 0.41 (0.04) | 2.19 (0.62) | 2.25 (0.46) | 10.22 (1.29) |
| CBGA | 13.77 (0.31) | 0.78 (0.02) | 0.3 (0.01) | 3.65 (1.11) |

These data, in combination with the TRPV1 results as discussed above, can provide a foundation for rational design of therapeutics strategies on the basis of response kinetics, desensitization and receptor selectivity.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

The invention claimed is:

1. A method of treating a subject, comprising:
    administering to a subject who has a condition selected from cardiac hypertrophy, urinary cystitis, and hearing loss, an effective amount of a pharmaceutical composition comprising cannabigerolic acid (CBGA), wherein after administration, CBGA contacts a TRPV1-expressing cell.

2. The method of claim 1, wherein the pharmaceutical composition further comprises cannabinol (CBN), cannabidiol (CBD), cannabigerol (CBG), or cannabidivarin (CBDV).

3. The method of claim 2, wherein the pharmaceutical composition further comprises at least one terpene, wherein the at least one terpene is selected from myrcene, beta-caryophyllene, limonene, linalool, phytol, nerolidol, and pinene.

4. The method of claim 3, wherein the at least one terpene is myrcene.

5. The method of claim 4, wherein the pharmaceutical composition comprises cannabigerol (CBG).

6. The method of claim 1, wherein the pharmaceutical composition further comprises myrcene and beta-caryophyllene.

7. The method of claim 1, wherein the condition is cardiac hypertrophy.

8. The method of claim 1, wherein the condition is urinary cystitis.

9. The method of claim 1, wherein the condition is hearing loss.

10. The method of claim 1, wherein contacting the cell kills the contacted cell.

11. The method of claim 1, wherein contacting the cell does not kill the contacted cell.

* * * * *

UNITED STATES PATENT AND TRADEMARK OFFICE
CERTIFICATE OF CORRECTION

PATENT NO. : 11,260,044 B2
APPLICATION NO. : 16/420004
DATED : March 1, 2022
INVENTOR(S) : Small-Howard et al.

Page 1 of 1

It is certified that error appears in the above-identified patent and that said Letters Patent is hereby corrected as shown below:

On the Title Page

Item (73), in Column 1, in "Assignee", Line 2, delete "Ottowa (CA)" and insert -- Ottawa, ON (CA) --, therefor.

Signed and Sealed this
Fourth Day of October, 2022

Katherine Kelly Vidal
*Director of the United States Patent and Trademark Office*